US012247256B2

(12) United States Patent
Herberg et al.

(10) Patent No.: US 12,247,256 B2
(45) Date of Patent: Mar. 11, 2025

(54) METHOD OF IDENTIFYING A SUBJECT HAVING KAWASAKI DISEASE

(71) Applicants: Imperial College Innovations Limited, London (GB); The Regents of the University of California, Oakland, CA (US)

(72) Inventors: Jethro Herberg, London (GB); Victoria Wright, London (GB); Michael Levin, London (GB); Clive Hoggart, London (GB); Myrsini Kaforou, London (GB); Jane Burns, San Diego, CA (US)

(73) Assignees: IMPERIAL COLLEGE INNOVATIONS LIMITED, London (GB); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 957 days.

(21) Appl. No.: 17/265,579

(22) PCT Filed: Aug. 5, 2019

(86) PCT No.: PCT/EP2019/071052
§ 371 (c)(1),
(2) Date: Feb. 3, 2021

(87) PCT Pub. No.: WO2020/030609
PCT Pub. Date: Feb. 13, 2020

(65) Prior Publication Data
US 2021/0246506 A1    Aug. 12, 2021

(30) Foreign Application Priority Data

Aug. 4, 2018 (GB) .................................... 1812712
Aug. 30, 2018 (GB) .................................... 1814112

(51) Int. Cl.
*C12Q 1/6837* (2018.01)
*C12Q 1/686* (2018.01)
*C12Q 1/6876* (2018.01)

(52) U.S. Cl.
CPC ......... *C12Q 1/6876* (2013.01); *C12Q 1/6837* (2013.01); *C12Q 1/686* (2013.01)

(58) Field of Classification Search
CPC .... C12Q 1/6876; C12Q 1/6837; C12Q 1/686; C12Q 1/6883; C12Q 2600/158; Y02A 50/30
See application file for complete search history.

(56) References Cited

FOREIGN PATENT DOCUMENTS

| CN | 103492590 A | 1/2014 |
|---|---|---|
| CN | 108034712 A | 5/2015 |

(Continued)

OTHER PUBLICATIONS

Ramírez-Torres et al., "Proteomics and gene expression analyses of squalene-supplemented mice identify microsomal thioredoxin domain-containing protein 5 changes associated with hepatic steatosis," Journal of Proteomics, vol. 77, pp. 27-39. (Year: 2012).*

(Continued)

*Primary Examiner* — Angela M. Bertagna
*Assistant Examiner* — Francesca Filippa Giammona
(74) *Attorney, Agent, or Firm* — Prismatic Law Group, PLLC; Ronald J. Kamis

(57) ABSTRACT

A method of identifying a subject having Kawasaki disease (KD), which includes discriminating the subject from a subject having another condition, for example other infectious and inflammatory conditions, such as those that present similar symptoms to KD. Also provided is a minimal gene signature employed in the method, as well as primers, probes and gene chips for use in the method.

12 Claims, 10 Drawing Sheets

(56) References Cited

FOREIGN PATENT DOCUMENTS

| EP | 2116618 | A1 | 11/2009 | |
|---|---|---|---|---|
| JP | 2006333770 | A | 12/2006 | |
| WO | 2011049053 | A1 | 4/2011 | |
| WO | 2015061441 | A1 | 4/2015 | |
| WO | 2015127405 | A2 | 8/2015 | |
| WO | 2016014761 | A1 | 1/2016 | |
| WO | WO-2016170348 | A2 * | 10/2016 | ............... A61P 1/00 |
| WO | 2017214061 | A1 | 12/2017 | |

OTHER PUBLICATIONS

Chang et al., "Viral infections associated with Kawasaki disease," Journal of the Formosan Medical Association, vol. 113, pp. 148-154. (Year: 2013).*
Wright et al., JAMA Pediatrics vol. 172 No. 10 Aug. 6, 2018, pp. e182293.
Preeti Jaggi et al. PLOS ONE vol. 13, No. 5 May 29, 2018 p. e0197858.
Popper et al. Journal of Infectious Diseases JID, vol. 200 No. 4, Aug. 15, 2009, pp. 657-666.
PCT International Search Report and Written Opinion for PCT/EP2019/071052.
Illumina Inc., "Illumina HumanHT-12 V3.0 Expression Beadchip", Gene Expression Omnibus, Platform GPL6947, 4 pages, Jun. 10, 2008.
Ebihara et al., "Differential Gene Expression of S100 Protein Family in Leukocytes from Patients with Kawasaki Disease", European Journal of Pediatrics, vol. 164(7): pp. 27-28, 2005.
Esmaeili et al., "Exploring Kawasaki Disease-Specific Hub Genes Revealing a Striking Similarity of Expression Profile to Bacterial Infections Using Weighted Gene Co-Expression Network Analysis (WGCNA) and Co-expression Modules Identification Tool (CEMiTool): an Integrated Bioinformaticsand Experimental Study", Immunobiology, 38 pages, Jul. 4, 2020.
Hoang et al., "Global Gene Expression Profiling Identifies New Therapeutic Targets in Actute Kawasaki Disease", Genome Medicine, vol. 6(102): pp. 1-13, 2014.
"*Homo sapiens* Calcium Voltage-Gated Channel Subunit Alpha1 E (CACNA1E), Transcript Variant 1, mRNA", Database GenBank [online], Accession No. NM_001205293, 14 pages, Jun. 25, 2018.
"*Homo sapiens* DNA Damage Induced Apoptosis Suppressor (DDIAS), Transcript Variant 1,mRNA", Database GenBank [online], Accession No. NM_145018, 5 pages, May 19, 2018.
"*Homo sapiens* Kelch Like Family Member 2 (KLHL2), Transcript Variant 1, mRNA", Database GenBank [online], Accession No. NM_007246, 6 pages, Jun. 24, 2018.
"*Homo sapiens* Pyridine Nucleotide-Disulphide Oxidoreductase Domain 2 (PYROXD2), mRNA", Database GenBank [online], Accession No. NM_032709, 5 pages, Jul. 8, 2018.
"*Homo sapiens* Spermine Oxidase (SMOX), Transcript Variant 1, mRNA", Database GenBank [online], Accession No. NM_175839, 5 pages, Jun. 25, 2018.
Tai-Ming Ko et al., "CXCL10/IP-10 Is a Biomarker and Mediator for Kawasaki Disease" Circ Res. 2015;116:876-883. DOI: 10.1161/CIRCRESAHA. 116.305834.
Yayoi Kimura et al., "Identification of candidate diagnostic serum biomarkers for Kawasaki disease using proteomic analysis ", Scientific Reports | 7:43732 | DOI: 10.1038/srep43732, Mar. 6, 2017.
Caroline Galeotti et al., "Predisposing factors, pathogenesis and therapeutic intervention of Kawasaki disease", Drug Discovery Today, vol. 21, No. 11, Nov. 2016, https://doi.org/10.1016/j.drudis.2016.08.004).

* cited by examiner

Fig 1. Assignment of patients to diagnostic groups
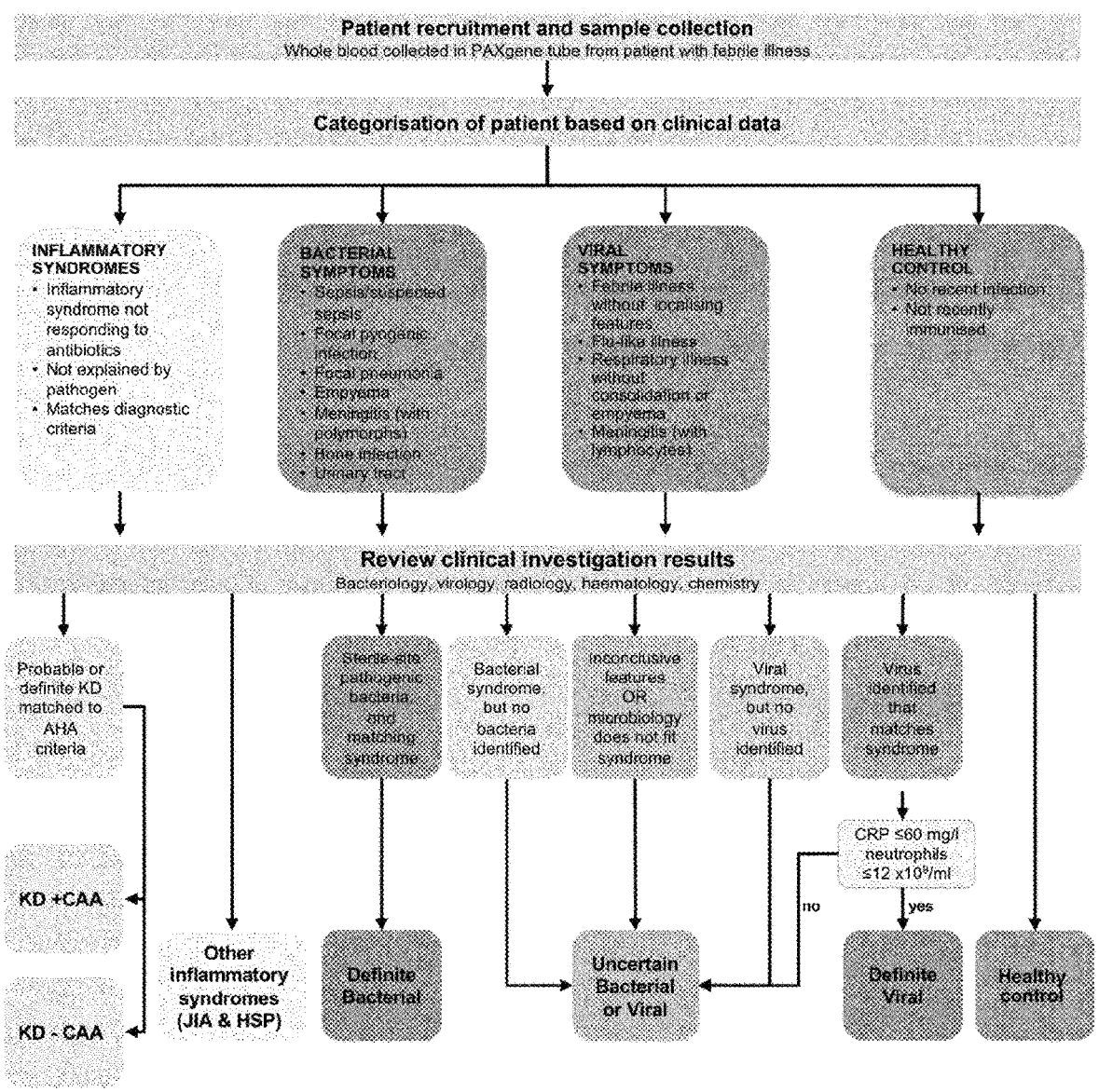

Fig 2. Study design
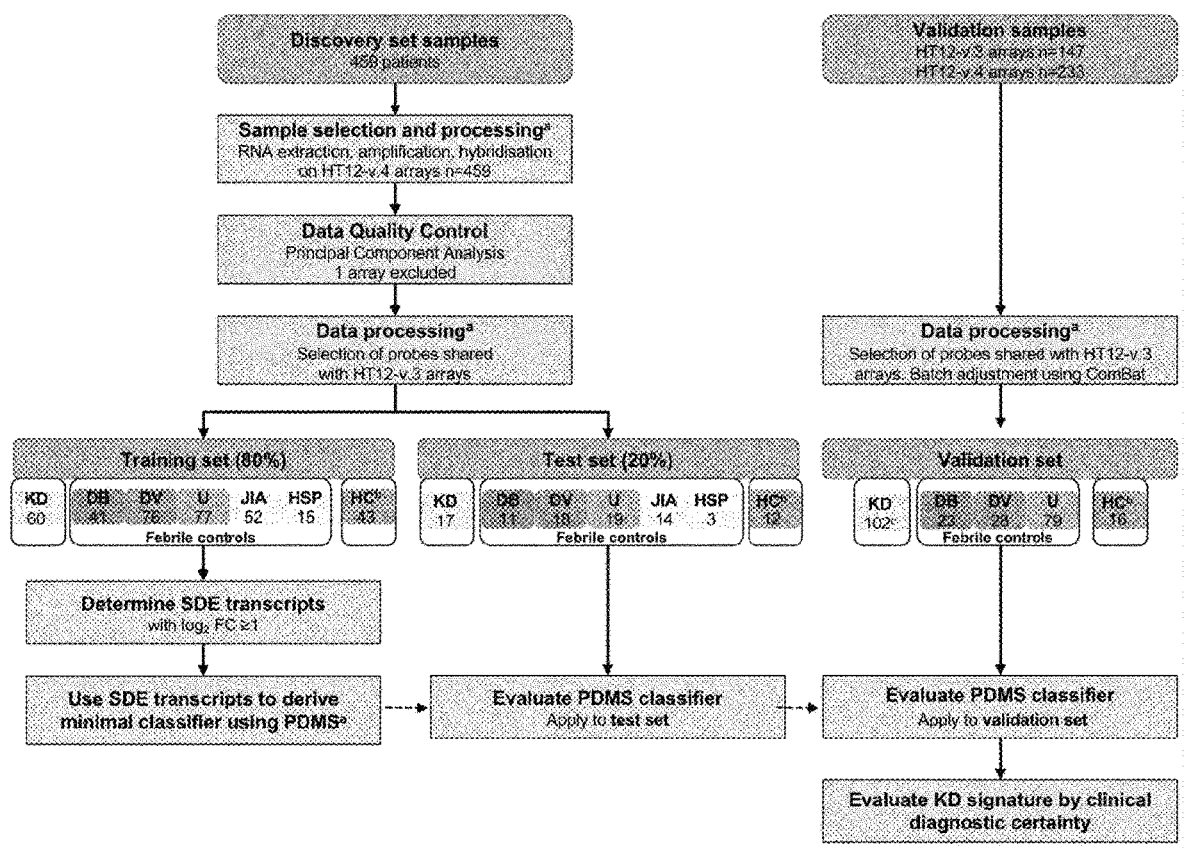

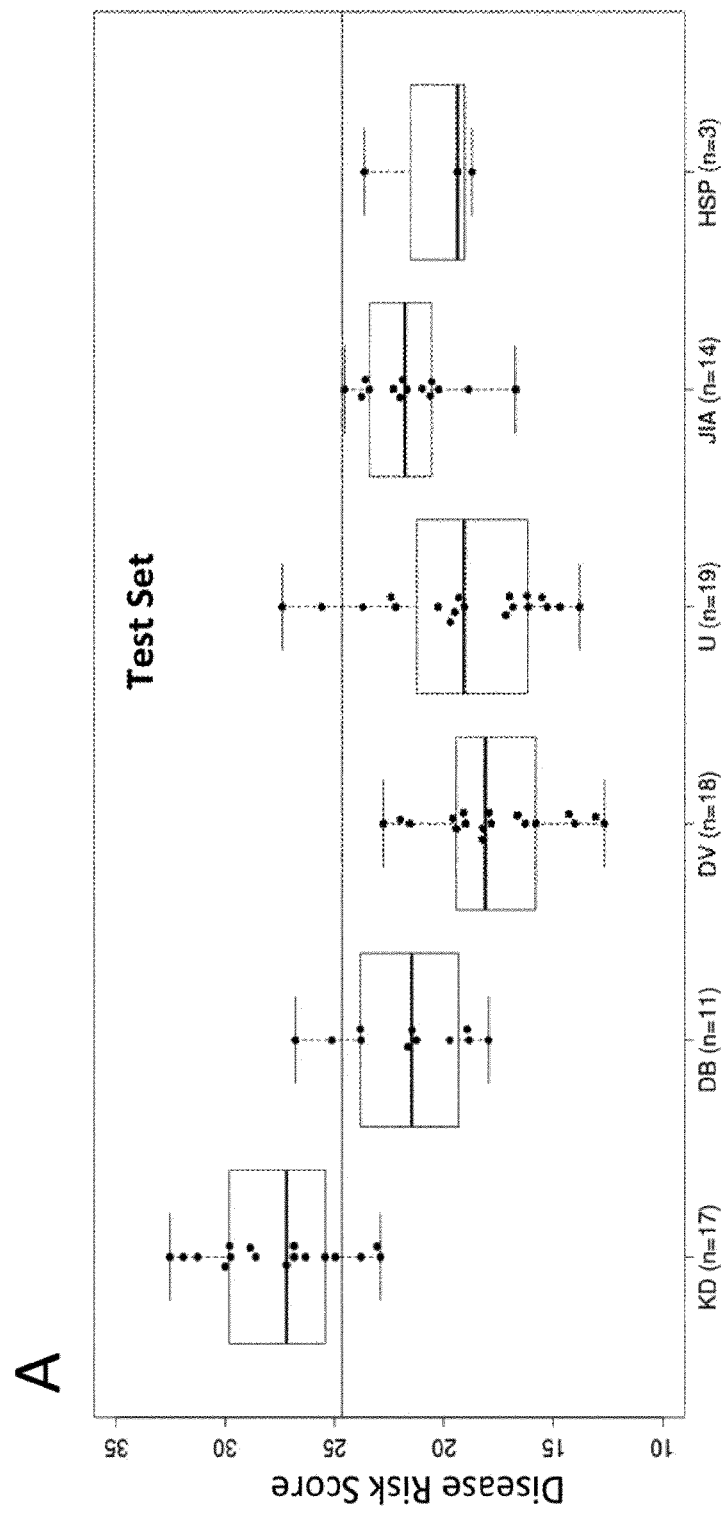
Fig 3A Performance of the 13-transcript signature on the discovery test and validation sets Fig 3B Performance of the 13-transcript signature on the discovery test and validation sets
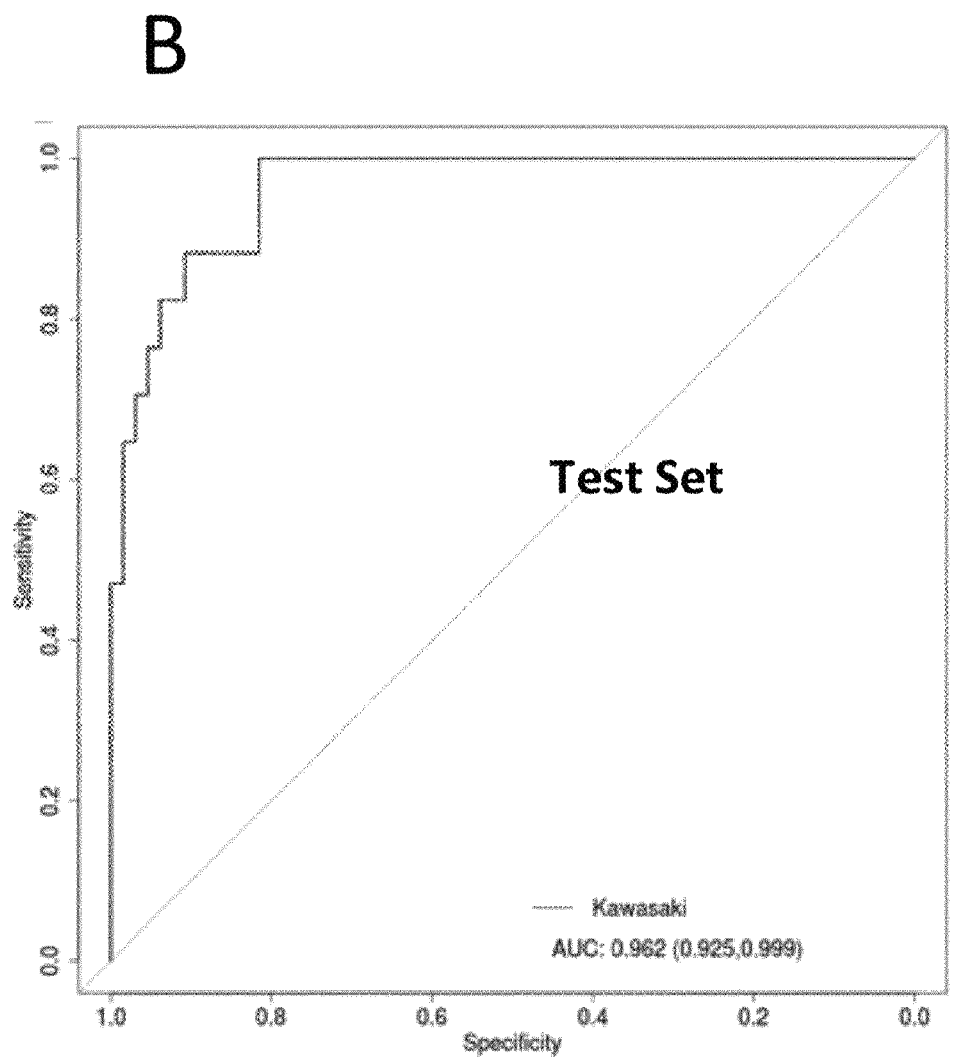

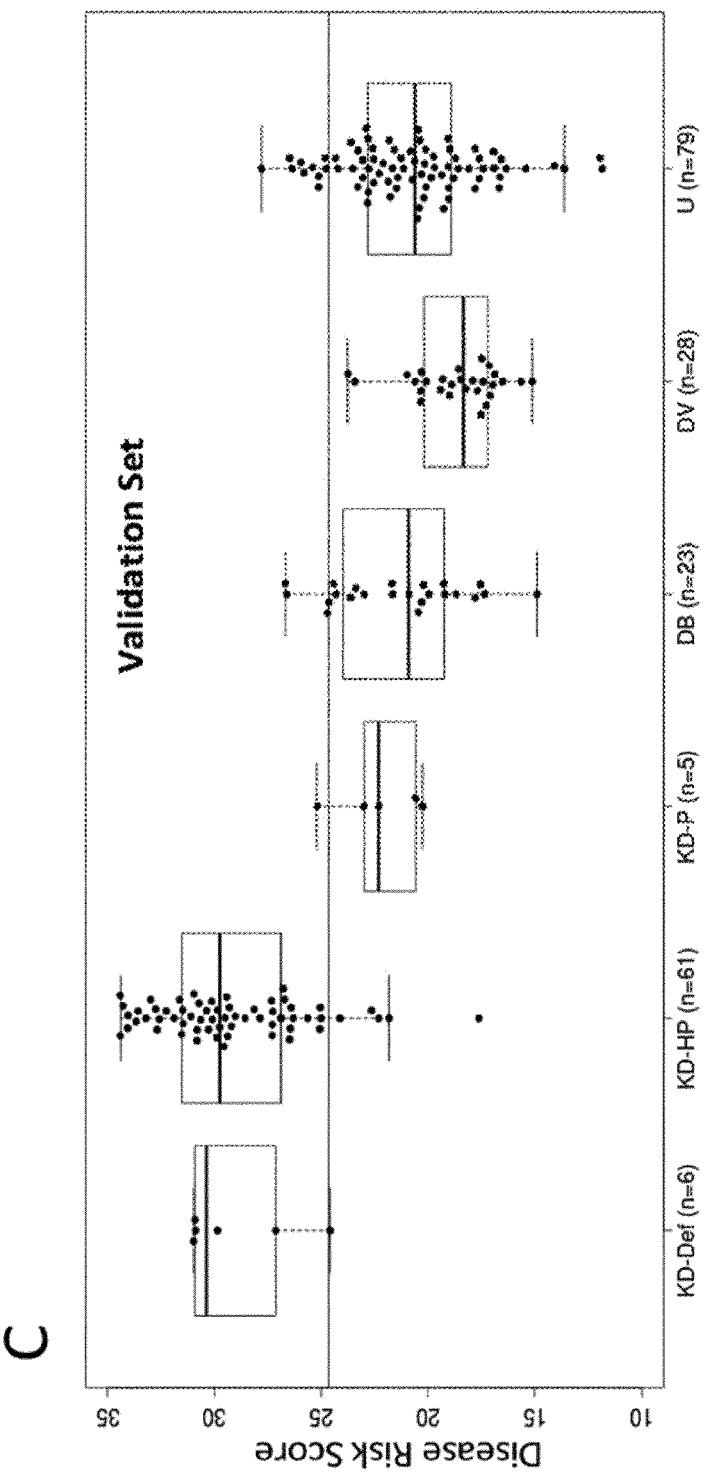
Fig 3C Performance of the 13-transcript signature on the discovery test and validation sets Fig 3D Performance of the 13-transcript signature on the discovery test and validation sets
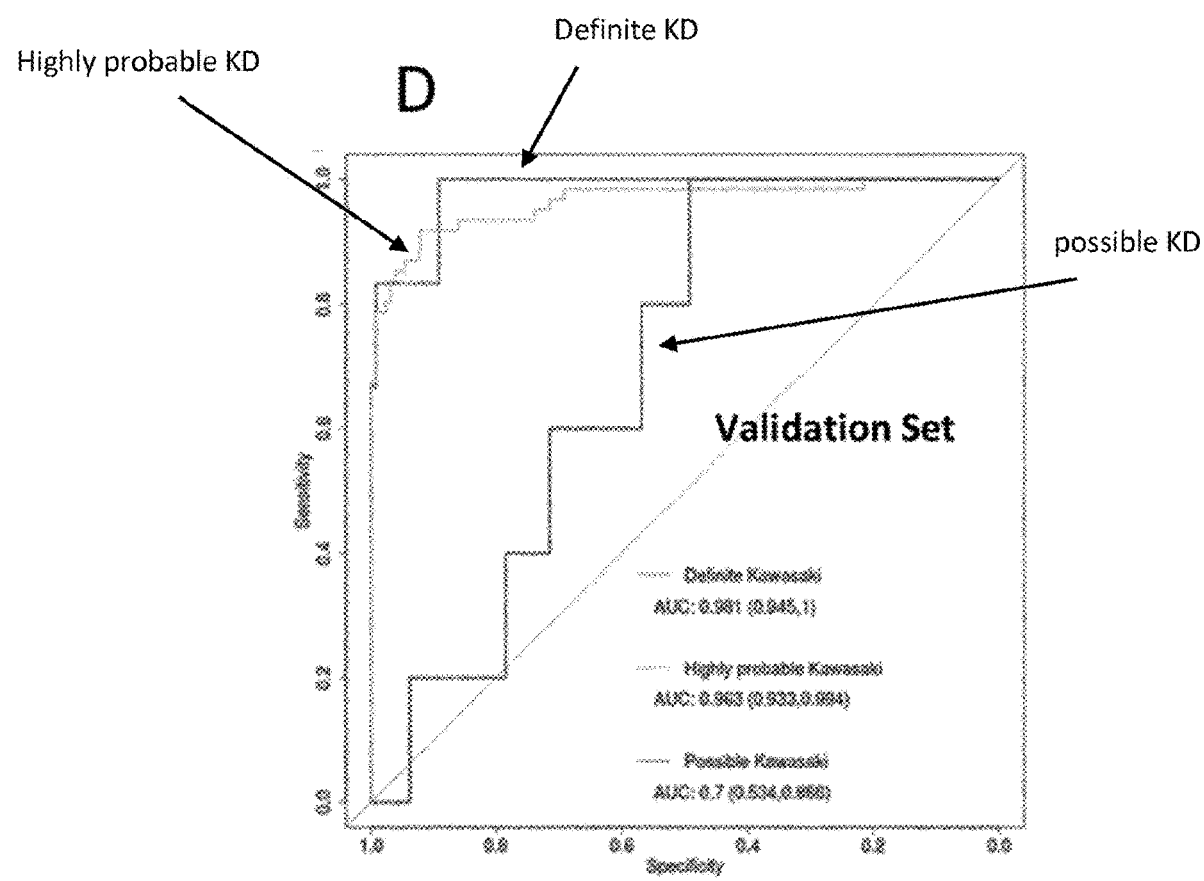

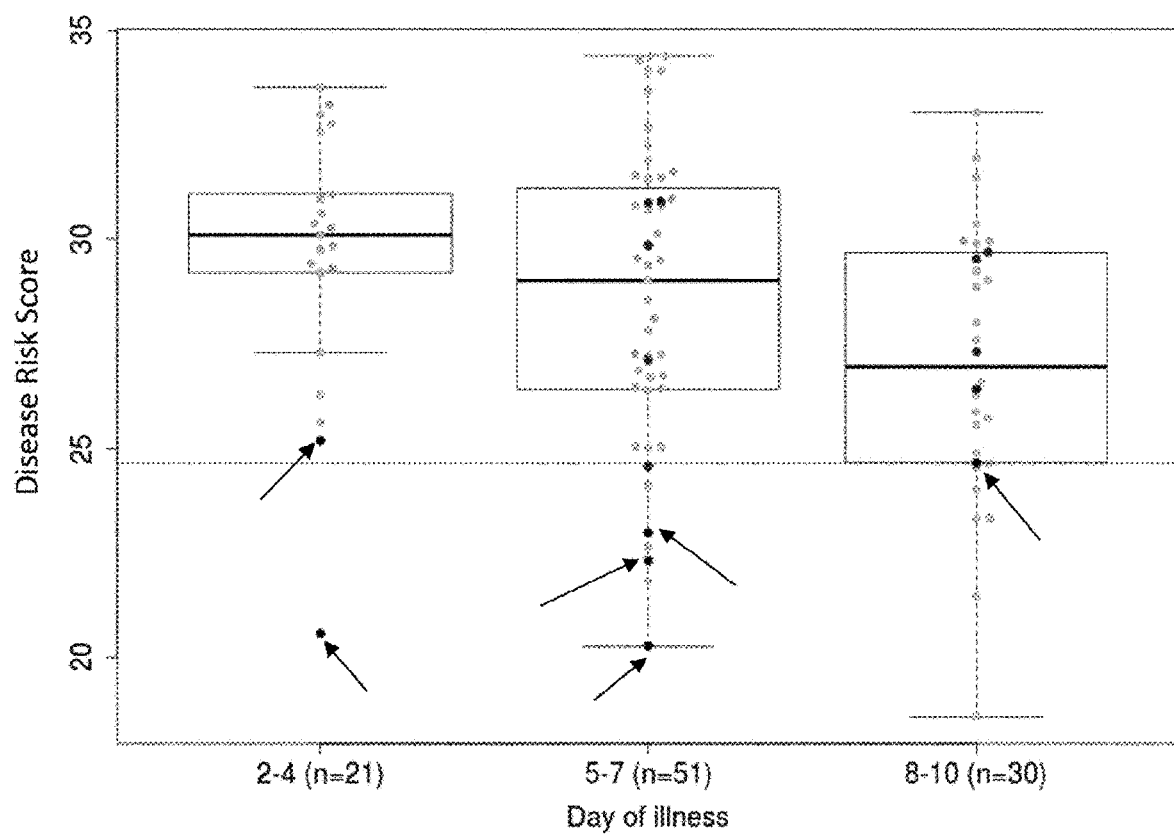
Fig 4. Performance of the 13-transcript signature by illness day at sample collection in validation set Figure 5: Principal component analysis on the discovery cohort
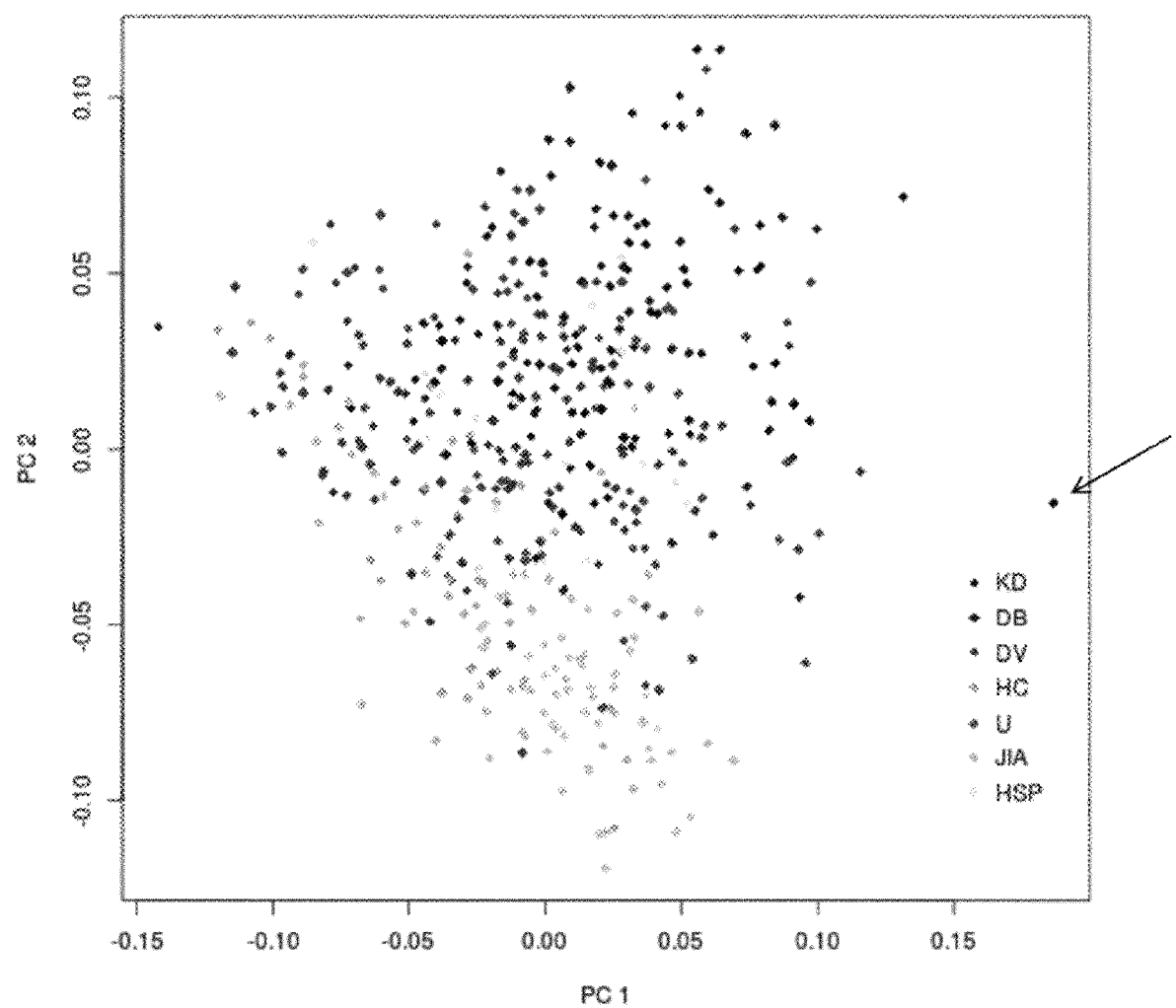

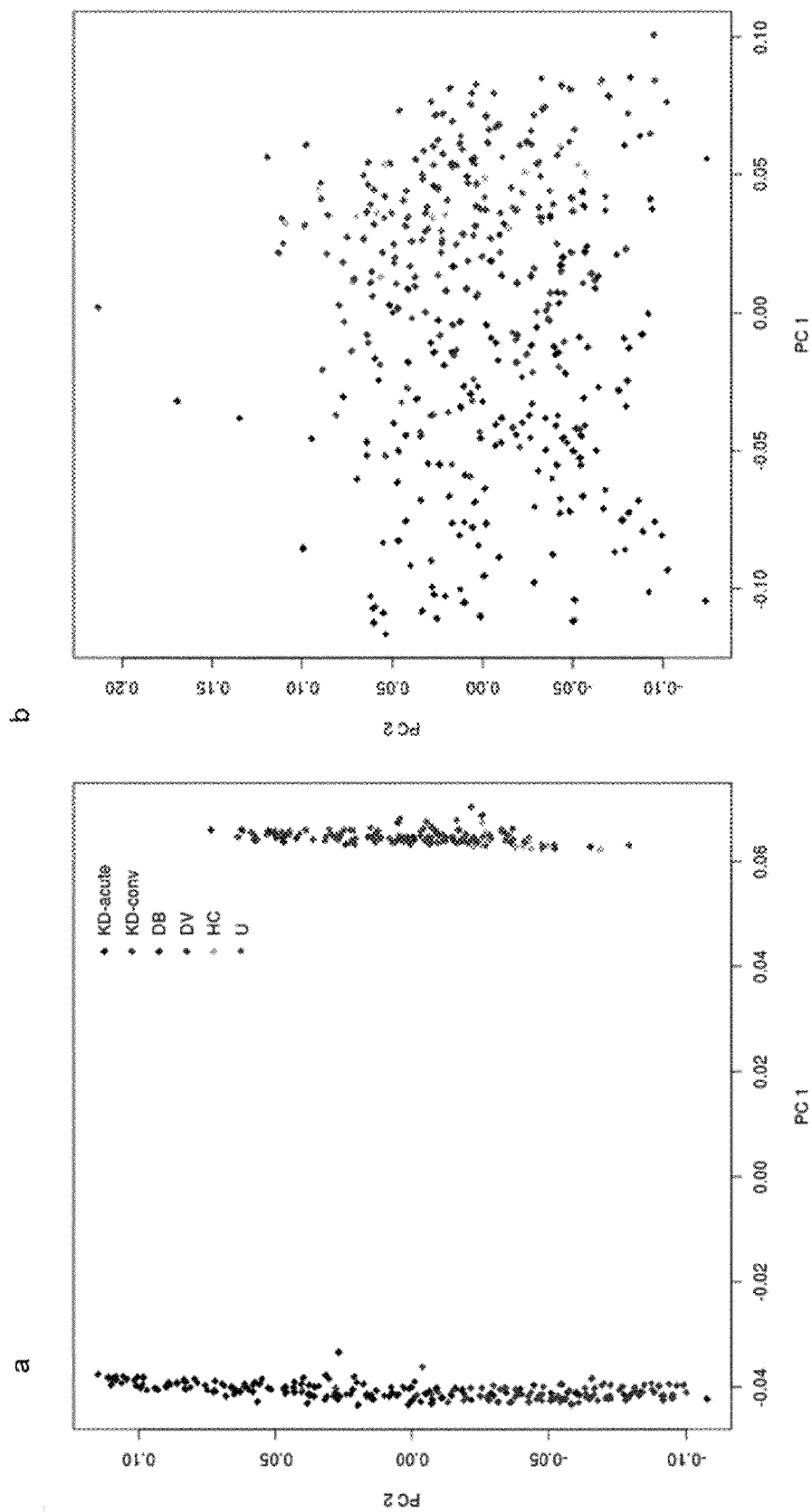
Figure 6: Principal component analysis on validation sets before and after merging using ComBat

METHOD OF IDENTIFYING A SUBJECT HAVING KAWASAKI DISEASE

CROSS-REFERENCE TO RELATED APPLICATIONS

This application is a 371 National Phase of International Patent Application No. PCT/EP2019/071052 filed Aug. 5, 2019, which claims priority to Application No. GB 1812712.6 filed on Aug. 4, 2018 and GB Application No. 1814112.7 filed on Aug. 30, 2018, the content of each of which applications is incorporated herein by reference.

The present disclosure relates to a method of identifying a subject having Kawasaki disease (KD), which includes discriminating the subject from a subject having another condition, for example other infectious and inflammatory conditions, such as those that present similar symptoms to KD. The disclosure also relates to a minimal gene signature employed in the said method and to a bespoke gene chip for use in the method. The disclosure further extends to probes and/or primers specific to genes in a signature of the present disclosure. The disclosure further relates to use of known gene chips in the methods of the disclosure and kits comprising the elements required for performing the method. The disclosure also relates to use of the method to provide a composite expression score which can be used in the discrimination of a bacterial infection from a viral infection or inflammatory disease, particularly suitable for use in a low resource setting.

BACKGROUND

Kawasaki disease (KD) is an acute inflammatory disorder predominantly affecting young children. Since its initial description in Japan [1], the disease has emerged as the most common cause of acquired heart disease with an incidence in children under five ranging from 265/100,000 in Japan [2], 51-194/100,000 in other Asian countries [3-5], and 8-20/100,000 in Europe [6] and the USA [7] respectively. What has made KD of such concern is its association with vasculitis, affecting predominantly the coronary arteries, which results in coronary artery aneurysm (CAA) formation in up to 25% of untreated children [8]. Death from myocardial infarction may occur due to thrombotic occlusion of the aneurysms, or from the later development of stenotic lesions due to vascular remodelling in the damaged artery. Long-term outcome studies of children with giant CAA indicate a worrying prognosis with over 50% needing revascularization or suffering myocardial infarction within a 30-year period [9, 10].

Treatment with intravenous immunoglobulin (IVIG) and, for those who do not respond, the administration of additional IVIG [11] or other anti-inflammatory agents such as steroids and infliximab, is effective in abrogating the inflammatory process and reduces the risk of CAA to 5-10% [12]. As KD is difficult to distinguish from other common febrile conditions, many children with KD are not diagnosed and treated early enough in the course of the illness to prevent development of CAA [13]. Furthermore, patients who do not fulfil the clinical criteria for diagnosing KD (so called "incomplete KD") may nonetheless suffer CAA. Delayed diagnosis is a consistent risk factor for development of CAA, and even in centres with considerable experience with KD, treatment is often commenced only when coronary dilatation is already demonstrated on echocardiography. CAA development is clinically silent and may be recognised only years later at the time of sudden death or myocardial infarction.

The symptoms of KD are similar to those of several other childhood febrile illnesses, including staphylococcal and streptococcal toxic shock syndromes, measles and other viral illnesses such as adenovirus infection, Rocky Mountain spotted fever, and childhood inflammatory diseases, leading to diagnostic difficulty and thus delay in diagnosis and treatment. Guidelines have been developed to facilitate clinical diagnosis based on clinical signs and symptoms, echocardiography, and laboratory parameters [14]. However, there is no definitive diagnostic test for the disease. As the global incidence of KD is increasing, there is an urgent need for an accurate test to distinguish KD from other conditions causing prolonged fever in children.

SUMMARY OF THE INVENTION

In the era of precision medicine, diagnosis of many conditions previously based on clinical features alone is being replaced by diagnosis based on molecular pathology. Host blood gene expression signatures have been shown to distinguish a number of specific infectious and inflammatory diseases including tuberculosis [15], bacterial and viral infections [16], and systemic lupus erythematosus [17]. Support for a diagnostic approach for KD based on gene expression signatures comes from identification of microRNA biomarkers in KD [18, 19], though existing studies are limited by the range of comparator patient groups, or by the need to extract RNA from exosomes.

Accordingly, the present inventors have explored the use of whole blood gene expression patterns to distinguish KD from other childhood infectious and inflammatory conditions. The present disclosure provides a gene expression signature, discovered and validated in independent patient groups, that distinguishes KD from a range of bacterial, viral and inflammatory illnesses.

The present disclosure is summarised in the following paragraphs:

1. A method of identifying a subject having Kawasaki disease (KD) comprising detecting in a subject derived RNA sample the modulation in gene expression levels of a gene signature comprising at least 5 of the following genes: CACNA1E, DDIAS, KLHL2, PYROXD2, SMOX, ZNF185, LINC02035, CLIC3, S100P, IFI27, HS.553068, CD163, and RTN1.
2. The method according to paragraph 1, wherein the gene signature comprises 6, 7, 8, 9, 10, 11, 12 or 13 of the genes.
3. The method according to paragraphs 1 or 2, wherein the gene signature comprises at least one of the following genes: PYROXD2, SMOX, CACNA1E, CD163, DDIAS, CLIC3, KLHL2 and HS.553068, in particular at least one of PYROXD2, SMOX, CACNA1E and CD163.
4. The method according to any one of paragraphs 1 to 3, wherein the gene signature comprises PYROXD2.
5. The method according to any one of paragraphs 1 to 4, wherein the gene signature comprises CACNA1E.
6. The method according to any one of paragraphs 1 to 5, wherein the gene signature comprises SMOX.
7. The method according to any one of paragraphs 1 to 6, wherein the gene signature comprises CD163.

8. The method according to any one of paragraphs 1 to 7, wherein the gene signature comprises:
   (i) PYROXD2 and CACNA1E;
   (ii) PYROXD2 and SMOX; or
   (iii) PYROXD2, CACNA1E and SMOX.
9. The method according to any one of paragraphs 1 to 8, wherein the gene signature comprises or consists of at least 5 of the genes, for example selected from:
   (i) PYROXD2, CACNA1E, CD163, KLHL2 and SMOX;
   (ii) PYROXD2, CACNA1E, IFI27, KLHL2 and SMOX;
   (iii) PYROXD2, CACNA1E, HS.553068, IFI27 and SMOX;
   (iv) PYROXD2, DDIAS, CACNA1E, IFI27 and SMOX; (v) PYROXD2, CACNA1E, CD163, KLHL2 and ZNF185; or
   (vi) PYROXD2, DDIAS, CD163, KLHL2 and SMOX.
10. The method according to any one of paragraphs 1 to 8, wherein the gene signature comprises or consists of at least 6 of the genes, for example selected from:
   (i) PYROXD2, CACNA1E, CD163, IFI27, KLHL2 and SMOX;
   (ii) PYROXD2, CACNA1E, CD163, KLHL2, LINC02035 and SMOX;
   (iii) PYROXD2, DDIAS, CACNA1E, CD163, IFI27 and SMOX;
   (iv) PYROXD2, CACNA1E, CD163, HS.553068, IFI27 and SMOX;
   (v) PYROXD2, CACNA1E, CD163, KLHL2, SMOX and ZNF185;
   (vi) PYROXD2, CACNA1E, IFI27, KLHL2, RTN1 and SMOX;
   (vii) PYROXD2, CACNA1E, CD163, CLIC3, KLHL2 and SMOX;
   (viii) PYROXD2, CACNA1E, CLIC3, IFI27, KLHL2 and SMOX;
   (ix) PYROXD2, DDIAS, CACNA1E, IFI27, RTN1 and SMOX; or
   (x) PYROXD2, DDIAS, CD163, IFI27, KLHL2 and SMOX.
11. The method according to any one of paragraphs 1 to 8, wherein the gene signature comprises or consists of at least 7 of the genes, for example selected from:
   (i) PYROXD2, CACNA1E, CD163, HS.553068, IFI27, KLHL2 and SMOX;
   (ii) PYROXD2, CACNA1E, CD163, CLIC3, IFI27, KLHL2 and SMOX;
   (iii) PYROXD2, DDIAS, CACNA1E, CD163, IFI27, KLHL2 and SMOX;
   (iv) PYROXD2, CACNA1E, CD163, IFI27, KLHL2, RTN1 and SMOX; or
   (v) PYROXD2, DDIAS, CACNA1E, CD163, HS.553068, IFI27 and SMOX.
12. The method according to any one of paragraphs 1 to 8, wherein the gene signature comprises or consists of at least 8 of the genes, for example selected from:
   (i) PYROXD2, DDIAS, CACNA1E, CD163, CLIC3, IFI27, KLHL2 and SMOX;
   (ii) PYROXD2, CACNA1E, CD163, CLIC3, HS.553068, IFI27, KLHL2 and SMOX;
   (iii) PYROXD2, CACNA1E, CD163, CLIC3, IFI27, KLHL2, RTN1 and SMOX; or
   (iv) PYROXD2, CACNA1E, CD163, HS.553068, IFI27, KLHL2, S100P and SMOX.
13. The method according to any one of paragraphs 1 to 8, wherein the gene signature comprises or consists of at least 9 of the genes, for example selected from:
   (i) PYROXD2, DDIAS, CACNA1E, CD163, CLIC3, HS.553068, IFI27, KLHL2 and SMOX;
   (ii) PYROXD2, DDIAS, CACNA1E, CD163, CLIC3, IFI27, KLHL2, RTN1 and SMOX; or
   (iii) PYROXD2, CACNA1E, CD163, CLIC3, HS.553068, IFI27, KLHL2, RTN1 and SMOX.
14. The method according to any one of paragraphs 1 to 8, wherein the gene signature comprises or consists of at least 10 of the genes, for example selected from:
   (i) PYROXD2, DDIAS, CACNA1E, CD163, CLIC3, IFI27, KLHL2, RTN1, S100P and SMOX; or
   (ii) PYROXD2, DDIAS, CACNA1E, CD163, CLIC3, HS.553068, IFI27, KLHL2, RTN1 and SMOX.
15. The method according to any one of paragraphs 1 to 8, wherein the gene signature comprises or consists of at least 11 of the genes, for example selected from:
   (i) PYROXD2, DDIAS, CACNA1E, CD163, CLIC3, HS.553068, IFI27, KLHL2, RTN1, S100P and SMOX;
   (ii) PYROXD2, DDIAS, CACNA1E, CD163, CLIC3, IFI27, KLHL2, LINC02035, RTN1, S100P and SMOX; or
   (iii) PYROXD2, DDIAS, CACNA1E, CD163, CLIC3, IFI27, KLHL2, RTN1, S100P, SMOX and ZNF185.
16. The method according to any one of paragraphs 1 to 8, wherein the gene signature comprises or consists of at least 12 of the genes, for example selected from:
   (i) PYROXD2, DDIAS, CACNA1E, CD163, CLIC3, HS.553068, IFI27, KLHL2, RTN1, S100P, SMOX and ZNF185;
   (ii) PYROXD2, DDIAS, CACNA1E, CD163, CLIC3, HS.553068, IFI27, KLHL2, LINC02035, RTN1, S100P and SMOX; or
   (iii) PYROXD2, DDIAS, CACNA1E, CD163, CLIC3, IFI27, KLHL2, LINC02035, RTN1, S100P, SMOX and ZNF185.
17. The method according to any one of paragraphs 1 to 8, wherein the gene signature comprises or consists of CACNA1E, DDIAS, KLHL2, PYROXD2, SMOX, ZNF185, LINC02035, CLIC3, S100P, IFI27, HS.553068, CD163, and RTN1.
18. The method according to any one of paragraphs 1 to 17, wherein the method further incorporates detecting the expression levels or one or more housekeeping genes, such as 1, 2, 3, 4 or 5 housekeeping genes, for example selected from actin, GAPDH, ubiquitin, 18s rRNA, RPII (POLR2A), TBP, PPIA, GUSB, HSPCB, YWHAZ, SDHA, RPS13, HPRT1 and B4GALT6.
19. The method according to any one of paragraphs 1 to 18, wherein a subject with KD can be identified in the presence of one or more of the following: a bacterial infection, a viral infection and an inflammatory condition.
20. The method according to any one of paragraphs 1 to 19, wherein a subject with KD can be discriminated from a patient with one or more of the following: a bacterial infection, a viral infection and an inflammatory condition.
21. The method according to paragraphs 19 or 20, wherein the bacterial infection is selected from the group consisting of: *Chlamydia pneumoniae, Chlamydia trachomatis, Chlamydophila psittaci, Mycoplasma pneumonia, Corynebacterium diphtheriae, Clostridium botulinum, Clostridium difficile, Clostridium perfrin-* gens, *Clostridium tetani, Enterococcus faecalis, Enterococcus faecium, Listeria monocytogenes, Staphylococcus aureus, Staphylococcus epidermidis, Staphylococcus saprophyticus,* Group B *streptococcus, Streptococcus agalactiae, Streptococcus pneumoniae, Streptococcus pyogenes,* or acid fast bacteria such as *Mycobacterium leprae, Mycobaterium tuberculosis, Mycobacterium ulcerans, Mycobacterium avium intercellularae, Bordetella pertussis, Borrelia burgdorferi, Brucella abortus, Brucella canis, Brucella melitensis, Brucella suis, Campylobacter jejuni, Escherichia coli, Francisella tularensis, Haemophilus influenzae, Helicobacter pylori, Legionella pneumophila, Leptospira interrogans, Neisseria gonorrhoeae, Neisseria meningitidis, Pseudomonas aeruginosa, Pseudomonas* spp, *Rickettsia rickettsii, Salmonella typhi, Salmonella typhimurium, Shigella sonnei, Treponema pallidum, Vibrio cholerae, Yersinia pestis, Kingella kingae, Stenotrophomonas, Klebsiella,* a gram-positive coccus, a gram-negative *bacillus, mycoplasma,* pertussis, mycobacteria and staphylococcal and streptococcal toxic shock syndromes, for example a gram-positive coccus, a gram-negative *bacillus, mycoplasma* or pertussis, and mycobacteria, in particular selected from the group consisting of *S. pneumoniae, S. aureus, S. pyogenes,* Group B *streptococcus, E. coli, N. meningitidis, Enterococcus, Kingella, H. influenzae, Pseudomonas* spp, *Stenotrophomonas, Klebsiella,* staphylococcal and streptococcal toxic shock syndrome, in particular staphylococcal or streptococcal toxic shock syndrome.

22. The method according to any one of paragraphs 19 to 21, wherein viral infection is selected from the group consisting of: selected from the group consisting of: Influenza such as Influenza A, including but not limited to: H1N1, H2N2, H3N2, H5N1, H7N7, H1N2, H9N2, H7N2, H7N3, H10N7, Influenza B and Influenza C, Respiratory Syncytial Virus (RSV), rhinovirus, enterovirus, bocavirus, parainfluenza (such as parainfluenza 1-4), adenovirus, metapneumovirus, herpes simplex virus, Chickenpox virus, Human papillomavirus, Hepatitis, Epstein-Barr virus, Varicella-zoster virus, Human cytomegalovirus, Human herpesvirus, type 8 BK virus, JC virus, Smallpox, Parvovirus B19, Human astrovirus, Norwalk virus, coxsackievirus, poliovirus, Severe acute respiratory syndrome virus, yellow fever virus, dengue virus, West Nile virus, Rubella virus, Human immunodeficiency virus, Guanarito virus, Junin virus, Lassa virus, Machupo virus, Sabia virus, Crimean-Congo haemorrhagic fever virus, Ebola virus, Marburg virus, Measles virus, Mumps virus, Rabies virus, Rotavirus, and Rocky Mountain spotted fever, for example selected from the group consisting of: respiratory syncytial virus (RSV), adenovirus, parainfluenza virus (such as parainfluenza 1-4), influenza (such as influenza A, B or A+B), bocavirus, metapneumovirus, rhinovirus and enterovirus, in particular RSV, influenza A/B and adenovirus, in particular measles, an adenovirus infection and Rocky Mountain spotted fever.

23. The method according to any one of paragraphs 19 to 22, wherein the inflammatory condition is selected from the group consisting of asthma, peptic ulcers, tuberculosis, periodontitis, ulcerative colitis, Crohn's disease, sinusitis, hepatitis, multiple sclerosis, atherosclerosis, sjogrens disease, inflammatory bowel disease, lupus erythrematosus (including systemic lupus erythrematosus), fibrotic diseases, such as pulmonary fibrosis, Henoch-Schonlein Purpura (HSP) and Juvenile Idiopathic Arthritis (JIA), in particular Henoch-Schonlein Purpura (HSP) or Juvenile Idiopathic Arthritis (JIA).

24. The method according to any one of paragraphs 1 to 23, wherein the subject is a child, for example where the child is in the age range 2 to 59 months.

25. The method according to any one of paragraphs 1 to 23, wherein the subject is an infant in the age range 0 to 59 days.

26. The method according to any one of paragraphs 1 to 25, wherein the subject has a fever.

27. The method according to any one of paragraphs 1 to 26, wherein the analysis of gene expression modulation employs a microarray or a gene chip.

28. The method according to any one of paragraphs 1 to 27, wherein the analysis gene expression modulation employs: PCR, such as RT-PCR, in particular a multiplex PCR.

29. The method according to paragraph 14 or 15, wherein the PCR is quantitative.

30. The method according to any one of paragraphs 28 to 29, wherein primers employed in the PCR comprise a label or a combination of labels, for example wherein the label is fluorescent or coloured, for example coloured beads.

31. The method according to any one of paragraphs 1 to 30, which comprises the further step of prescribing or administering a treatment for Kawasaki disease (KD) to the subject based on the results of the analysis of the gene signature.

32. A method of treating a subject having Kawasaki disease (KD), comprising administering a treatment for KD to the subject, wherein the subject has been previously identified as having Kawasaki disease by detecting in a subject derived RNA sample the modulation in gene expression levels of a gene signature comprising at least 5 of the following genes: CACNA1E, DDIAS, KLHL2, PYROXD2, SMOX, ZNF185, LINC02035, CLIC3, S100P, IFI27, HS.553068, CD163, and RTN1.

33. The method according to paragraphs 31 or 32, wherein the treatment is gamma globulin (IVIg), aspirin, or other anti-inflammatory agents, such as steroids and infliximab, or a combination thereof.

34. A set of primers for use in a method of identifying a subject having Kawasaki disease (KD) comprising primers specific to a polynucleotide gene transcript from at least 5 of the following genes: CACNA1E, DDIAS, KLHL2, PYROXD2, SMOX, ZNF185, LINC02035, CLIC3, S100P, IFI27, HS.553068, CD163, and RTN1.

35. The set of primers according to paragraph 34, consisting of primers that are only specific to the following genes: CACNA1E, DDIAS, KLHL2, PYROXD2, SMOX, ZNF185, LINC02035, CLIC3, S100P, IFI27, HS.553068, CD163, and RTN1.

36. A gene chip consisting of probes that are specific to at least 5 of the following genes: CACNA1E, DDIAS, KLHL2, PYROXD2, SMOX, ZNF185, LINC02035, CLIC3, S100P, IFI27, HS.553068, CD163, and RTN1.

37. A gene chip consisting of probes that are specific to at least 5 of the following genes: CACNA1E, DDIAS, KLHL2, PYROXD2, SMOX, ZNF185, LINC02035, CLIC3, S100P, IFI27, HS.553068, CD163, and RTN1; and one or more control probes.

38. The gene chip according to paragraph 37, wherein the one or more control probes are specific to a gene selected from the group consisting of actin, GAPDH, ubiquitin, 18s rRNA, RPII (POLR2A), TBP, PPIA, GUSB, HSPCB, YWHAZ, SDHA, RPS13, HPRT1 and B4GALT6.

39. A point of care test for identifying a subject having Kawasaki disease (KD) t comprising the set of primers defined in paragraphs 34 or 35 or the gene chip according to any one of paragraphs 36 to 38.

40. Use of the set of primers defined in paragraphs 34 or 35 or the gene chip according to any one of paragraphs 36 to 38 in an assay to detect Kawasaki disease (KD) in a sample, for example a blood sample.

The present disclosure provides a method of identifying a subject having Kawasaki disease (KD) comprising detecting the expression levels of at least 5 of the following genes: CACNA1E, DDIAS (C11ORF82), KLHL2, PYROXD2 (C100RF33), SMOX, ZNF185, LINC02035 (LOC100129550), CLIC3, S100P, IFI27, HS.553068, CD163, and RTN1.

Therefore, in one aspect, there is a method of identifying a subject having Kawasaki disease (KD) comprising detecting in a subject derived RNA sample the modulation in gene expression levels of a gene signature comprising at least 5 of the following genes: CACNA1E, DDIAS (C11ORF82), KLHL2, PYROXD2 (C100RF33), SMOX, ZNF185, LINC02035 (LOC100129550), CLIC3, S100P, IFI27, HS.553068, CD163, and RTN1.

Advantageously, use of the gene signature in a method according to the present disclosure allows the robust and accurate identification of a subject having KD. Importantly, the method allows the accurate discrimination between patients having KD from those displaying similar symptoms but have other bacterial infections, viral infections and/or inflammatory conditions. In other words, the method allows the accurate detection of KD in the presence or absence of bacterial, viral infections and/or inflammatory conditions, without the need to rely on clinical criteria and/or laboratory tests such as echocardiography.

Gene signatures often comprise a large number of genes which only in combination show a pattern or marker of biological significance. It is very surprising that the gene signature of the present disclosure can be based on as few as 13 genes and still reliably identify the presence of KD.

A gene signature of the present disclosure comprising at least 5 of the above mentioned 13 genes provides good predictive power. However, additional genes can be included in the signature in order to further augment and increase the discriminatory power of the gene signature. Thus, in one embodiment, the signature comprises at least 5, 6, 7, 8, 9, 10, 11, 12 or 13 of the genes.

Thus, in one embodiment, the signature comprises at least PYROXD2. In one embodiment, the signature comprises at least SMOX. In one embodiment, the signature comprises at least CACNA1E. In one embodiment, the signature comprises at least CD163. In one embodiment, the signature comprises at least DDIAS. In one embodiment, the signature comprises at least CLIC3. In one embodiment, the signature comprises at least KLHL2. In another embodiment, the signature comprises at least HS.553068. In another embodiment, the signature comprises at least RTN1. In another embodiment, the signature comprises at least ZNF185. In another embodiment, the signature comprises at least IFI27. In another embodiment, the signature comprises at least S100P. In another embodiment, the signature comprises at least LINC02035.

In one embodiment, the gene signature comprises at least one of the following genes: PYROXD2, SMOX, CACNA1E, CD163, DDIAS, CLIC3, KLHL2 and HS.553068. In another embodiment, the gene signature comprises at least one of the following genes: PYROXD2, SMOX, CACNA1E and CD163. The present inventors have discovered that these particular genes have higher discriminatory power and are therefore more likely to be present in the signatures with the best predictive capabilities.

For example, the gene signature may comprise any of the following combinations of genes: PYROXD2, SMOX, CACNA1E and CD163; PYROXD2, SMOX and CACNA1E; PYROXD2, SMOX and CD163; SMOX, CACNA1E and CD163; PYROXD2, CACNA1E and CD163; PYROXD2 and SMOX; PYROXD2 and CACNA1E; PYROXD2 and CD163; SMOX and CACNA1E; SMOX and CD163; or CACNA1E and CD163; or any other combination.

In one embodiment, the signature comprises PYROXD2 and at least one of CACNA1E and SMOX. Therefore, in one embodiment, the signature comprises PYROXD2 and CACNA1E. In another embodiment, the signature comprises PYROXD2 and SMOX. In yet another embodiment, the signature comprises PYROXD2, CACNA1E and SMOX.

In one embodiment, the signature comprises at least 5 of the 13 genes. Thus, in one embodiment, the signature comprises or consists of PYROXD2, CACNA1E, CD163, KLHL2 and SMOX. In one embodiment, the signature comprises or consists of PYROXD2, CACNA1E, IFI27, KLHL2 and SMOX. In one embodiment, the signature comprises or consists of PYROXD2, CACNA1E, HS.553068, IFI27 and SMOX. In one embodiment, the signature comprises or consists of PYROXD2, DDIAS, CACNA1E, IFI27 and SMOX. In one embodiment, the signature comprises or consists of PYROXD2, CACNA1E, CD163, KLHL2 and ZNF185. In one embodiment, the signature comprises or consists of PYROXD2, DDIAS, CD163, KLHL2 and SMOX.

In one embodiment, the signature comprises at least 6 of the 13 genes. Thus, in one embodiment, the signature comprises or consists of PYROXD2, CACNA1E, CD163, IFI27, KLHL2 and SMOX. In one embodiment, the signature comprises or consists of PYROXD2, CACNA1E, CD163, KLHL2, LINC02035 and SMOX. In one embodiment, the signature comprises or consists of PYROXD2, DDIAS, CACNA1E, CD163, IFI27 and SMOX. In one embodiment, the signature comprises or consists of PYROXD2, CACNA1E, CD163, HS.553068, IFI27 and SMOX. In one embodiment, the signature comprises or consists of PYROXD2, CACNA1E, CD163, KLHL2, SMOX and ZNF185. In one embodiment, the signature comprises or consists of PYROXD2, CACNA1E, IFI27, KLHL2, RTN1 and SMOX. In one embodiment, the signature comprises or consists of PYROXD2, CACNA1E, CD163, CLIC3, KLHL2 and SMOX. In one embodiment, the signature comprises or consists of PYROXD2, CACNA1E, CLIC3, IFI27, KLHL2 and SMOX. In one embodiment, the signature comprises or consists of PYROXD2, DDIAS, CACNA1E, IFI27, RTN1 and SMOX. In one embodiment, the signature comprises or consists of PYROXD2, DDIAS, CD163, IFI27, KLHL2 and SMOX.

In one embodiment, the signature comprises at least 7 of the 13 genes. Thus, in one embodiment, the signature comprises or consists of PYROXD2, CACNA1E, CD163, HS.553068, IFI27, KLHL2 and SMOX. In one embodiment, the signature comprises or consists of PYROXD2, CACNA1E, CD163, CLIC3, IFI27, KLHL2 and SMOX. In one embodiment, the signature comprises of consists of PYROXD2, DDIAS, CACNA1E, CD163, IFI27, KLHL2 and SMOX. In one embodiment, the signature comprises of consists of PYROXD2, CACNA1E, CD163, IFI27, KLHL2, RTN1 and SMOX. In one embodiment, the signature comprises of consists of PYROXD2, DDIAS, CACNA1E, CD163, HS.553068, IFI27 and SMOX.

In another embodiment, the signature comprises at least 8 of the 13 genes. Thus, in one embodiment, the signature comprises or consists of PYROXD2, DDIAS, CACNA1E, CD163, CLIC3, IFI27, KLHL2 and SMOX. In another embodiment, the signature comprises or consists of PYROXD2, CACNA1E, CD163, CLIC3, HS.553068, IFI27, KLHL2 and SMOX. In one embodiment, the signature comprises or consists of PYROXD2, CACNA1E, CD163, CLIC3, IFI27, KLHL2, RTN1 and SMOX. In one embodiment, the signature comprises or consists of PYROXD2, CACNA1E, CD163, HS.553068, IFI27, KLHL2, S100P and SMOX.

In another embodiment, the signature comprises at least 9 of the 13 genes. Thus, in one embodiment, the signature comprises or consists of PYROXD2, DDIAS, CACNA1E, CD163, CLIC3, HS.553068, IFI27, KLHL2 and SMOX. In one embodiment, the signature comprises or consists of PYROXD2, DDIAS, CACNA1E, CD163, CLIC3, IFI27, KLHL2, RTN1 and SMOX. In one embodiment, the signature comprises or consists of PYROXD2, CACNA1E, CD163, CLIC3, HS.553068, IFI27, KLHL2, RTN1 and SMOX.

In another embodiment, the signature comprises at least 10 of the 13 genes. Thus, in one embodiment, the signature comprises or consists of PYROXD2, DDIAS, CACNA1E, CD163, CLIC3, IFI27, KLHL2, RTN1, S100P and SMOX. In another embodiment, the signature comprises or consists of PYROXD2, DDIAS, CACNA1E, CD163, CLIC3, HS.553068, IFI27, KLHL2, RTN1 and SMOX.

In another embodiment, the signature comprises at least 11 of the 13 genes. Thus, in one embodiment, the signature comprises or consists of PYROXD2, DDIAS, CACNA1E, CD163, CLIC3, HS.553068, IFI27, KLHL2, RTN1, S100P and SMOX. In another embodiment, the signature comprises or consists of PYROXD2, DDIAS, CACNA1E, CD163, CLIC3, IFI27, KLHL2, LINC02035, RTN1, S100P and SMOX. In another embodiment, the signature comprises or consists of PYROXD2, DDIAS, CACNA1E, CD163, CLIC3, IFI27, KLHL2, RTN1, S100P, SMOX and ZNF185.

In one embodiment, the signature comprises at least 12 of the 13 genes. Thus, in one embodiment, the signature comprises or consists of PYROXD2, DDIAS, CACNA1E, CD163, CLIC3, HS.553068, IFI27, KLHL2, RTN1, S100P, SMOX and ZNF185. In another embodiment, the signature comprises or consists of PYROXD2, DDIAS, CACNA1E, CD163, CLIC3, HS.553068, IFI27, KLHL2, LINC02035, RTN1, S100P and SMOX. In another embodiment, the signature comprises or consists of PYROXD2, DDIAS, CACNA1E, CD163, CLIC3, IFI27, KLHL2, LINC02035, RTN1, S100P, SMOX and ZNF185.

In one embodiment, the signature comprises all 13 genes. Thus, in one embodiment, the gene signature comprises or consists of CACNA1E, DDIAS, KLHL2, PYROXD2, SMOX, ZNF185, LINC02035, CLIC3, S100P, IFI27, HS.553068, CD163, and RTN1. Advantageously, the signature comprising all 13 genes has the highest discriminatory power and allows KD to be identified with the highest degree of sensitivity and specificity.

The identification of KD can be particularly critical because of its association with vasculitis, which may result in coronary artery aneurysm (CCA) formation. Death from myocardial infarction may occur due to thrombotic occlusion of the aneurysms, or from the later development of stenotic lesions due to vascular remodelling in the damaged artery. Hence, there is a significant unmet clinical need for proper and reliable identification of KD. The gene signature of the present disclosure is a huge step forward on the road to treating patients, such as febrile patients because it allows accurate and rapid diagnosis which, in turn, allows patients to be appropriately and timely treated.

Furthermore, the components employed in the method disclosed herein can be provided in a simple format, which are cost efficient, rapid, cost effective, and can be employed in low resource and/or rural settings.

The present inventors found that the transcript expression levels of CACNA1E, DDIAS, KLHL2, PYROXD2, SMOX, ZNF185, LINC02035 and CLIC3 are increased in subjects having KD compared to subjects that do not have KD, and that the expression levels of S100P, IFI27, HS.553068, CD163, and RTN1 are decreased in subjects having KD compared to subjects that do not have KD.

Advantageously, the present inventors were able to discriminate subjects having KD from subjects that do not have KD with a high AUC of ~96.2%, and a high degree of sensitivity (~81.7%) and specificity (~92.1%) using a gene signature which detects the modulation in gene expression levels of the 13 genes listed above.

Advantageously, the gene signature was developed from a training set including a range of ethnicities. This means that the gene signature and methods of the present disclosure can be applied to samples derived from subjects of different ethnicities. Further advantageously, the gene signature was developed using KD patients that were no more than 7 days into their illness. This means that the signature can facilitate early diagnosis of KD, before 5 days of fever, which can aid in the early identification of KD patients and early appropriate treatment can be given.

Accordingly, the present inventors have demonstrated that the method is applicable across a wide range of different samples and patient groups which suggests that the method is robust and reliable.

Hence, in one aspect, the present disclosure provides a method of diagnosing a subject having Kawasaki disease comprising detecting in a subject derived RNA sample the modulation in gene expression levels of a gene signature comprising at least 5 of the following genes: CACNA1E, DDIAS (C11ORF82), KLHL2, PYROXD2 (C10ORF33), SMOX, ZNF185, LINC02035 (LOC100129550), CLIC3, S100P, IFI27, HS.553068, CD163, and RTN1.

In one embodiment, the method of diagnosis is performed in vitro.

In one embodiment the method further employs one or more housekeeping genes, such as 1, 2, 3, 4 or 5 housekeeping genes. Housekeeping genes are not considered part of the signature in the context of the present specification. In one embodiment, the housekeeping gene is selected from the group consisting of actin, GAPDH, ubiquitin, 18s rRNA, RPII (POLR2A), TBP, PPIA, GUSB, HSPCB, YWHAZ, SDHA, RPS13, HPRT1 and B4GALT6.

In one embodiment the method of the present disclosure is capable of identifying a subject with KD in the presence of bacterial infection, viral infection and/or an inflammatory condition.

In one embodiment the method of the present disclosure is capable of discriminating a subject with KD from a patient with bacterial infection, viral infection and/or inflammatory condition.

In one embodiment the bacterial infection is selected from the group consisting of: *Chlamydia pneumoniae, Chlamydia trachomatis, Chlamydophila psittaci, Mycoplasma pneumonia, Corynebacterium diphtheriae, Clostridium botulinum, Clostridium difficile, Clostridium perfringens, Clostridium tetani, Enterococcus faecalis, Enterococcus faecium, Listeria monocytogenes, Staphylococcus aureus, Staphylococcus epidermidis, Staphylococcus saprophyticus*, Group B *streptococcus, Streptococcus agalactiae, Streptococcus pneumoniae, Streptococcus pyogenes*, or acid fast bacteria such as *Mycobacterium leprae, Mycobaterium tuberculosis, Mycobacterium ulcerans, Mycobacterium avium intercellularae, Bordetella pertussis, Borrelia burgdorferi, Brucella abortus, Brucella canis, Brucella melitensis, Brucella suis, Campylobacter jejuni, Escherichia coli, Francisella tularensis, Haemophilus influenzae, Helicobacter pylori, Legionella pneumophila, Leptospira interrogans, Neisseria gonorrhoeae, Neisseria meningitidis, Pseudomonas aeruginosa, Pseudomonas spp, Rickettsia rickettsii, Salmonella typhi, Salmonella typhimurium, Shigella sonnei, Treponema pallidum, Vibrio cholerae, Yersinia pestis, Kingella kingae, Stenotrophomonas, Klebsiella*, gram-positive coccus, a gram-negative *bacillus, mycoplasma*, pertussis, mycobacteria and staphylococcal and streptococcal toxic shock syndromes, for example a gram-positive coccus, a gram-negative *bacillus, mycoplasma* or pertussis, and mycobacteria.

In one embodiment, the bacterial infection is selected from the group consisting of: *S. pneumoniae, S. aureus, S. pyogenes*, Group B *streptococcus, E. coli, N. meningitidis, Enterococcus, Kingella, H. influenzae, Pseudomonas* spp, *Stenotrophomonas* and *Klebsiella*.

In one embodiment, the bacterial infection is staphylococcal or streptococcal toxic shock syndrome.

In one embodiment the viral infection is selected from the group comprising or consisting of: Influenza such as Influenza A, including but not limited to: H1N1, H2N2, H3N2, H5N1, H7N7, H1N2, H9N2, H7N2, H7N3, H10N7, Influenza B and Influenza C, Respiratory Syncytial Virus (RSV), rhinovirus, enterovirus, bocavirus, parainfluenza, adenovirus, metapneumovirus, herpes simplex virus, Chickenpox virus, Human papillomavirus, Hepatitis, Epstein-Barr virus, Varicella-zoster virus, Human cytomegalovirus, Human herpesvirus, type 8 BK virus, JC virus, Smallpox, Parvovirus B19, Human astrovirus, Norwalk virus, coxsackievirus, poliovirus, Severe acute respiratory syndrome virus, yellow fever virus, dengue virus. West Nile virus. Rubella virus. Human immunodeficiency virus, Guanarito virus, Junin virus, Lassa virus, Machupo virus, Sabia virus, Crimean-Congo haemorrhagic fever virus, Ebola virus, Marburg virus, Measles virus, Mumps virus, Rabies virus, Rotavirus and Rocky Mountain spotted fever.

In one embodiment, the viral infection is selected from the group consisting of: respiratory syncytial virus (RSV), adenovirus, parainfluenza virus (such as parainfluenza 1-4), influenza (such as influenza A, B or A+B), bocavirus, metapneumovirus, rhinovirus and enterovirus, in particular RSV, influenza A/B and adenovirus. In one embodiment, the viral infection is selected from the group consisting of measles, an adenovirus infection and Rocky Mountain spotted fever.

The method according to any one of claims 4 to 11, wherein the inflammatory condition is selected from the group consisting of asthma, peptic ulcers, tuberculosis, periodontitis, ulcerative colitis, Crohn's disease, sinusitis, hepatitis, multiple sclerosis, atherosclerosis, sjogrens disease, inflammatory bowel disease, lupus erythematosus (including systemic lupus erythematosus), fibrotic diseases, such as pulmonary fibrosis, Henoch-Schonlein Purpura (HSP) and Juvenile Idiopathic Arthritis (JIA).

In one embodiment the inflammatory disease is disease is juvenile idiopathic arthritis (JIA), Henoch-Schönlein purpura (HSP).

In a further aspect the present disclosure provides a method of treating a subject having KD after diagnosis employing the method herein.

In one embodiment the subject is a child, for example under 17 years of age, such as 2 to 59 months old.

In one embodiment the subject is an infant, for example in the age range 0 to 59 days.

In one embodiment the subject has fever, for example is a febrile patient.

In one embodiment the method of the present disclosure is employed on a patient derived sample, for example a blood sample.

In one embodiment the analysis of gene expression modulation employs a microarray.

In one embodiment the analysis of gene expression modulation employs PCR, such as RT-PCR.

In one embodiment the PCR is multiplex PCR.

In one embodiment the PCR is quantitative.

In one embodiment the primers employed in the PCR comprise a label or a combination of labels.

In one embodiment the label is fluorescent or coloured, for example the label is coloured beads.

In one embodiment the analysis of gene expression modulation employs dual colour reverse transcriptase multiplex ligation dependent probe amplification.

In one embodiment the gene expression modulation is detected by employing fluorescence spectroscopy.

In one embodiment the gene expression modulation is detected by employing colourimetric analysis.

In one embodiment the gene expression modulation is detected employing by impedance spectroscopy.

In one embodiment the method comprises the further step of prescribing or administering a treatment for the subject having KD based on the results of the analysis of the gene signature.

Thus, in one aspect there is provided a method of treating a KD patient by administering a treatment such as gamma globulin (IVIg), aspirin, or other anti-inflammatory agents such as steroids and infliximab, wherein the patient is characterised in that the patient has been identified as positive for KD by the method disclosed herein. Hence, in one aspect, there is provided a method of treating a subject having Kawasaki disease (KD), comprising administering a treatment for KD to the subject, wherein the subject has been previously identified as having Kawasaki disease by detecting in a subject derived RNA sample the modulation in gene expression levels of a gene signature comprising at least 5 of the following genes: CACNA1E, DDIAS, KLHL2, PYROXD2, SMOX, ZNF185, LINC02035, CLIC3, S100P, IFI27, HS.553068, CD163, and RTN1. Suitable treatments for KD will be known to the skilled person, including by not limited to gamma globulin (IVIg), aspirin, or other anti-inflammatory agents, such as steroids and infliximab, or a combination thereof.

In one aspect, there is provided a method of determining whether to administer a treatment for KD, such as gamma globulin (IVIg), aspirin, or other anti-inflammatory agents such as steroids and infliximab, comprising the steps of: performing the method according to the present disclosure, and administering the KD to the subject if the method indicates that the subject has KD.

Hence, the presently disclosed method can aid in the appropriate treatment of patients, such as febrile patients, for example where it is unclear if the fever is due to Kawasaki disease or due to a bacterial infection, viral infection, inflammatory condition or a combination thereof. This has the advantage of ensuring rapid and appropriate treatment without the need to wait for laboratory test results.

In one aspect of the disclosure, there is provided a set of primers for use in multiplex PCR, wherein the set of primers include nucleic acid sequences specific to a polynucleotide gene transcript from at least 5 of the following genes: CACNA1E, DDIAS, KLHL2, PYROXD2, SMOX, ZNF185, LINC02035, CLIC3, S100P, IFI27, HS.553068, CD163, and RTN1. Thus, in one embodiment, the set of primers are specific to a transcript from at least PYROXD2. In one embodiment, the set of primers are specific to a transcript from at least SMOX. In one embodiment, the set of primers are specific to a transcript from at least CACNA1E. In one embodiment, the set of primers are specific to a transcript from at least CD163. In one embodiment, the set of primers are specific to a transcript from at least DDIAS. In one embodiment, the set of primers are specific to a transcript from at least CLIC3. In one embodiment, the set of primers are specific to a transcript from at least KLHL2. In one embodiment, the set of primers are specific to a transcript from at least HS.553068. In one embodiment, the set of primers are specific to a transcript from at least RTN1. In one embodiment, the set of primers are specific to a transcript from at least ZNF185. In one embodiment, the set of primers are specific to a transcript from at least IFI27. In one embodiment, the set of primers are specific to a transcript from at least S100P. In one embodiment, the set of primers are specific to a transcript from at least LINC02035.

In one embodiment, the set of primers are specific to a transcript from at least one of the following genes: PYROXD2, SMOX, CACNA1E, CD163, DDIAS, CLIC3, KLHL2 and HS.553068. In another embodiment, the set of primers are specific to a transcript from at least one of the following genes: PYROXD2, SMOX, CACNA1E and CD163.

For example, the set of primers are specific to transcripts from any of the following combinations of genes: PYROXD2, SMOX, CACNA1E and CD163; PYROXD2, SMOX and CACNA1E; PYROXD2, SMOX and CD163; SMOX, CACNA1E and CD163; PYROXD2, CACNA1E and CD163; PYROXD2 and SMOX; PYROXD2 and CACNA1E; PYROXD2 and CD163; SMOX and CACNA1E; SMOX and CD163; or CACNA1E and CD163; or any other combination.

In one embodiment, the set of primers are specific to a transcript from PYROXD2 and at least one of CACNA1E and SMOX. Therefore, in one embodiment, the set of primers are specific to PYROXD2 and CACNA1E. In another embodiment, the set of primers are specific to PYROXD2 and SMOX. In yet another embodiment, the set of primers are specific to PYROXD2, CACNA1E and SMOX.

In one embodiment, the set of primers are specific to a transcript from at least 5 of the 13 genes. Thus, in one embodiment, the set of primers are specific to PYROXD2, CACNA1E, CD163, KLHL2 and SMOX. In one embodiment, the set of primers are specific to PYROXD2, CACNA1E, IFI27, KLHL2 and SMOX. In one embodiment, the set of primers are specific to PYROXD2, CACNA1E, HS.553068, IFI27 and SMOX. In one embodiment, the set of primers are specific to PYROXD2, DDIAS, CACNA1E, IFI27 and SMOX. In one embodiment, the set of primers are specific to PYROXD2, CACNA1E, CD163, KLHL2 and ZNF185. In one embodiment, the set of primers are specific to PYROXD2, DDIAS, CD163, KLHL2 and SMOX.

In one embodiment, the set of primers are specific to at least 6 of the 13 genes. Thus, in one embodiment, the set of primers are specific to PYROXD2, CACNA1E, CD163, IFI27, KLHL2 and SMOX. In one embodiment, the set of primers are specific to PYROXD2, CACNA1E, CD163, KLHL2, LINC02035 and SMOX. In one embodiment, the set of primers are specific to PYROXD2, DDIAS, CACNA1E, CD163, IFI27 and SMOX. In one embodiment, the set of primers are specific to PYROXD2, CACNA1E, CD163, HS.553068, IFI27 and SMOX. In one embodiment, the set of primers are specific to PYROXD2, CACNA1E, CD163, KLHL2, SMOX and ZNF185. In one embodiment, the set of primers are specific to PYROXD2, CACNA1E, IFI27, KLHL2, RTN1 and SMOX. In one embodiment, the set of primers are specific to PYROXD2, CACNA1E, CD163, CLIC3, KLHL2 and SMOX. In one embodiment, the set of primers are specific to PYROXD2, CACNA1E, CLIC3, IFI27, KLHL2 and SMOX. In one embodiment, the set of primers are specific to PYROXD2, DDIAS, CACNA1E, IFI27, RTN1 and SMOX. In one embodiment, the set of primers are specific to PYROXD2, DDIAS, CD163, IFI27, KLHL2 and SMOX.

In one embodiment, the signature comprises at least 7 of the 13 genes. Thus, in one embodiment, the set of primers are specific to PYROXD2, CACNA1E, CD163, HS.553068, IFI27, KLHL2 and SMOX. In one embodiment, the set of primers are specific to PYROXD2, CACNA1E, CD163, CLIC3, IFI27, KLHL2 and SMOX. In one embodiment, the set of primers are specific to PYROXD2, DDIAS, CACNA1E, CD163, IFI27, KLHL2 and SMOX. In one embodiment, the set of primers are specific to PYROXD2, CACNA1E, CD163, IFI27, KLHL2, RTN1 and SMOX. In one embodiment, the set of primers are specific to PYROXD2, DDIAS, CACNA1E, CD163, HS.553068, IFI27 and SMOX.

In another embodiment, the set of primers are specific to at least 8 of the 13 genes. Thus, in one embodiment, the set of primers are specific to PYROXD2, DDIAS, CACNA1E, CD163, CLIC3, IFI27, KLHL2 and SMOX. In another embodiment, the set of primers are specific to PYROXD2, CACNA1E, CD163, CLIC3, HS.553068, IFI27, KLHL2 and SMOX. In one embodiment, the set of primers are specific to PYROXD2, CACNA1E, CD163, CLIC3, IFI27, KLHL2, RTN1 and SMOX. In one embodiment, the set of primers are specific to PYROXD2, CACNA1E, CD163, HS.553068, IFI27, KLHL2, S100P and SMOX.

In another embodiment, the set of primers are specific to at least 9 of the 13 genes. Thus, in one embodiment, the set of primers are specific to PYROXD2, DDIAS, CACNA1E, CD163, CLIC3, HS.553068, IFI27, KLHL2 and SMOX. In one embodiment, the set of primers are specific to PYROXD2, DDIAS, CACNA1E, CD163, CLIC3, IFI27, KLHL2, RTN1 and SMOX. In one embodiment, the set of primers are specific to PYROXD2, CACNA1E, CD163, CLIC3, HS.553068, IFI27, KLHL2, RTN1 and SMOX.

In another embodiment, the set of primers are specific to at least 10 of the 13 genes. Thus, in one embodiment, the set of primers are specific to PYROXD2, DDIAS, CACNA1E, CD163, CLIC3, IFI27, KLHL2, RTN1, S100P and SMOX. In another embodiment, the set of primers are specific to PYROXD2, DDIAS, CACNA1E, CD163, CLIC3, HS.553068, IFI27, KLHL2, RTN1 and SMOX.

In another embodiment, the set of primers are specific to at least 11 of the 13 genes. Thus, in one embodiment, the set of primers are specific to PYROXD2, DDIAS, CACNA1E, CD163, CLIC3, HS.553068, IFI27, KLHL2, RTN1, S100P and SMOX. In another embodiment, the set of primers are specific to PYROXD2, DDIAS, CACNA1E, CD163, CLIC3, IFI27, KLHL2, LINC02035, RTN1, S100P and SMOX. In another embodiment, the set of primers are specific to PYROXD2, DDIAS, CACNA1E, CD163, CLIC3, IFI27, KLHL2, RTN1, S100P, SMOX and ZNF185.

In one embodiment, the set of primers are specific to at least 12 of the 13 genes. Thus, in one embodiment, the set of primers are specific to PYROXD2, DDIAS, CACNA1E, CD163, CLIC3, HS.553068, IFI27, KLHL2, RTN1, S100P, SMOX and ZNF185. In another embodiment, the set of primers are specific to PYROXD2, DDIAS, CACNA1E, CD163, CLIC3, HS.553068, IFI27, KLHL2, LINC02035, RTN1, S100P and SMOX. In another embodiment, the set of primers are specific to PYROXD2, DDIAS, CACNA1E, CD163, CLIC3, IFI27, KLHL2, LINC02035, RTN1, S100P, SMOX and ZNF185.

In one embodiment, the set of primers are specific to all 13 genes. Thus, in one embodiment, the set of primers are specific to CACNA1E, DDIAS, KLHL2, PYROXD2, SMOX, ZNF185, LINC02035, CLIC3, S100P, IFI27, HS.553068, CD163, and RTN1.

In one embodiment, the gene transcript is RNA, for example mRNA or cRNA. Thus, in one embodiment, the In one embodiment the primers for each gene are at least a pair of nucleic acid primer sequences.

In one embodiment the primer length is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 bases in length.

In one embodiment at least one primer for each gene comprises a label.

In one embodiment the labels on the primers are independently selected from selected from a fluorescent label, a coloured label, and antibody, step tag, his tag.

In one embodiment each primer in a given pair of primers is labelled, for example where one label quenches the fluorescence of the other label when said labels are within proximity of each other.

In another aspect of the disclosure there is provided a gene chip consisting of probes for detecting the modulation in gene expression levels of at least 5 of the following genes: CACNA1E, DDIAS, KLHL2, PYROXD2, SMOX, ZNF185, LINC02035, CLIC3, S100P, IFI27, HS.553068, CD163, and RTN1.

In one embodiment, the Illumina probe IDs for the 13 genes are shown in Table 2. Alternatively, the skilled addressee is able to design custom probes based on the nucleic acid sequence of each of the 13 genes.

In one embodiment, the gene chip further comprises control probes. In the context of this disclosure, the control probes are not considered as part of the gene signature. Hence, in one embodiment, the gene chip consists of probes for at least 5 of the following genes: CACNA1E, DDIAS, KLHL2, PYROXD2, SMOX, ZNF185, LINC02035, CLIC3, S100P, IFI27, HS.553068, CD163, and RTN1; and one or more control probes. In one embodiment, the control probes are specific for transcripts from one or more of the following genes: actin, GAPDH, ubiquitin, 18s rRNA, RPII (POLR2A), TBP, PPIA, GUSB, HSPCB, YWHAZ, SDHA, RPS13, HPRT1 and B4GALT6.

Advantageously, a chip with probes for at least 5 of the 13 genes is able to accurately and reliably differentiate between a sample, for example whole blood derived from a subject having KD from a sample derived from a subject having a bacterial/viral infection and/or inflammatory condition. Such a chip with a small number of probes can be cheaply produced, making the chip particularly suited for use in resource poor settings.

Thus, in one embodiment, the gene chip comprises probes for at least PYROXD2. In one embodiment, the gene chip comprises probes for at least SMOX. In one embodiment, the gene chip comprises probes for at least CACNA1E. In one embodiment, the gene chip comprises probes for at least CD163. In one embodiment, the gene chip comprises probes for at least DDIAS. In one embodiment, the gene chip comprises probes for at least CLIC3. In one embodiment, the gene chip comprises probes for at least KLHL2. In one embodiment, the gene chip comprises probes for at least HS.553068. In one embodiment, the gene chip comprises probes for at least RTN1. In one embodiment, the gene chip comprises probes for at least ZNF185. In one embodiment, the gene chip comprises probes for at least IFI27. In one embodiment, the gene chip comprises probes for at least S100P. In one embodiment, the gene chip comprises probes for least LINC02035.

In one embodiment, the gene chip comprises probes for at least one of the following genes: PYROXD2, SMOX, CACNA1E, CD163, DDIAS, CLIC3, KLHL2 and HS.553068. In another embodiment, the gene chip comprises probes for at least one of the following genes: PYROXD2, SMOX, CACNA1E and CD163.

For example, the gene chip comprises probes for any of the following combinations of genes: PYROXD2, SMOX, CACNA1E and CD163; PYROXD2, SMOX and CACNA1E; PYROXD2, SMOX and CD163; SMOX, CACNA1E and CD163; PYROXD2, CACNA1E and CD163; PYROXD2 and SMOX; PYROXD2 and CACNA1E; PYROXD2 and CD163; SMOX and CACNA1E; SMOX and CD163; or CACNA1E and CD163; or any other combination.

In one embodiment, the gene chip comprises probes for PYROXD2 and at least one of CACNA1E and SMOX. Therefore, in one embodiment, the gene chip comprises probes for PYROXD2 and CACNA1E. In another embodiment, the gene chip comprises probes for PYROXD2 and SMOX. In yet another embodiment, the gene chip comprises probes for PYROXD2, CACNA1E and SMOX.

In one embodiment, the gene chip comprises or consists of probes for at least 5 of the 13 genes. Thus, in one embodiment, the gene chip comprises or consists of probes for PYROXD2, CACNA1E, CD163, KLHL2 and SMOX. In one embodiment, the gene chip comprises or consists of probes for PYROXD2, CACNA1E, IFI27, KLHL2 and SMOX. In one embodiment, the gene chip comprises or consists of probes for PYROXD2, CACNA1E, HS.553068, IFI27 and SMOX. In one embodiment, the gene chip comprises or consists of probes for PYROXD2, DDIAS, CACNA1E, IFI27 and SMOX. In one embodiment, the gene chip comprises or consists of probes for PYROXD2, CACNA1E, CD163, KLHL2 and ZNF185. In one embodiment, the gene chip comprises or consists of probes for PYROXD2, DDIAS, CD163, KLHL2 and SMOX.

In one embodiment, the gene chip comprises or consists of probes for at least 6 of the 13 genes. Thus, in one embodiment, the gene chip comprises or consists of probes for PYROXD2, CACNA1E, CD163, IFI27, KLHL2 and SMOX. In one embodiment, the gene chip comprises or consists of probes for PYROXD2, CACNA1E, CD163, KLHL2, LINC02035 and SMOX. In one embodiment, the gene chip comprises or consists of probes for PYROXD2, DDIAS, CACNA1E, CD163, IFI27 and SMOX. In one embodiment, the gene chip comprises or consists of probes for PYROXD2, CACNA1E, CD163, HS.553068, IFI27 and SMOX. In one embodiment, the gene chip comprises or consists of probes for PYROXD2, CACNA1E, CD163, KLHL2, SMOX and ZNF185. In one embodiment, the gene chip comprises or consists of probes for PYROXD2, CACNA1E, IFI27, KLHL2, RTN1 and SMOX. In one embodiment, the gene chip comprises or consists of probes for PYROXD2, CACNA1E, CD163, CLIC3, KLHL2 and SMOX. In one embodiment, the gene chip comprises or consists of probes for PYROXD2, CACNA1E, CLIC3, IFI27, KLHL2 and SMOX. In one embodiment, the gene chip comprises or consists of probes for PYROXD2, DDIAS, CACNA1E, IFI27, RTN1 and SMOX. In one embodiment, the gene chip comprises or consists of probes for PYROXD2, DDIAS, CD163, IFI27, KLHL2 and SMOX.

In one embodiment, gene chip comprises or consists of probes for at least 7 of the 13 genes. Thus, in one embodiment, the gene chip comprises or consists of probes for PYROXD2, CACNA1E, CD163, HS.553068, IFI27, KLHL2 and SMOX. In one embodiment, the gene chip comprises or consists of probes for PYROXD2, CACNA1E, CD163, CLIC3, IFI27, KLHL2 and SMOX. In one embodiment, the gene chip comprises or consists of probes for PYROXD2, DDIAS, CACNA1E, CD163, IFI27, KLHL2 and SMOX. In one embodiment, the gene chip comprises or consists of probes for PYROXD2, CACNA1E, CD163, IFI27, KLHL2, RTN1 and SMOX. In one embodiment, the gene chip comprises or consists of probes for PYROXD2, DDIAS, CACNA1E, CD163, HS.553068, IFI27 and SMOX.

In another embodiment, the gene chip comprises or consists of probes for at least 8 of the 13 genes. Thus, in one embodiment, the gene chip comprises or consists of probes for PYROXD2, DDIAS, CACNA1E, CD163, CLIC3, IFI27, KLHL2 and SMOX. In another embodiment, the gene chip comprises or consists of probes for PYROXD2, CACNA1E, CD163, CLIC3, HS.553068, IFI27, KLHL2 and SMOX. In one embodiment, the gene chip comprises or consists of probes for PYROXD2, CACNA1E, CD163, CLIC3, IFI27, KLHL2, RTN1 and SMOX. In one embodiment, the gene chip comprises or consists of probes for PYROXD2, CACNA1E, CD163, HS.553068, IFI27, KLHL2, S100P and SMOX.

In another embodiment, the gene chip comprises or consists of probes for at least 9 of the 13 genes. Thus, in one embodiment, the gene chip comprises or consists of probes for PYROXD2, DDIAS, CACNA1E, CD163, CLIC3, HS.553068, IFI27, KLHL2 and SMOX. In one embodiment, the gene chip comprises or consists of probes for PYROXD2, DDIAS, CACNA1E, CD163, CLIC3, IFI27, KLHL2, RTN1 and SMOX. In one embodiment, the gene chip comprises or consists of probes for PYROXD2, CACNA1E, CD163, CLIC3, HS.553068, IFI27, KLHL2, RTN1 and SMOX.

In another embodiment, the gene chip comprises or consists of probes for at least 10 of the 13 genes. Thus, in one embodiment, the gene chip comprises or consists of probes for PYROXD2, DDIAS, CACNA1E, CD163, CLIC3, IFI27, KLHL2, RTN1, S100P and SMOX. In another embodiment, the gene chip comprises or consists of probes for PYROXD2, DDIAS, CACNA1E, CD163, CLIC3, HS.553068, IFI27, KLHL2, RTN1 and SMOX.

In another embodiment, the gene chip comprises or consists of probes for at least 11 of the 13 genes. Thus, in one embodiment, the gene chip comprises or consists of probes for PYROXD2, DDIAS, CACNA1E, CD163, CLIC3, HS.553068, IFI27, KLHL2, RTN1, S100P and SMOX. In another embodiment, the gene chip comprises or consists of probes for PYROXD2, DDIAS, CACNA1E, CD163, CLIC3, IFI27, KLHL2, LINC02035, RTN1, S100P and SMOX. In another embodiment, the gene chip comprises or consists of probes for PYROXD2, DDIAS, CACNA1E, CD163, CLIC3, IFI27, KLHL2, RTN1, S100P, SMOX and ZNF185.

In one embodiment, the gene chip comprises or consists of probes for at least 12 of the 13 genes. Thus, in one embodiment, the gene chip comprises or consists of probes for PYROXD2, DDIAS, CACNA1E, CD163, CLIC3, HS.553068, IFI27, KLHL2, RTN1, S100P, SMOX and ZNF185. In another embodiment, the gene chip comprises or consists of probes for PYROXD2, DDIAS, CACNA1E, CD163, CLIC3, HS.553068, IFI27, KLHL2, LINC02035, RTN1, S100P and SMOX. In another embodiment, the gene chip comprises or consists of probes for PYROXD2, DDIAS, CACNA1E, CD163, CLIC3, IFI27, KLHL2, LINC02035, RTN1, S100P, SMOX and ZNF185.

In one embodiment, the gene chip comprises or consists of probes for all 13 genes. Thus, in one embodiment, the gene chip comprises or consists of probes for CACNA1E, DDIAS, KLHL2, PYROXD2, SMOX, ZNF185, LINC02035, CLIC3, S100P, IFI27, HS.553068, CD163, and RTN1.

In a further embodiment the present disclosure includes use of a known or commercially available gene chip in the method of the present disclosure.

In one aspect, there is provided a point of care test for identifying a subject having KD comprising the set of primers or gene chip as defined above. Advantageously, the presently disclosed test can be performed rapidly in as little as a couple of hours without the need for complex diagnostic or lab equipment. Accordingly, the presently disclosed method can be easily implemented as part of an existing patient care program in a hospital setting as well as in more resource poor settings, such as in remote villages.

In one aspect, there is provided the use of a set of primers or gene chip as defined above in an assay to detect KD in a sample, for example a blood sample.

DETAILED DESCRIPTION

The 13 genes/gene transcripts shown in Table 2 are useful for identifying a patient having KD or discriminating KD from a bacterial infection. In one embodiment the method of the present disclosure is able to differentiate a subject having KD from different conditions/diseases or infections, such as a bacterial/viral infection or an inflammatory condition, which have similar clinical symptoms. In another embodiment the 13 genes/gene transcripts are useful for discriminating from a viral infection. In yet another embodiment, the 13 genes/gene transcripts are useful for discriminating patient having KD from an inflammatory disease, such as juvenile idiopathic arthritis (JIA), Henoch-Schönlein purpura (HSP) or systemic lupus erythematosus (SLE).

In one embodiment one probe is employed for detecting the modulation in gene expression of each gene, for example selected from the list of probes shown in Table 2.

In another embodiment, two or more probes are employed for detecting the modulation of each gene. In one embodiment of the present disclosure the gene signature is the minimum set of genes required to optimally detect the infection or discriminate the disease, for example between a bacterial/viral infection and/or between an inflammatory disease.

Optimally is intended to mean the smallest set of genes needed to discriminate between KD and a bacterial/viral infection and/or inflammatory condition without significant loss of specificity and/or sensitivity of the signature's ability to detect or discriminate.

Detect or detecting as employed herein is intended to refer to the process of identifying KD in a sample, in particular through detecting modulation of the relevant genes in the signature. In one embodiment, a subject may be detected as only having KD. In another embodiment, the subject may have KD and also have a bacterial infection, a viral infection, an inflammatory condition, or a combination thereof.

Discriminate refers to the ability of the signature to differentiate between different disease statuses, for example KD vs a viral/bacterial infection or an inflammatory disease. Detect and discriminate are interchangeable in the context of the gene signature.

Subject as employed herein is a human suspected of having KD or a human having a fever from whom a sample is derived. The term patient may be used interchangeably although in one embodiment a patient has a morbidity.

In one embodiment the method of the present disclosure is performed on a sample derived from a subject having or suspected of having KD, for example wherein the subject exhibits symptoms normally associated with KD.

In one embodiment the method of the present disclosure is performed on a sample derived from a subject having or suspected of having a bacterial/viral infection or an inflammatory condition, but not suspected of having KD, for example wherein the subject exhibits symptoms normally not associated with KD. Testing a sample from such a subject can help to identify an individual who has KD who would normally not be correctly diagnosed.

In one embodiment the subject exhibits symptoms of a viral infection. In another embodiment the subject exhibits symptoms of a bacterial infection. In yet another embodiment the subject exhibits symptoms of both a bacterial and a viral infection. In one embodiment, the subject exhibits symptoms of an inflammatory condition.

In a further embodiment the sample is a sample derived from a febrile subject; that is to say with a temperature above the normal body temperature of 37.5° C.

In yet a further embodiment the analysis is performed to establish if a fever is associated with KD. Establishing the source of the fever/infection advantageously allows the prescription and/or administration of appropriate medication, for example patients identified has having KD can be given appropriate treatment like gamma globulin (IVIg), aspirin, whilst patients with bacterial infections can be given antibiotics and those with viral infections can be given antipyretics.

Efficient treatment is advantageous because it minimises hospital stays, ensures that patients obtain appropriate treatment, which may save lives, especially when the patient is an infant or child, and also ensures that resources are used appropriately.

In recent years it has become apparent that the over-use of antibiotics should be avoided because it leads to bacteria developing resistance. Therefore, the administration of antibiotics to patients who do not have bacterial infection should be avoided.

In one embodiment the subject is an adult. Adult is defined herein as a person of 18 years of age or older.

In one embodiment the subject is a child. Child as employed herein refers to a person under the age of 18, such as 5 to 17 years of age.

In one embodiment, the subject is an infant. Infant as used herein refers to a person in the age range of 0 to 59 days.

Modulation of gene expression as employed herein means the up-regulation or down-regulation of a gene or genes.

Up-regulated as employed herein is intended to refer to a gene transcript which is expressed at higher levels in a diseased or infected patient sample relative to, for example, a control sample free from a relevant disease or infection, or in a sample with latent disease or infection or a different stage of the disease or infection, as appropriate.

Down-regulated as employed herein is intended to refer to a gene transcript which is expressed at lower levels in a diseased or infected patient sample relative to, for example, a control sample free from a relevant disease or infection or in a sample with latent disease or infection or a different stage of the disease or infection. Thus, a gene that is up-regulated is one that is expressed at a higher level in a subject having KD compared to a subject who does not have KD. Likewise, a gene that is down-regulated is expressed at a lower level in a subject having KD compared to a subject who does not have KD.

The modulation is measured by measuring levels of gene expression by an appropriate technique.

Gene expression as employed herein is the process by which information from a gene is used in the synthesis of a functional gene product. These products are often proteins, but in non-protein coding genes such as ribosomal RNA (rRNA), transfer RNA (tRNA) or small nuclear RNA (snRNA) genes, the product is a functional RNA. That is to say, RNA with a function. In the context of the present disclosure, measuring the expression levels of a gene generally refers to measuring the levels of transcripts associated with that gene.

Gene expression data as employed herein is intended to refer to any data generated from a patient sample that is indicative of the expression of the two or more genes, for example 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50.

In one embodiment one or more, for example 1 to 21, such as 2, 3, 4, 5, 6, 7, 8, 9, 10, 11, 12, 13, 14, 15, 16, 17, 18, 19 or 20, genes are replaced by a gene with an equivalent function provided the signature retains the ability to detect/discriminate the relevant clinical status without significant loss in specificity and/or sensitivity.

In one embodiment the genes employed have identity with the 13 genes listed Table 2.

In one embodiment, one or more of the genes in the 13 gene signature are significantly differentially expressed in a sample derived from a subject having KD compared to a sample derived from a subject who does not have KD.

Gene signature as used herein is intended to refer to two or more genes which when tested together are able to detect/discriminate the relevant clinical status. Hence, a gene signature represents a minimal set of genes which have sufficient discriminatory power to identify a subject having a KD or to discriminate a subject having KD from a subject having a bacterial/viral infection or inflammatory disease.

Significantly differentially expressed as employed herein means the gene shows a log 2 fold change >0.5 or <−0.5 in a sample derived from a subject having KD compared to a sample derived from a subject who does not have KD, for example who has a bacterial/viral infection and/or an inflammatory condition.

In one embodiment, up-regulated as used herein means the gene shows a log 2 fold change >0.5.

In one embodiment, down-regulated as used herein means the gene shows a log 2 fold change <−0.5.

In one embodiment, one or more of the following genes are down-regulated in a subject having KD: S100P, IFI27, HS.553068, CD163, and RTN1.

In one embodiment, one or more of the following genes are up-regulated in a subject having KD: CACNA1E, DDIAS, KLHL2, PYROXD2, SMOX, ZNF185, LINC02035, CLIC3.

Presented in the form of as employed herein refers to the laying down of genes from one or more of the signatures in the form of probes on a microarray.

Accurately and robustly as employed herein refers to the fact that the method can be employed in a practical setting or low resource setting, such as Africa, and that the results of performing the method properly give a high level of confidence that a true result is obtained.

High confidence is provided by the method when it provides few results that are false positives (e.g. the result suggests that the subject has a bacterial infection when he/she does not) and also has few false negatives (e.g. the result suggests that the subject does not have a bacterial infection when he/she does).

High confidence would include 90% or greater confidence, such as 91, 92, 93, 94, 95, 96, 97, 98, 99 or 100% confidence when an appropriate statistical test is employed.

In one embodiment the method provides a sensitivity of 80% or greater such as 90% or greater in particular 95% or greater, for example where the sensitivity is calculated as below:

$$\text{sensitivity} = \frac{\text{number of true positives}}{\text{number of true positives} + \text{number of false negatives}}$$
$$= \text{probability of a positive test given that the patient is ill}$$

In one embodiment the method provides a high level of specificity, for example 80% or greater such as 90% or greater in particular 95% or greater, for example where specificity is calculated as shown below:

$$\text{sensitivity} = \frac{\text{number of true negatives}}{\text{number of true negatives} + \text{number of false positives}}$$
$$= \text{probability of a negative test given that the patient is well}$$

In one embodiment the sensitivity of method of the gene signature is 90 to 100%, such as 90, 91, 92, 93, 94, 95, 96, 97, 98 or 99%.

In one embodiment the specificity of the method of the gene signature is 85 to 100%, such as 86, 87, 88, 89, 90, 91, 92, 93, 94, 95, 96, 97, 98 or 99%.

In one embodiment the sensitivity of the method of the gene signature is 85 to 100%, such as 86, 87, 88, 89, 90, 91, 92, 93, 94, 95, 96, 97, 98 or 99%.

In one embodiment the specificity of the method of the gene signature is 85 to 100%, such as 86, 87, 88, 89, 90, 91, 92, 93, 94, 95, 96, 97, 98 or 99%.

There are a number of ways in which gene expression can be measured including microarrays, tiling arrays, DNA or RNA arrays for example on gene chips, RNA-seq and serial analysis of gene expression.

Any suitable method of measuring gene modulation may be employed in the method of the present disclosure.

In one embodiment the gene expression measured is that of the host (e.g. human), for example the host inflammatory response, i.e. not that of the infectious agent or disease.

In one embodiment DNA or RNA from the subject sample is analysed.

In one embodiment RNA from the subject sample is analysed.

In one embodiment mRNA from the subject sample is analysed.

In one embodiment cRNA from the subject sample is analysed.

In one embodiment the sample is solid or fluid, for example blood or serum or a processed form of any one of the same.

A fluid sample as employed herein refers to liquids originating from inside the bodies of living people. They include fluids that are excreted or secreted from the body as well as body water that normally is not. Includes amniotic fluid, aqueous humour and vitreous humour, bile, blood serum, breast milk, cerebrospinal fluid, cerumen (earwax), chyle, endolymph and perilymph, gastric juice, mucus (including nasal drainage and phlegm), sputum, peritoneal fluid, pleural fluid, saliva, sebum (skin oil), semen, sweat, tears, vaginal secretion, vomit, urine. Particularly blood and serum.

Blood as employed herein refers to whole blood, that is serum, blood cells and clotting factors, typically peripheral whole blood.

Serum as employed herein refers to the component of whole blood that is not blood cells or clotting factors. It is plasma with fibrinogens removed.

In one embodiment the subject derived sample is a blood sample.

In one embodiment the sample is whole blood. Hence in one embodiment the RNA sample is derived from whole blood.

The RNA sample may be subjected to further amplification by PCR, such as whole genome amplification in order to increase the amount of starting RNA template available for analysis. Alternatively, the RNA sample may be converted into cDNA by reverse transcriptase, such as HIV-1 reverse transcriptase, moloney murine leukaemia virus (M-MLV) reverse transcriptase, AMV reverse transcriptase and telomerase reverse transcriptase. Such amplification steps may be necessary for smaller sample volumes, such as blood samples obtained from children.

In one or more embodiments the analysis is ex vivo.

Ex vivo as employed herein means that which takes place outside the body.

In one embodiment the gene expression data is generated from a microarray, such as a gene chip.

Microarray as employed herein includes RNA or DNA arrays, such as RNA arrays. Various different forms of microarrays will be known to the skilled person, including but not limited to solid-phase arrays and bead arrays.

Polymerase chain reaction (PCR) as employed herein refers to a widely used molecular technique to make multiple copies of a target DNA sequence. The method relies on thermal cycling, consisting of cycles of repeated heating and cooling of the reaction for DNA melting and enzymatic replication of the DNA. Primers containing sequences complementary to the target region along with a DNA polymerase, which the method is named after, are key components to enable selective and repeated amplification. As PCR progresses, the DNA generated is itself used as a template for replication, setting in motion a chain reaction in which the DNA template is exponentially amplified.

Multiplex PCR as employed herein refers to the use of a polymerase chain reaction (PCR) to amplify two or more different DNA sequences simultaneously, i.e. as if performing many separate PCR reactions together in one reaction.

Primer as employed herein is intended to refer to a short strand of nucleic acid sequence, usually a chemically synthesised oligonucleotide, which serve as a starting point for DNA synthesis reactions.

Primers are typically about 15 base pairs long but can vary from 5 to 100 bases long. It is required in processes such as PCR because DNA polymerases can only add new nucleotides or base pairs to an existing strand of DNA. During a PCR reaction, the primer hybridises to its complementary sequence in a DNA sample. Next, DNA polymerase starts replication at the 3'end of the primer and extends the primer by copying the sequence of the opposite DNA strand.

In one embodiment the primers of the present disclosure are specific for RNA, such as mRNA, i.e. they are complementary to RNA sequences. In another embodiment, the primers are specific for cDNA, i.e. they are complementary to cDNA sequences.

In one embodiment the primers of the present disclosure comprise a label which enables the primers to be detected or isolated. Examples of labels include but are not limited to a fluorescent label, a coloured label, and antibody, step tag, his tag.

In another embodiment, each primer in a given pair of primers is labelled, for example where one label (also known as a quencher) quenches the fluorescence of the other label when said labels are within proximity of each other. Such labels are particularly useful in real time PCR reactions for example. Examples of such pairs include label 6-carboxyfluorescein (FAM) and tetrachlorofluorescein, or tetramethylrhodamine and tetrachlorofluorescein.

Point of care test or bedside test as used herein is intended to refer to a medical diagnostic test which is conducted at or near the point of care, i.e. at the time and place of patient care. This is in contrast with a conventional diagnostic test which is typically confined to the medical laboratory and involves sending specimens away from the point of care to the laboratory for testing. Such diagnostic tests often require many hours or days before the results of the test can be received. In the meantime, patient care must continue without knowledge of the test results. In comparison, a point of care test is typically a simple medical test that can be performed rapidly.

A gene chip is essentially a microarray that is to say an array of discrete regions, typically nucleic acids, which are separate from one another and are, for example arrayed at a density of between, about $100/cm^2$ to $1000/cm^2$, but can be arrayed at greater densities such as $10000/cm^2$. The principle of a microarray experiment, is that mRNA from a given cell line or tissue is used to generate a labelled sample typically labelled cDNA or cRNA, termed the 'target', which is hybridised in parallel to a large number of, nucleic acid sequences, typically DNA or RNA sequences, immobilised on a solid surface in an ordered array. Tens of thousands of transcript species can be detected and quantified simultaneously. Although many different microarray systems have been developed the most commonly used systems today can be divided into two groups.

Using this technique, arrays consisting of more than 30,000 cDNAs can be fitted onto the surface of a conventional microscope slide. For oligonucleotide arrays, short 20-25mers are synthesised in situ, either by photolithography onto silicon wafers (high-density-oligonucleotide arrays from Affymetrix) or by ink-jet technology (developed by Rosetta Inpharmatics and licensed to Agilent Technologies).

Alternatively, pre-synthesised oligonucleotides can be printed onto glass slides. Methods based on synthetic oligonucleotides offer the advantage that because sequence information alone is sufficient to generate the DNA to be arrayed, no time-consuming handling of cDNA resources is required. Also, probes can be designed to represent the most unique part of a given transcript, making the detection of closely related genes or splice variants possible. Although short oligonucleotides may result in less specific hybridization and reduced sensitivity, the arraying of pre-synthesised longer oligonucleotides (50-100mers) has recently been developed to counteract these disadvantages.

In one embodiment the gene chip is an off the shelf, commercially available chip, for example HumanHT-12 v4 Expression BeadChip Kit, available from Illumina, NimbleGen microarrays from Roche, Agilent, Eppendorf and Genechips from Affymetrix such as HU-Ul 33.Plus 2.0 gene chips.

In an alternate embodiment the gene chip employed in the present invention is a bespoke gene chip, that is to say the chip contains only the target genes which are relevant to the desired profile. Custom made chips can be purchased from companies such as Roche, Affymetrix and the like. In yet a further embodiment the bespoke gene chip comprises a minimal disease specific transcript set.

In one embodiment the chip consists of probes for detecting the expression levels of the 13 genes listed in Table 2.

In one embodiment the following Illumina Probe ID nos. are used to detect the modulation in gene expression levels: 7510647 for CACNA1E, 2570019 for DDIAS, 1070593 for KLHL2, 1684497 for PYROXD2, 270068 or 3710553 for SMOX, 6840674 for ZNF185, 3236239 for LINC02035, 5870136 for CLIC3, 1510424 for S100P, 3990170 for IFI27, 1470450 for HS.553068, 2680092 for CD163, and 6860193 for RTN1.

In one or more embodiments above, the chip may further include 1 or more, such as 1 to 10, control probes such as house-keeping genes.

In one embodiment the gene expression data is generated in solution using appropriate probes for the relevant genes.

Probe as employed herein is intended to refer to a hybridisation probe which is a fragment of DNA or RNA of variable length (usually 100-1000 bases long) which is used in DNA or RNA samples to detect the presence of nucleotide sequences (the DNA target) that are complementary to the sequence in the probe. The probe thereby hybridises to single-stranded nucleic acid (DNA or RNA) whose base sequence allows probe-target base pairing due to complementarity between the probe and target.

In one embodiment the method according to the present disclosure and for example chips employed therein may comprise one or more house-keeping genes.

House-keeping genes as employed herein is intended to refer to genes that are not directly relevant to the profile for identifying the disease or infection but are useful for statistical purposes and/or quality control purposes, for example they may assist with normalising the data, in particular a house-keeping gene is a constitutive gene i.e. one that is transcribed at a relatively constant level. The housekeeping gene's products are typically needed for maintenance of the cell.

Examples of housekeeping genes include but are not limited to actin, GAPDH, ubiquitin, 18s rRNA, RPII (POLR2A), TBP, PPIA, GUSB, HSPCB, YWHAZ, SDHA, RPS13, HPRT1 and B4GALT6.

In one embodiment minimal disease specific transcript set as employed herein means the minimum number of genes need to robustly identify the target disease state.

Minimal discriminatory gene set is interchangeable with minimal disease specific transcript set or minimal gene signature.

Normalising as employed herein is intended to refer to statistically accounting for background noise by comparison of data to control data, such as the level of fluorescence of house-keeping genes, for example fluorescent scanned data may be normalized using RMA to allow comparisons between individual chips. Irizarry et al 2003 describes this method.

Scaling as employed herein refers to boosting the contribution of specific genes which are expressed at low levels or have a high fold change but still relatively low fluorescence such that their contribution to the diagnostic signature is increased.

Fold change is often used in analysis of gene expression data in microarray and RNA-Seq experiments, for measuring change in the expression level of a gene and is calculated simply as the ratio of the final value to the initial value i.e. if the initial value is A and final value is B, the fold change is B/A. Tusher et al 2001.

In programs such as Arrayminer, fold change of gene expression can be calculated. The statistical value attached to the fold change is calculated and is the more significant in genes where the level of expression is less variable between subjects in different groups and, for example where the difference between groups is larger.

The step of obtaining a suitable sample from the subject is a routine technique, which involves taking a blood sample. This process presents little risk to donors and does not need to be performed by a doctor but can be performed by appropriately trained support staff. In one embodiment the sample derived from the subject is approximately 2.5 ml of blood, however smaller volumes can be used for example 0.5-1 ml.

Blood or other tissue fluids are immediately placed in an RNA stabilizing buffer such as included in the Pax gene tubes, or Tempus tubes.

If storage is required then it should usually be frozen within 3 hours of collections at −80° C.

In one embodiment the gene expression data is generated from RNA levels in the sample.

For microarray analysis the blood may be processed using a suitable product, such as PAX gene blood RNA extraction kits (Qiagen).

Total RNA may also be purified using the Tripure method-Tripure extraction (Roche Cat. No. 1 667 165). The manufacturer's protocols may be followed. This purification may then be followed by the use of an RNeasy Mini kit-clean-up protocol with DNAse treatment (Qiagen Cat. No. 74106).

Quantification of RNA may be completed using optical density at 260 nm and Quant-IT RiboGreen RNA assay kit (Invitrogen-Molecular probes RI 1490). The Quality of the 28s and 18s ribosomal RNA peaks can be assessed by use of the Agilent bioanalyser.

In another embodiment the method further comprises the step of amplifying the RNA. Amplification may be performed using a suitable kit, for example TotalPrep RNA Amplification kits (Applied Biosystems).

In one embodiment an amplification method may be used in conjunction with the labelling of the RNA for microarray analysis. The Nugen 3' ovation biotin kit (Cat: 2300-12, 2300-60).

The RNA derived from the subject sample is then hybridised to the relevant probes, for example which may be located on a chip. After hybridisation and washing, where appropriate, analysis with an appropriate instrument is performed.

In performing an analysis to ascertain whether a subject presents a gene signature indicative of disease or infection according to the present disclosure, the following steps are performed: obtain mRNA from the sample and prepare nucleic acids targets, hybridise to the array under appropriate conditions, typically as suggested by the manufactures of the microarray (suitably stringent hybridisation conditions such as 3×SSC, 0.1% SDS, at 50<0> C) to bind corresponding probes on the array, and wash if necessary to remove unbound nucleic acid targets and analyse the results.

In one embodiment the readout from the analysis is fluorescence.

In one embodiment the readout from the analysis is colorimetric.

In one embodiment physical detection methods, such as changes in electrical impedance, nanowire technology or microfluidics may be used.

In one embodiment there is provided a method which further comprises the step of quantifying RNA from the subject sample.

If a quality control step is desired, software such as Genome Studio software may be employed.

Numeric value as employed herein is intended to refer to a number obtained for each relevant gene, from the analysis or readout of the gene expression, for example the fluorescence or colorimetric analysis. The numeric value obtained from the initial analysis may be manipulated, corrected and if the result of the processing is a still a number then it will be continue to be a numeric value.

By converting is meant processing of a negative numeric value to make it into a positive value or processing of a positive numeric value to make it into a negative value by simple conversion of a positive sign to a negative or vice versa.

Analysis of the subject-derived sample will for the genes analysed will give a range of numeric values some of which are positive (preceded by + and in mathematical terms considered greater than zero) and some of which are negative (preceded by − and in strict mathematical terms are considered to less than zero). The positive and negative in the context of gene expression analysis is a convenient mechanism for representing genes which are up-regulated and genes which are down regulated.

In the method of the present disclosure either all the numeric values of genes which are down-regulated and represented by a negative number are converted to the corresponding positive number (i.e. by simply changing the sign) for example −1 would be converted to 1 or all the positive numeric values for the up-regulated genes are converted to the corresponding negative number.

The present inventors have established that this step of rendering the numeric values for the gene expressions positive or alternatively all negative allows the summating of the values to obtain a single value that is indicative of the presence of disease or infection or the absence of the same.

This is a huge simplification of the processing of gene expression data and represents a practical step forward thereby rendering the method suitable for routine use in the clinic.

By discriminatory power is meant the ability to distinguish between a KD sample and a bacterial infected, a viral infected sample/subject and/or between and an inflammatory disease, such as SLE, JIA and HSP.

The discriminatory power of the method according to the present disclosure may, for example, be increased by attaching greater weighting to genes which are more significant in the signature, even if they are expressed at low or lower absolute levels.

As employed herein, raw numeric value is intended to, for example refer to unprocessed fluorescent values from the gene chip, either absolute fluorescence or relative to a house keeping gene or genes.

Summating as employed herein is intended to refer to act or process of adding numerical values.

Composite expression score as employed herein means the sum (aggregate number) of all the individual numerical values generated for the relevant genes by the analysis, for example the sum of the fluorescence data for all the relevant up and down regulated genes. The score may or may not be normalised and/or scaled and/or weighted.

In one embodiment the composite expression score is normalised.

In one embodiment the composite expression score is scaled.

In one embodiment the composite expression score is weighted.

Weighted or statistically weighted as employed herein is intended to refer to the relevant value being adjusted to more appropriately reflect its contribution to the signature.

In one embodiment the method employs a simplified risk score as employed in the examples herein.

Simplified risk score is also known as disease risk score (DRS).

Control as employed herein is intended to refer to a positive (control) sample and/or a negative (control) sample which, for example is used to compare the subject sample to, and/or a numerical value or numerical range which has been defined to allow the subject sample to be designated as positive or negative for disease/infection by reference thereto.

Positive control sample as employed herein is a sample known to be positive for the pathogen or disease in relation to which the analysis is being performed, such as a bacterial infection.

Negative control sample as employed herein is intended to refer to a sample known to be negative for the pathogen or disease in relation to which the analysis is being performed.

In one embodiment the control is a sample, for example a positive control sample or a negative control sample, such as a negative control sample.

In one embodiment the control is a numerical value, such as a numerical range, for example a statistically determined range obtained from an adequate sample size defining the cut-offs for accurate distinction of disease cases from controls.

Conversion of Multi-Gene Transcript Disease Signatures into a Single Number Disease Score Once the RNA expression signature of the disease has been identified by variable selection, the transcripts are separated based on their up- or down-regulation relative to the comparator group. The two groups of transcripts are selected and collated separately.

Summation of Up-Regulated and Down-Regulated RNA Transcripts

To identify the single disease risk score for any individual patient, the raw intensities, for example fluorescent intensities (either absolute or relative to housekeeping standards) of all the up-regulated RNA transcripts associated with the disease are summated. Similarly summation of all down-regulated transcripts for each individual is achieved by combining the raw values (for example fluorescence) for each transcript relative to the unchanged housekeeping gene standards. Since the transcripts have various levels of expression and respectively their fold changes differ as well, instead of summing the raw expression values, they can be scaled and normalised between 0,1. Alternatively they can be weighted to allow important genes to carry greater effect. Then, for every sample the expression values of the signature's transcripts are summated, separately for the up- and down-regulated transcripts.

The total disease score incorporating the summated fluorescence of up- and down-regulated genes is calculated by adding the summated score of the down-regulated transcripts (after conversion to a positive number) to the summated score of the up-regulated transcripts, to give a single number composite expression score. This score maximally distinguishes the cases and controls and reflects the contribution of the up- and down-regulated transcripts to this distinction.

Comparison of the Disease Risk Score in Cases and Controls

The composite expression scores for patients and the comparator group may be compared, in order to derive the means and variance of the groups, from which statistical cut-offs are defined for accurate distinction of cases from controls. Using the disease subjects and comparator populations, sensitivities and specificities for the disease risk score may be calculated using, for example a Support Vector Machine and internal elastic net classification.

Disease risk score as employed herein is an indicator of the likelihood that patient has a bacterial infection when comparing their composite expression score to the comparator group's composite expression score.

Development of the Disease Risk Score into a Simple Clinical Test for Disease Severity or Disease Risk Prediction The approach outlined above in which complex RNA expression signatures of disease or disease processes are converted into a single score which predicts disease risk can be used to develop simple, cheap and clinically applicable tests for disease diagnosis or risk prediction.

The procedure is as follows: For tests based on differential gene expression between cases and controls (or between different categories of cases such as severity), the up- and down-regulated transcripts identified as relevant may be printed onto a suitable solid surface such as microarray slide, bead, tube or well.

Up-regulated transcripts may be co-located separately from down-regulated transcripts either in separate wells or separate tubes. A panel of unchanged housekeeping genes may also be printed separately for normalisation of the results.

RNA recovered from individual patients using standard recovery and quantification methods (with or without amplification) is hybridised to the pools of up- and down-regulated transcripts and the unchanged housekeeping transcripts.

Control RNA is hybridised in parallel to the same pools of up- or down-regulated transcripts.

Total value, for example fluorescence for the subject sample and optionally the control sample is then read for up- and down-regulated transcripts and the results combined to give a composite expression score for patients and controls, which is/are then compared with a reference range of a suitable number of healthy controls or comparator subjects.

Correcting the Detected Signal for the Relative Abundance of RNA Species in the Subject Sample The details above explain how a complex signature of many transcripts can be reduced to the minimum set that is maximally able to distinguish between patients and other phenotypes. For example, within the up-regulated transcript set, there will be some transcripts that have a total level of expression many fold lower than that of others. However, these transcripts may be highly discriminatory despite their overall low level of expression. The weighting derived from the elastic net coefficient can be included in the test, in a number of different ways. Firstly, the number of copies of individual transcripts included in the assay can be varied. Secondly, in order to ensure that the signal from rare, important transcripts are not swamped by that from transcripts expressed at a higher level, one option would be to select probes for a test that are neither overly strongly nor too weakly expressed, so that the contribution of multiple probes is maximised. Alternatively, it may be possible to adjust the signal from low-abundance transcripts by a scaling factor.

Whilst this can be done at the analysis stage using current transcriptomic technology as each signal is measured separately, in a simple colorimetric test only the total colour change will be measured, and it would not therefore be possible to scale the signal from selected transcripts. This problem can be circumnavigated by reversing the chemistry usually associated with arrays. In conventional array chemistry, the probes are coupled to a solid surface, and the amount of biotin-labelled, patient-derived target that binds is measured. Instead, we propose coupling the biotin-labelled cRNA derived from the patient to an avidin-coated surface, and then adding DNA probes coupled to a chromogenic enzyme via an adaptor system. At the design and manufacturing stage, probes for low-abundance but important transcripts are coupled to greater numbers, or more potent forms of the chromogenic enzyme, allowing the signal for these transcripts to be 'scaled-up' within the final single-channel colorimetric readout. This approach would be used to normalise the relative input from each probe in the up-regulated, down-regulated and housekeeping channels of the kit, so that each probe makes an appropriately weighted contribution to the final reading, which may take account of its discriminatory power, suggested by the weights of variable selection methods.

The detection system for measuring multiple up or down regulated genes may also be adapted to use rTPCR to detect the transcripts comprising the diagnostic signature, with summation of the separate pooled values for up and down regulated transcripts, or physical detection methods such as changes in electrical impedance. In this approach, the transcripts in question are printed on nanowire surfaces or within microfluidic cartridges, and binding of the corresponding ligand for each transcript is detected by changes in impedance or other physical detection system.

In one embodiment the gene chip is a fluorescent gene chip that is to say the readout is fluorescence.

Fluorescence as employed herein refers to the emission of light by a substance that has absorbed light or other electromagnetic radiation.

Thus in an alternate embodiment the gene chip is a colorimetric gene chip, for example colorimetric gene chip uses microarray technology wherein avidin is used to attach enzymes such as peroxidase or other chromogenic substrates to the biotin probe currently used to attach fluorescent markers to DNA. The present disclosure extends to a microarray chip adapted to be read by colorimetric analysis and adapted to discriminate a subject having a bacterial infection from a subject having a viral infection or an inflammatory disease. The present disclosure also extends to use of a colorimetric chip to analyse a subject sample for discriminating a subject having a bacterial infection from a subject having a viral infection or an inflammatory disease.

Colorimetric as employed herein refers to as assay wherein the output is in the human visible spectrum.

In an alternative embodiment, a gene set or probe set for discriminating a subject having a bacterial infection from a subject having a viral infection or an inflammatory disease may be detected by physical detection methods including nanowire technology, changes in electrical impedance, or microfluidics.

The readout for the assay can be converted from a fluorescent readout as used in current microarray technology into a simple colorimetric format or one using physical detection methods such as changes in impedance, which can be read with minimal equipment. For example, this is achieved by utilising the Biotin currently used to attach fluorescent markers to DNA. Biotin has high affinity for avidin which can be used to attach enzymes such as peroxidase or other chromogenic substrates. This process will allow the quantity of cRNA binding to the target transcripts to be quantified using a chromogenic process rather than fluorescence. Simplified assays providing yes/no indications of disease status can then be developed by comparison of the colour intensity of the up- and down-regulated pools of transcripts with control colour standards. Similar approaches can enable detection of multiple gene signatures using physical methods such as changes in electrical impedance.

This aspect of the invention is likely to be particularly advantageous for use in remote or under-resourced settings or for rapid diagnosis in "near patient" tests. For example, places in Africa because the equipment required to read the chip is likely to be simpler.

Multiplex assay as employed herein refers to a type of assay that simultaneously measures several analytes (often dozens or more) in a single run/cycle of the assay. It is distinguished from procedures that measure one analyte at a time.

In one embodiment there is provided a bespoke gene chip for use in the method, in particular as described herein.

In one embodiment there is provided use of a known gene chip for use in the method described herein in particular to identify one or more gene signatures described herein.

In one aspect there is provided a method of determining whether to administer a treatment for KD to a subject, such as a subject suspected of having KD, for example a subject exhibiting symptoms of having KD, by employing the method disclosed therein, and administering the treatment to the subject if the method indicates that the subject has KD. Examples of suitable treatments for KD include but are not limited to gamma globulin (IVIg), aspirin, or other anti-inflammatory agents such as steroids and infliximab, including combinations thereof.

Gene signature, gene transcript signature, gene set, disease signature, diagnostic signature and gene profile are used interchangeably throughout and should be interpreted to mean gene signature.

In the context of this specification "comprising" is to be interpreted as "including".

Aspects of the invention comprising certain elements are also intended to extend to alternative embodiments "consisting" or "consisting essentially" of the relevant elements.

Where technically appropriate, embodiments of the invention may be combined.

Embodiments are described herein as comprising certain features/elements. The disclosure also extends to separate embodiments consisting or consisting essentially of said features/elements.

Technical references such as patents and applications are incorporated herein by reference.

Any embodiments specifically and explicitly recited herein may form the basis of a disclaimer either alone or in combination with one or more further embodiments.

BRIEF DESCRIPTION OF THE FIGURES

FIG. 1 shows the diagnostic algorithm for assigning patients to diagnostic groups. KD=Kawasaki disease; AHA=American Heart Association; CAA=coronary artery aneurysm; JIA=juvenile idiopathic arthritis; HSP=Henoch-Schönlein purpura; CRP=C-reactive protein.

FIG. 2 shows the Overall study pipeline showing sample handling, derivation of test and t raining datasets, data processing and analysis pipeline.
[a] see methods (Example 1); [b] Healthy controls were used in model building but were excluded from estimates of model accuracy; [c] Diagnostic performance assessed on 72 patients (days 2-7 of illness). Abbreviations: KD=Kawasaki disease; DB=definite bacterial; DV=definite viral; U=infections of uncertain bacterial or viral aetiology; JIA=juvenile idiopathic arthritis; HSP=Henoch-Schönlein purpura; HC=healthy controls; PDMS=Parallel Deterministic Model Search; SDE=significantly differentially expressed; FC=fold change.

FIG. 3 shows the performance of the 13-transcript signature on the discovery test and validation sets. Classification (A), and receiver operating characteristic (ROC) curve (B) of the 13-transcript signature in the discovery test set, comprising patients with Kawasaki Disease (KD) and patients with other diseases, using the Disease Risk Score (DRS) values. Classification (C), and ROC curve (D) of the 13-transcript signature in the validation set, comprising three KD clinical subgroups of differing diagnostic certainty and patients with other diseases. In box plots, horizontal lines represent the median; lower and upper edges represent interquartile ranges; whiskers represent the range, or 1.5× the interquartile range, whichever is smaller. The horizontal line across the graphs indicates the DRS threshold that separates patients predicted as KD (above the line) or not KD (below), as determined by the point in the ROC curve that maximized sensitivity and specificity in the discovery training group. KD=Kawasaki disease; DB=definite bacterial; DV=definite viral; U=infections of uncertain bacterial or viral aetiology; JIA=juvenile idiopathic arthritis; HSP=Henoch-Schonlein Purpura; KD=def definite KD; KD-HP=highly probable KD; KD-P=possible KD.

FIG. 4 shows the performance of the 13-transcript signature by illness day at sample collection in validation set. The X axis shows the collection day of the sample in relation to the first day of illness (i.e. initiation of fever). Black dots=definite KD, grey dots=highly probable KD, black dots with arrows=possible KD clinical subgroups in the validation set.

FIG. 5 shows the principal component analysis (PCA) plot of PC1 & PC2 in the discovery cohort after background adjustment and normalisation. A sample from a KD patient was removed (arrow) from subsequent analysis. Each spot is data from an array. KD =Kawasaki Disease, DB=Definite Bacterial, DV=Definite Viral, HC=healthy controls, U=infections of uncertain bacterial or viral aetiology, JIA=juvenile idiopathic arthritis, HSP=Henoch-Schönlein purpura.

FIG. 6 shows PCA plots of (A) naïve merging of validation cohorts and (B) merging using ComBat. Each spot represents data from an array; KD-acute=Acute Kawasaki Disease, KD-conv=Convalescent Kawasaki Disease, DB=Definite Bacterial, DV=Definite Viral, U=infections of uncertain bacterial or viral aetiology, HC healthy controls. Panel (B) includes data from 30 KD patients with samples after the 7th day of fever, who were not included in the diagnostic performance calculations.

EXAMPLE 1—IDENTIFICATION OF 13 TRANSCRIPT GENE SIGNATURE PATIENT STUDY GROUPS

Figure 7:
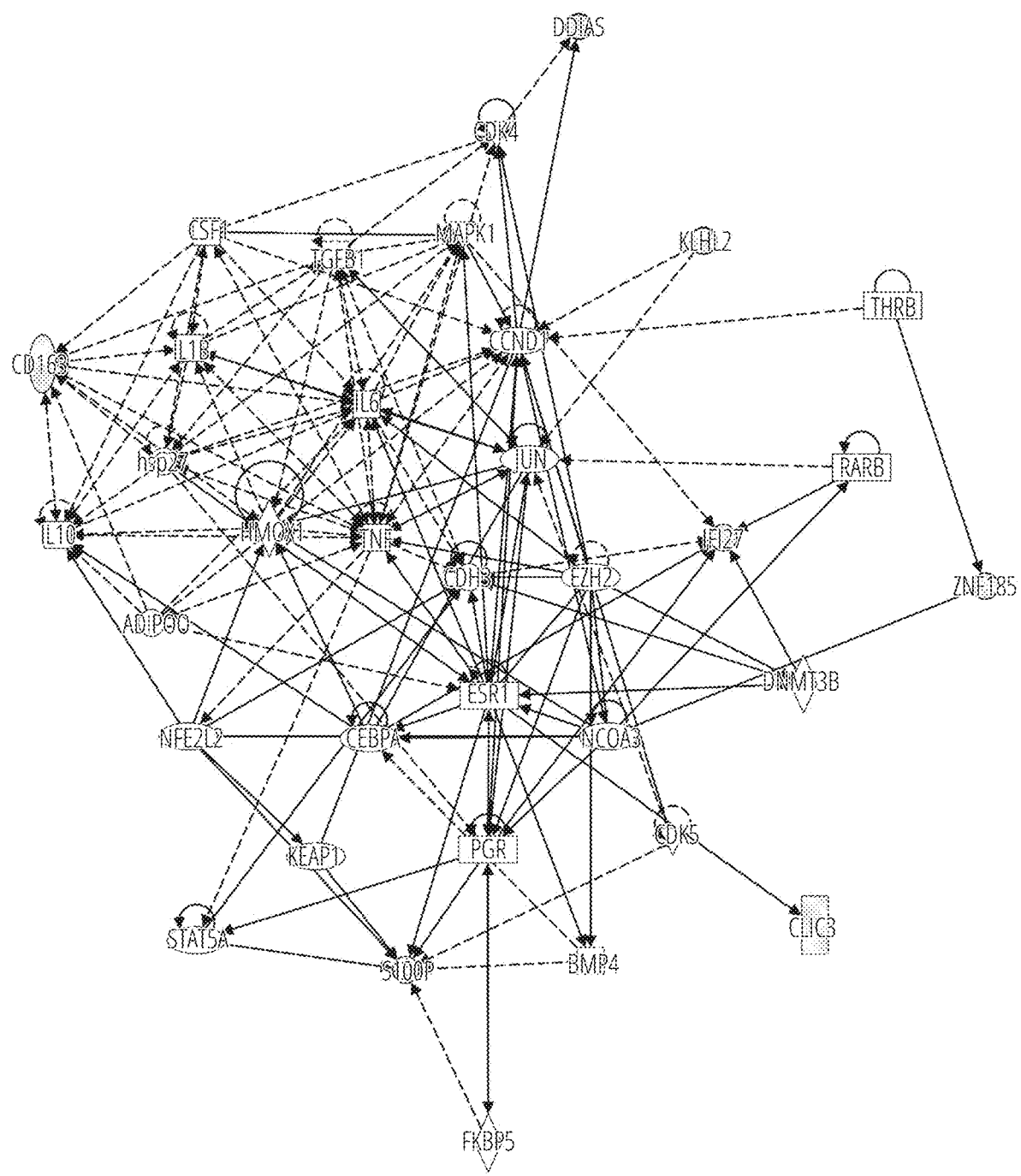
FIG. 7 shows a gene network derived from the 13-transcript signature. The network was generated using Ingenuity Pathways Analysis. 12 of the 13 transcripts were mapped to the database. This network, containing 7 focus molecules was the top network in the analysis. Each molecule is coloured according to the direction of expression in KD. Unbroken lines indicate direct interaction, dashed lines indicate indirect interaction. The legend to the network is located at: http://ingenuity.force.com/ipa/articles/Feature-_Description/Legend.

The differential diagnosis for KD includes multiple infectious and inflammatory conditions, and we therefore established a case-control discovery study group of children with KD and a range of other infectious and inflammatory diseases with clinical signs overlapping KD. Patients were prospectively recruited, at pediatric centres in the UK, the Netherlands, Spain, and USA, if they had febrile illness and required blood testing for clinical investigation, as part of the Immunopathology of Respiratory, Inflammatory and Infectious Disease Study [20], the Spanish GENDRES study, the USA-based Kawasaki Disease Research Center Program or the Dutch Kawasaki study.

Children recruited with KD represented a combination of those presenting directly to the study centre Emergency Department, and patients referred from regional centres. However, our study included only those patients for whom blood sampling had taken place before initiation of IVIG for treatment of KD and in the first 7 days of the illness. Febrile controls were recruited with blood samples collected early, before clinical diagnosis was confirmed, in order to obtain samples as close to presentation as possible, including patients referred for evaluation of possible KD by practitioners in the community, who represented the true population for whom a diagnostic test would be extremely relevant.

Febrile controls were assigned to diagnostic groups using predefined criteria, once the results of all investigations were available (supplementary appendix and FIG. 1). Children with comorbidities likely to influence gene expression, such as immunosuppressive treatment or bone marrow transplant, were excluded. We included comparator groups of children presenting with inflammatory illness: Henoch-Schonlein Purpura (HSP) and Juvenile Idiopathic Arthritis (JIA).

Patients in the validation study group were similarly recruited as part of biomarker studies of febrile children presenting to hospital and requiring blood tests, as has been described previously [21, 22]. Patients presenting to hospital within ten days of the onset of a febrile illness were recruited and blood samples for gene expression analysis collected at the same time as routine diagnostic studies to evaluate the cause of the child's illness. Healthy control children with no recent (2 weeks) history of fever or immunisation were recruited alongside KD and febrile control patients as part of the discovery and validation studies. Data from healthy controls were used to standardise data obtained in different microarray experiments but were not used to evaluate the performance of the signature.

KD Case Definition

KD was diagnosed on the basis of the American Heart Association (AHA) criteria [14]. Patients diagnosed with KD underwent 2D echocardiography soon after presentation and at two and six weeks after onset. Patients with fewer than four of the classic criteria were included as incomplete KD if the maximum coronary artery Z score (Zmax) (standard deviation units from the mean internal diameter normalized for body surface area) at any time during the illness for the left anterior descending or right coronary arteries was >2.5, or if they satisfied the algorithm for incomplete KD in the AHA guidelines. Patients were classified as having normal (Zmax<2.5) or dilated coronary arteries (Zmax≥2.5<5.0) or CAA (Zmax≥5.0). Because of inter-operator variability in exact coronary artery dimensions, we set a high (Zmax≥5.0) threshold to define patients with aneurysms in order to reduce misclassification.

Further Classification of KD by Diagnostic Certainty

As there is no "gold" standard for diagnosis of KD, some patients may meet the criteria for KD but have other conditions such as staphylococcal or streptococcal infection, viral infection or inflammatory diseases. Therefore, we further categorized KD patients in the validation study group based on certainty of clinical diagnosis. All clinical records, laboratory results, echocardiogram reports, response to treatment and follow-up clinic notes were reviewed by an independent pediatric infectious disease specialist and expert on KD (author MPG—blinded to the analysis). Patients with documented CAA (Zmax ≥5.0) persisting six weeks after onset were considered to have definite KD, as there is no other self-resolving inflammatory illness in childhood leading to CAA. The remaining patients (all of whom were treated with IVIG by the clinical team for suspected KD) were classified as highly probable, possible or unlikely KD by the expert reviewer. This review identified no "unlikely KD" cases.

Febrile Control Children with Infection or Other Inflammatory Syndromes

Children presenting with febrile illnesses were assigned as having definite bacterial infection, definite viral infection, suspected bacterial or viral infection, HSP or JIA using the criteria shown in FIG. 1 and described in the supplementary appendix.

Ethical Approval and Consent

Patients were recruited under approvals by the Research Ethics Committees of UCSD (Human Research Protection Program #140220), Spain (Ethical Committee of Clinical Investigation of Galicia, CEIC ref 2010/015), Amsterdam (NL41023.018.12 and NL34230.018.10), and the UK (St Mary's Hospital 09/H0712/58, 13/LO/0026).

Oversight and Conduct of the Study

Patients were categorized into disease groups (FIG. 1) after evaluation of all results by at least two independent clinicians not involved in the patient's care (authors JAH, JCB, JK, MPG, AMB). All samples were anonymized. The transcriptomic datasets were analyzed only after the clinical assignments were finalized and dispatched for independent verification (supplementary appendix).

Discovery and Validation of Gene Expression Signature

The overall study design, and signature discovery pipeline is shown in FIG. 2. Whole blood was collected at the time of recruitment (before IVIG treatment for KD cases) into PAXgene blood RNA tubes (PreAnalytiX, Germany), frozen, extracted and analysed on Human HT-12 v.4 BeadChip arrays (Illumina). An earlier Illumina BeadChip array (HT-12 v.3) with largely overlapping probes was used in a subset of the validation study group. Details of laboratory methods are provided in the Supplementary Appendix.

Statistical Analysis

Transcript Signature Discovery

Analysis of the transcriptomic data was conducted with 'R' Language and Environment for Statistical Computing (R) 3.2.2 (supplementary methods). As shown in FIG. 2, the discovery study group was randomly divided into an 80% 'training' set and a 20% 'test set'. The signature was identified in the training set and validated in the test set as well as in a second study group (the validation study group) established using our previously reported acute and convalescent KD patients [21] and acute bacterial and viral patients [22] (supplementary methods). After quality control and filtering (supplementary methods), significantly differentially expressed (SDE) transcripts in KD patients compared to all other diseases were identified in the training set.

Small Signature Discovery Using Parallel Deterministic Model Search (PDMS)

A novel method, PDMS, that identifies and ranks transcript signatures on the basis of the least number of transcripts and highest accuracy in discrimination, was used to identify a parsimonious gene expression signature comprising the smallest number of transcripts that optimally distinguished KD from other diseases. The method first evaluates all possible one and two-gene models distinguishing KD from comparator diseases based on all SDE transcripts, and takes the 100 best-fitting two-gene models to the next round when a further gene is added to the model, and all combinations are again evaluated. The process continues with incremental addition of one further gene at a time to the best 100 models. The optimum signature for a given number of transcripts (model size) was selected after ranking each model by its Watanabe-Akaike Information Criterion, which is a Bayesian estimate of the out-of-sample error [23]. The optimum model size was determined by cross-validation. Further details are in the supplementary statistical methods.

Disease Risk Score and Assessment of Model Accuracy

We applied our previously reported Disease Risk Score (DRS) method that assigns individual disease risk based on the transcripts included in the diagnostic signature [15]. The DRS combines the fluorescence intensity of up-regulated transcripts and subtracts the combined fluorescence intensity of down-regulated transcripts [15] and might facilitate development of tests from complex signatures. Healthy controls were used in model building but were excluded from estimates of model accuracy, assessed by area under the receiver operator curve (AUC), sensitivity and specificity.

Supplementary Methods
RNA Sample Extraction and Processing

Whole blood (2.5 ml) was collected into PAXgene blood RNA tubes (PreAnalytiX, Germany), incubated for 2 hours, frozen at −20° C. within 6 hours of collection, before storage at −80° C. RNA was extracted using PAXgene blood RNA kits (PreAnalytix, Germany) according to the manufacturer's instructions. The integrity and yield of the total RNA was assessed using an Agilent 2100 Bioanalyser and a NanoDrop 1000 spectrophotometer. The samples used in the discovery cohort came from the USA (UCSD), Spain, The Netherlands and UK. All samples were extracted in the UK except for the samples from the USA. After quantification and quality control, biotin-labeled cRNA was prepared using Illumina TotalPrep RNA Amplification kits (Applied Biosystems) from 500 ng RNA. Labeled CRNA was hybridized overnight to Human HT-12 v.4 Expression BeadChip arrays (Illumina). After washing, blocking and staining, the arrays were scanned using an Illumina BeadArray Reader according to the manufacturer's instructions. Using Genome Studio software the microarray images were inspected for artifacts and QC parameters were assessed. No arrays were excluded at this stage.

Pathogen Diagnosis

Viral diagnostics were undertaken on nasopharyngeal aspirates using immunofluorescence (RSV, adenovirus, parainfluenza virus, influenza A+B) and nested PCR (RSV, adenovirus, parainfluenza 1-4, influenza A+B, bocavirus, metapneumovirus, rhinovirus/enterovirus). Bacterial cultures included blood, CSF, urine and tissue sites. Pneumococcal antigen was measured in blood and urine, and bacterial DNA was detected by meningococcal and pneumococcal PCR.

Diagnostic Process in Febrile Controls

Patients had a diagnostic work-up as directed by the clinical team, including blood count, blood chemistry, C-reactive protein (CRP), blood urine and throat swab cultures; cerebrospinal fluid analysis and chest radiographs were performed where appropriate. Multiplex PCR was used to detect common respiratory viruses in nasopharyngeal aspirates or throat swabs, and common viruses in blood. Once the results of all investigations were available, patients were assigned to diagnostic groups using predefined criteria (FIG. 1), as follows.

Bacterial Infection:

Patients assigned to the bacterial pathogen group had a bacterial pathogen (gram-positive coccus or gram-negative *bacillus*) identified by culture or by molecular techniques in a sample from a sterile site (blood, CSF, pleural space, joint, urine), and a clinical syndrome in keeping with the identified bacterial species. This group included patients with and without viral co-infection. Children diagnosed with other bacterial infections (for instance *mycoplasma*, pertussis, mycobacteria) were not included in this group. No threshold for inflammatory markers was set for this group, as identification of bacteria in a sterile-site sample was taken as conclusive evidence for a confirmed bacterial infection.

Viral Infection:

Patients in the viral infection group had an identified virus, a clinical syndrome in keeping with viral infection, and no microbiological or clinical features of bacterial disease. In order to avoid inclusion of children with occult bacterial infection in the viral group, children with raised inflammatory markers were excluded. A maximum threshold was set at CRP of 60 mg/L, and neutrophil count of $12 \times 10^9$/L. Among the 94 children, the most frequent pathogens were RSV (27 children), influenza A/B and adenovirus (23 children each).

Uncertain Bacterial or Viral Infection:

When children with an acute febrile illness and features of infection could not be assigned confidently to one of the above groups, they were labelled as 'Uncertain Bacterial or Viral'. Children in this group had inconclusive features of bacterial or viral infection, negative microbiological findings or absent virological investigations, a syndrome inconsistent with their microbiological findings, inflammatory markers inconsistent with other clinical features of their illness, or insufficient clinical data for confident coding in another group. Patients in this group did not have bacterial infection detected at a sterile site, and some patients did have detectable virus.

Other Inflammatory Syndromes:

a) Henoch-Schönlein purpura (HSP) was diagnosed in children presenting with palpable purpura, typically over the buttocks and extensor surfaces in association with abdominal pain, arthralgia or renal abnormalities (haematuria and proteinuria); b) Juvenile idiopathic arthritis (JIA) was defined according to International League of Associations for Rheumatology [37]. Patients with JIA included i) treatment-naïve and ii) active-exacerbation/smouldering.

Statistical Methods
Microarray Pre-Processing—the Discovery Dataset

Background subtraction and robust spline normalisation (RSN) were applied to the raw expression data using the R package lumi [38]. Sample outliers were assessed by Principal Component Analysis (PCA). One sample from a Kawasaki patient, was a clear outlier on PC 1 and was removed from the analysis (FIG. 5).

The samples in the discovery dataset were randomly assigned to ten different folds conditional on equal numbers of each comparator group (KD Kawasaki Disease, DB Definite Bacterial, DV Definite Viral, U infections of uncertain bacterial or viral aetiology, JIA juvenile idiopathic arthritis, HSP Henoch-Schonlein purpura, HC healthy controls). Two folds (20%) were reserved as the test set and the remaining eight folds made up the training set. As a diagnostic test for KD would be of most value early in the course of the illness, we developed our signature using only samples from patients at 7 or fewer days of fever in the discovery cohort.

Microarray Pre-Processing—the Validation Dataset

The validation dataset was constructed by merging two gene-expression datasets: one with acute and convalescent Kawasaki samples and one with bacterial and viral infections [40]. All convalescent samples had ESR (erythrocyte sedimentation rate) levels less than 40 mm/hr and all acute samples were taken within ten days of onset of illness. Background subtraction and RSN normalisation were applied to the two datasets separately in the R package lumi [38]. At this stage, there were differences between the cohorts. This is evident from a PCA plot which shows that PC1 clearly distinguishes samples by batch (FIG. 6a). We therefore employed the ComBat [41] method to remove batch effects. Two binary covariates were passed to ComBat which assigned samples to three groups—healthy, KD and other diseases. The Kawasaki convalescent samples were assigned as healthy. A PCA after ComBat shows samples from both batches overlap on a plot of PC1 against PC2 with no significant batch effects (FIG. 6b).

Model Estimation

Before model estimation probes were pre-filtered to identify robustly expressed transcripts with $\log_2$ fold change ≥1 between the relevant disease groups. This was implemented by selecting probes meeting all of the following criteria in the training data:
1. Probes measured on both V3 and V4 Illumina Beadchips
2. Robustly expressed transcripts: for each probe, we calculated the proportion of samples in each comparator group for which the detection threshold p-value<0.01, and selected those probes for which this proportion was >80% in at least one disease group
3. The majority of Kawasaki patients were recruited in UCSD. To ensure probe selection was not biased by batch effects emanating from UCSD, we excluded probes which showed association with recruitment at UCSD at p<0.05 in a linear model conditional on age in months and all disease groups which also included non-KD patients recruited from UCSD (DV, U, KD and HSP)
4. $\log_2$ fold change (conditional on age) was calculated between Kawasaki and each other comparator group; we took forward those probes with |$\log_2$ fold change|>1 for at least one of these comparisons The functions lmFit and eBayes in the R package limma were used to calculate probe association statistic used in steps (3) and (4) above.

Discovery Using Parallel Deterministic Model Search (PDMS)

We used an in-house method, PDMS, to derive a parsimonious gene-expression signature, which balances small transcript number with accurate discrimination. The method iteratively estimates logistic regression coefficients for a selected subset of gene-expression levels (covariates). The regression coefficients are assigned zero-centred Gaussian prior distributions, with precision parameter $\tau$ (where $\tau=1/$ variance, and is equivalent to the penalty), to induce shrinkage of the coefficients to zero. The method searches as many models as possible and chooses the "best" one, with each model comprising a unique subset of selected covariates with their respective logistic regression coefficients.

In order to find the best prior probability distribution shrinkage parameter, we assessed the precision of each model using LASSO cross-validation of multiple partitions of the discovery data. The R package glmnet was used to determine the LASSO penalty with the minimum out-of-sample cross-validated deviance. We then set t by equating the penalty induced by LASSO with the penalty induced by a Gaussian prior on the largest regression coefficient ($\beta_{Max}$) of the optimum LASSO fit. Denoting the LASSO penalty parameter by $\lambda$:

LASSO penalty=Gaussian penalty $$\lambda|\beta| = \frac{\tau}{2}\beta^2$$

$$\tau = 2\frac{\lambda_{min}}{\beta_{max}}$$

The PDMS method proceeded as follows: using the pre-filtered probes that were robustly expressed with $\log_2$ fold change ≥1 between groups, all possible one and two-transcript models were evaluated and ranked, based on their log-likelihood (the measure of how well the model fits the data), and the top 100 two-transcript models were taken forward. In the next stage the algorithm determined the unique set of three-gene models that could be constructed from the addition of one gene to each of the top 100 two-gene models. The log-likelihood of these models was calculated, and the process continued taking forward the top 100 models to construct models one gene larger.

For models of a given size (number of transcripts), the models are ranked by the Watanabe-Akaike Information Criteria (WAIC) [43]. The WAIC is a Bayesian information criterion for estimating the out-of-sample expected error, which penalises a model according to its effective number of parameters and assumes inference is made from the posterior distribution. PDMS makes inference from the posterior mean, therefore the WAIC is appropriate for our application. Details of how the WAIC is estimated can be found in Gelman et al [44]. Although WAIC adjusts for over-fitting by adding a correction for the effective number of parameters, it does not account for the increased false positive rate induced by searching over many models. PDMS does not simply choose the model with the lowest WAIC across all model sizes explored, but instead introduces an additional penalty which minimises:

Corrected criteria=$WAIC+\alpha k$

Where k is the model size, we take $\alpha=1$.

Calculating Model Accuracy

The area under ROC curves, and corresponding confidence intervals of the models' application to the test and validation datasets were calculated using the R package pROC [45].

Results for each patient were summarised as a Disease Risk Score (DRS) to determine the accuracy of classification by the 13-transcript signature, and the optimal threshold-cut-off for classification as KD or not KD, based on training set data, was determined according to Youden's J statistic by the point in the ROC curve that maximizes the distance to the identity line (maximum of (sensitivities+specificities)) [46]. The same threshold was used in accuracy calculations for the validation data.

Confidence intervals (CI) for sensitivity and specificity were calculated using Jeffrey's method. Jeffrey's method is derived from a Bayesian perspective in which the underlying proportion of interest is assigned the non-informative Jeffrey's reference prior—Beta (½, ½). [47] Thus, sensitivity 95% CIs are derived from the 2.5% and 97.5% quantiles of a Beta (p+½, q+½) distribution, where p is the number of true positives and q is the number of false negatives.

Results

The numbers of patients in each diagnostic category are shown in FIG. 2. Clinical and demographic features of the KD patients are shown in Table 1, and those of patients with other inflammatory syndromes and infections are shown in Tables 3-6. Principal Component Analysis of the normalised gene expression profiles was performed separately on the discovery (training and test) and validation groups; FIGS. 5 and 6 plot PC1 vs PC2 of these two analyses. Study groups clustered together in the discovery group, and in the validation group after combining KD and case-control data using the ComBat algorithm (see Supplementary Statistical Methods above).

TABLE 1

Clinical characteristics and laboratory values at acute time point for KD subjects in discovery and validation study group

| Patient characteristic | Discovery set n = 78 | Validation set[d] n = 72 |
|---|---|---|
| Age, months | 26.5 (16-45) | 34 (17.3-51.0) |
| Male, n (%) | 43 (55) | 45 (63) |

TABLE 1-continued

Clinical characteristics and laboratory values at acute time point for KD subjects in discovery and validation study group

| Patient characteristic | Discovery set n = 78 | Validation set[d] n = 72 |
|---|---|---|
| Illness day at sample collection[a] | 5 (4-6) | 5 (4.9-5.5) |
| CA status: | | |
| Normal, n (%) | 45 (58) | 52 (72) |
| Dilated, n (%) | 25 (32) | 15 (21) |
| Aneurysm, n (%) | 8 (10) | 5 (7) |
| Ethnicity, n (%) | | |
| Asian (includes Far East & Indian subcontinent) | 12 (15) | 12 (17) |
| European | 20 (26) | 20 (28) |
| African | 3 (4) | 2 (3) |
| Hispanic | 25 (32) | 14 (19) |
| Mixed | 15 (19) | 23 (32) |
| Other | 3 (4) | 1 (1) |
| IVIG-resistant, n (%) | 18 (23) | 15 (21) |
| Haemoglobin z-score[b] | -1.3 (-2.0--0.3) | -1.2 (-2--0.43) |
| ESR (mm/hour)[c] | 58.5 (38-78.5)[e] | 66 (49-93)[e] |

TABLE 1-continued

Clinical characteristics and laboratory values at acute time point for KD subjects in discovery and validation study group

| Patient characteristic | Discovery set n = 78 | Validation set[d] n = 72 |
|---|---|---|
| C-reactive protein (mg/L) | 119 (48-192) | 86.5 (59-173) |
| Platelet count (×10³/mm³) | 352 (303-447.5) | 408 (324-474) |
| White blood count (×10³/mm³)[a] | 14.2 (10.4-18.3) | 13.9 (11.0-19.0) |

All values shown as median (IQR). There were no significant differences between the discovery and validation patients for the characteristics. a: illness day 1=first day of fever; b: Haemoglobin normalized by age; c: >140 is written as 140; d: of 102 patients with KD, 30 patients with illness day at sampling ≥8 were excluded and the remaining 72 patients were used for diagnostic performance; e discovery vs validation P value=0.051.

Identification of Minimal Transcript Signatures

There were 1600 transcripts passing QC that were significantly differentially expressed between KD and all other diseases and healthy controls (defined as |$\log_2$| fold change|>1 in KD vs at least one of the comparator groups). To identify minimal signatures suitable for developing as a test, we next undertook variable selection using PDMS. This approach identified a 13-transcript signature (Table 2), which when implemented as a DRS had a diagnostic performance as follows: AUC in the test set was 96.2% (95% CI, 92.5%, 99.9%) with sensitivity/specificity 81.7% (95% CI, 60.0%, 94.8%), 92.1% (95% CI, 84.0%, 97.0%) respectively (FIG. 3A, B).

TABLE 2

The genes included in the diagnostic signature

| Gene symbol | Gene name | HGNC ID | Probe ID | Location | Logistic regression coefficient |
|---|---|---|---|---|---|
| CACNA1E | Calcium voltage-gated channel subunit alpha1 E | 1392 | 7510647 | 1q25.3 | 0.955 |
| DDIAS | DNA damage induced apoptosis suppressor | 26351 | 2570019 | 11q14.1 | 0.844 |
| KLHL2 | Kelch-like family member 2 | 6353 | 1070593 | 4g32.3 | 0.789 |
| PYROXD2 | Pyridine nucleotide-disulphide oxidoreductase domain 2 | 23517 | 1684497 | 10q24.2 | 0.727 |
| SMOX | Spermine oxidase | 15862 | 270068 | 20p13 | 0.675 |
| ZNF185 | Zinc finger protein 185 with LIM domain | 12976 | 6840674 | Xq28 | 0.646 |
| LINCO2035 | Long intergenic non-protein coding RNA 2035 | 52875 | 3236239 | 3q21.1 | 0.561 |
| CLIC3 | Chloride intracellular channel 3 | 2064 | 5870136 | 9q34.3 | 0.464 |
| S100P | S100 calcium binding protein P | 10504 | 1510424 | 4p16.1 | -0.405 |
| IFI27 | Interferon alpha-inducible protein 27 | 5397 | 3990170 | 14q32.12 | -0.426 |
| HS.553068 | BX103476 NCI_CGAP_Lu5 *Homo sapiens* cDNA clone | n/a | 1470450 | n/a | -0.599 |
| CD163 | CD163 molecule | 1631 | 2680092 | 12p13.31 | -0.638 |
| RTN1 | Reticulon 1 | 10467 | 6860193 | 14g23.1 | -0.690 |

The logistic regression coefficient indicates the power of the gene to discriminate KD in the PDMS model; genes with positive values show increased expression in KD relative to other diseases; genes with negative values show decreased expression in KD.

Signature Performance in Validation Set

When the signature was applied to the 72 KD cases in the validation set, the AUC was 96.5% (95% CI, 93.7%, 99.3%) with sensitivity of 90.8% (95% CI, 82.5%, 96.2%) and specificity of 89.1% (95% CI, 83.0%, 93.7%). As clinical features of KD overlap other conditions, and as any KD study group is likely to include patients without KD, we assessed whether the certainty of clinical diagnosis corresponded to the strength of the KD DRS prediction score. The performance of the 13-transcript signature in the definite, highly probable, or possible KD patients of the validation set (see methods) followed the clinical certainty of diagnosis. When analysed separately, the performance of the 13-transcript PDMS signature in definite, probable and possible KD groups followed the clinical certainty of diagnosis with ROC AUCs of 98.1% (95% CI, 94.5%, 100%), 96.3% (95% CI, 93.3%, 99.4%) and 70.0% (95% CI, 53.4%, 86.6%) respectively (FIG. 3C, D).

Performance of the Signature by Illness Day

The discovery group included KD patients up to day 7 of their illness (with day 1 as the first day of fever), and the signature was validated on patients up to and including day 7 of illness. The performance of the signature declined when applied to 30 patients on day 8-10 of their illness (FIG. 4).

Discussion

We have identified a 13-transcript signature that distinguishes KD from patients with bacterial, viral and inflammatory diseases. The high sensitivity and specificity of this signature for early diagnosis of KD suggests it might form the basis of a diagnostic test. Our findings extend previous gene expression studies in KD, which focused on immunopathogenesis [21, 25-29].

For 5 of the 13 transcripts in the signature, the expression was lower in KD patients compared to the non-KD group (Table 2). Of these 5, the S100 calcium binding protein P (S100P), has previously been reported to show increased expression in KD during the acute phase, in comparison to convalescence [30], or with viral infections [29, 30]. S100P expression was highest in bacterial patients, and selection of this transcript in the PDMS model was driven by KD-bacterial discrimination. The interferon inducible gene, interferon alpha-inducible protein 27 (IFI27) that regulates apoptosis, has been reported to be up-regulated in febrile children with viral infections compared with children with acute bacterial infections [31] and autoimmune diseases [32, 33]. Low transcript abundance of the family of genes induced by Type 1 interferons was previously reported in a comparison of whole blood gene expression in acute KD versus adenovirus infection [29], which is consistent with inclusion of IFI27 in the model as a negative predictor of KD. CD163 is transmembrane receptor expressed in macrophages and monocytes involved in bacterial clearance during the acute phase of infection [34]. A network analysis of the signature using Ingenuity Pathways Analysis reveals that 7 of the 13 transcripts in the signature were connected in a network around a central hub of TNF and IL6 (FIG. 7).

The diagnosis of KD currently relies on the presence of four of the five characteristic clinical criteria. Fewer criteria are accepted as diagnostic if coronary artery abnormalities (dilatation or aneurysms) are detected on echocardiography. Children with "incomplete KD" who do not fulfil the classical diagnostic criteria, but have prolonged fever and inflammation are at increased risk of developing CAA [35]. One reason for the greater risk of CAA in incomplete KD is the delayed diagnosis that often occurs in patients lacking all clinical features. As the clinical features of KD overlap those of many other common childhood conditions such as staphylococcal and streptococcal toxin diseases, viral exanthems, Stevens Johnson syndrome, systemic juvenile idiopathic arthritis and drug reactions [36], treatment with IVIG may be delayed while awaiting exclusion of other conditions. Conversely, because the diagnosis of KD is considered in the differential of many childhood febrile illnesses and the consequences of delayed treatment may be severe, overtreatment with IVIG or immunosuppressant second-line treatments may occur. A diagnostic test that accurately distinguishes KD from other infectious and inflammatory processes would be a significant advance in management of the disorder, reduce unnecessary investigations and inappropriate treatments, and enable earlier treatment with IVIG and other anti-inflammatory agents.

In establishing our discovery and validation study groups we aimed to include a wide range of disorders which have overlapping features with KD, including both infectious and inflammatory diseases. The signature we have identified distinguished KD from a wide range of other conditions. As KD is diagnosed based on a constellation of clinical features, and there is no gold standard for diagnosis, evaluation of biomarkers or tests is difficult. In any cohort of children treated with IVIG for presumed KD, it is likely that some patients with non-KD illness with overlapping clinical features will be included. To evaluate the correspondence of the KD DRS with levels of diagnostic certainty, we categorized all patients in the validation set as definite, probable or possible KD based on independent review of all the clinical data. We observed a higher sensitivity and specificity of our signature in the definite and highly probable than in the possible group. The diagnostic accuracy of the KD-specific signature is ready for testing in prospective studies.

We recognize both strengths and limitations in the study. Firstly, the epidemiology of KD varies globally by ethnicity, with high rates in East Asia and lower rates in Europe. Further studies are required to investigate whether there are ethnic and geographical variations in gene expression in KD. A strength of our study is that the signature was developed from a training set including a range of ethnicities. Febrile control samples in the discovery set were drawn from all centres, whilst multi-ethnic KD samples came from UCSD. Secondly, in the validation experiment, KD and case-control data from different Illumina microarray versions were combined by applying the ComBat algorithm [24], and normalising with respect to healthy control data from each platform. This normalisation may reduce both experimental and biological sources of variability between datasets and consequently, the accuracy (AUC result) of the diagnostic signature when applied to the validation set may be an underestimate compared to that obtained from a validation dataset drawn from a single microarray experiment. Thirdly, the 13-transcript signature was discovered using KD patients that were no more than 7 days into their illness. The advantage of our signature is that it might facilitate early diagnosis of KD, before 5 days of fever. However further work is required to establish the optimal signature for diagnosis in late, 'missed' KD patients.

Translation of multi-transcript signatures into a rapid clinical test for use in hospital diagnostic laboratories is challenging, but is made more achievable due to the relatively small number of transcripts in our signature and the rapidly evolving technologies for detecting nucleic acids. Furthermore, the DRS offers a new approach for individual disease risk assignment without the requirement for complex analysis, and provides a platform for development as a test where up- or down-regulated transcripts comprising the KD signature are co-located and their combined signal detected.

Our study suggests that KD can be distinguished from the range of infectious and inflammatory conditions with which it is often clinically confused using a small number of transcripts in blood. Development of a rapid test, based on this gene expression signature would be a major advance allowing earlier treatment, and thus prevention of cardiac complications of this serious childhood disease. Our findings represent a step towards better diagnosis of diseases based on molecular signatures rather than clinical criteria, and thus are relevant to many other clinical syndromes.

Data Repository

The data discussed above have been deposited in NCBI's Gene Expression Omnibus (Edgar et al., 2002) and are accessible GEO Series accession number GSE73464 (http://www.ncbi.nlm.nih.gov/geo/).

Supplementary Tables

TABLE 3

Clinical features of children in the juvenile idiopathic arthritis cohort (Discovery)

|  | Treatment-naive | Active-exacerbation/ smouldering |
|---|---|---|
| No. children | 30 | 36 |
| Age, months[a] | 163.5 (124.0-186.8) | 157 (137.8-176.5) |
| Male, n (%) | 11 (37) | 14 (39) |
| Ethnicity, n (%) | | |
| Caucasian | 27 (90) | 26 (72) |
| Turkish | 1 (3) | 1 (2) |
| Arabic | | 4 (11) |
| Black | 1 (3) | (5) |
| Indian | | 21 (2) |
| Mixed | 1 (3) | 2 (5) |
| White blood count ($\times 10^3/mm^3$)[a,b] | 6.3 (5.2-6.9) | 5.9 (5.1-6.8) |
| % neutrophils | 50.6 (44.9-57.4) | 54.9 (46.1-60.2) |
| % lymphocytes | 37.0 (32.9-44.7) | 34.1 (29.4-41.0) |
| % monocytes | 7.0 (6.3-8.0) | 7.1 (5.8-7.8) |
| % eosinophils | 2.3 (1.6-4.6) | 2.7 (1.3-4.0) |
| % basophils | 0.4 (0.3-0.8) | 0.4 (0.2-0.5) |
| ESR (mm/hour)[a] | 5 (2-10.5) | 5 (2-9) |
| C-reactive protein (mg/L)[a] | 0.9 (0.0-2.1) | 0.9 (0.3-3.1) |
| ANA positive (%) | 8 (26) | 17 (47) |
| ANCA positive (%) | 0 | 0 |

[a]All values shown as median (IQR);
[b]Lab values out of 27 patients for treatment-naive set, 35 patients for active-exacerbation/smouldering set.
ESR = erythrocyte sedimentation rate,
ANA = antinuclear antibodies,
ANCA = anti-neutrophil cytoplasmic antibodies.

TABLE 4

Clinical features of children in the Henoch-Schönlein purpura group (Discovery)

|  | Henoch-Schönlein Purpura |
|---|---|
| No. children | 18 |
| Age, months[a] | 55.5 (43.0-81.0) |
| Male, n (%) | 9 (50) |
| Ethnicity, n (%) | |
| Caucasian | 4 (22) |
| Hispanic | 4 (22) |
| Mixed | 8 (44) |
| Other | 2 (11) |
| Illness day at sample collection[a] | 3.5 (2-6) |
| White blood count ($\times 10^3/mm^3$)[a] | 12.7 (9.7-14.2)[c] |
| % neutrophils | 60.0 (45.0-67.5)[c] |
| % bands | 3.5 (0.0-9.8)[d] |
| % lymphocytes | 26.0 (15.8- 33.9)[c] |
| % monocytes | 7.0 (4.6-8.1)[c] |
| % eosinophils | 1.0 (0.0-2.1)[c] |
| Haemoglobin z-score[a,b] | −0.1 (−0.7-0.6)[d] |
| Platelet count ($\times 10^3/mm^3$)[a] | 356.0 (321.0-488.5)[d] |
| ESR (mm/hour)[a] | 23 (11-35.3)[e] |
| C-reactive protein (mg/L)[a] | 22 (8-24)[f] |

[a]All values shown as median (IQR);
[b]Hemoglobin normalized by age;
[c]Lab data available from 15 patients;
[d]Lab data available from 14 patients;
[e]Lab data available from 4 HSP;
fLab data available from 8 patients;
ESR = erythrocyte sedimentation rate

TABLE 5

Clinical features of children with bacterial and viral infection, infections of uncertain bacterial or viral aetiology and healthy controls (Discovery and Validation)

| | Discovery group | | | |
|---|---|---|---|---|
| | Definite bacterial | Definite viral | Uncertain | Healthy control |
| No. children | 52 | 94 | 96 | 55 |
| Age, months[a] | 22 (9-46) | 14 (2-39) | 27 (7-71) | 38 (20-77) |
| Male, n (%) | 22 (42) | 66 (70) | 62 (65) | 29 (53) |
| Ethnicity, n (%)[b] | | | | |
| Asian | 5 (10) | 5 (6) | 18 (21) | 5 (10) |
| Black | 2 (4) | 11 (13) | 12 (14) | 5 (10) |
| Caucasian | 35 (73) | 47 (53) | 47 (55) | 21 (44) |
| Hispanic | 0 (0) | 14 (16) | 2 (2) | 0 (0) |
| Middle East | 2 (4) | 1 (1) | 0 (0) | 4 (8) |
| Others | 4 (8) | 10 (11) | 6 (7) | 13 (27) |
| Not stated | 4 | 6 | 11 | 7 |
| Symptom days[a,c] | 5 (2-8.8) | 4.5 (3.0-6.0) | 5 (4.8-8) | n/a |
| Intensive care, n (%) | 36 (69%) | 34 (36%) | 57 (59%) | n/a |
| Deaths, n | 10 | 0 | 2 | n/a |
| White blood count ($\times 10^3/mm^3$)[a] | 12.7 (7.7-19.3) | 8.5 (6.1-12.0) | 8.4 (6.5-14.6) | 7.2 (6.4-9.75) |
| % neutrophil | 75 (49-85) | 50 (36-64) | 63 (46-79) | 45 (35-50) |
| % lymphocyte | 19 (10-36) | 34 (19-44) | 22 (15-42) | 44 (39-56) |

TABLE 5-continued

Clinical features of children with bacterial and viral infection, infections of uncertain bacterial or viral aetiology and healthy controls (Discovery and Validation)

| | | | | |
|---|---|---|---|---|
| % monocyte | 5 (3-8) | 10 (4-14) | 6 (2-12) | 6.5 (5.3-7.1) |
| % eosinophil | 0 (0-1.2) | 0 (0-1.0) | 0 (0-0.9) | 2.8 (1.6-5.6) |
| C-reactive protein[a,d] (mg/L) | 176 (98-275) | 14 (6-27) | 102 (47-176) | n/a |

| | Validation group | | | |
|---|---|---|---|---|
| | Definite bacterial | Definite viral | Uncertain | Healthy control |
| No. children | 23 | 28 | 79 | 16 |
| Age, months[a] | 22 (13-52) | 18 (7-48) | 15 (2-44) | 65 (44, 65) |
| Male, n (%) | 10 (43%) | 17 (61%) | 47 (59%) | 10 (63) |
| Ethnicity, n (%)[b] | | | | |
| Asian | 2 (9) | 2 (7) | 8 (11) | 2 (13) |
| Black | 5 (23) | 4 (14) | 14 (20) | 1 (6) |
| Caucasian | 12 (55) | 14 (52) | 42 (59) | 8 (50) |
| Hispanic | 0 (0) | 0 (0) | 0 (0) | 0 (0) |
| Middle East | 0 (0) | 3 (11) | 2 (3) | 3 (19) |
| Others | 3 (14) | 4 (15) | 5 (7) | 2 (13) |
| Not stated | 1 | 1 | 8 | 0 |
| Symptom days[a,c] | 4 (2.5-8) | 3.5 (2.8-5.3) | 4 (3-7) | n/a |
| Intensive care, n (%) | 13 (57) | 7 (23) | 42 (53) | n/a |
| Deaths, n | 1 | 1 | 8 | n/a |
| White blood count (×10³/mm³)[a] | 16.6 (10.0-9.3) | 8.3 (5.6-10.9) | 10.6 (6.5-16.0) | 8.0 (5.8-8.9) |
| % neutrophil | 82 (71-88) | 53 (41-69) | 64 (43-82) | 45 (37-49) |
| % lymphocyte | 15 (8-23) | 32 (26-48) | 30 (14-42) | 43 (38-50) |
| % monocyte | 3 (0-7) | 7 (5-10) | 5 (2-8) | 7 (6-8) |
| % eosinophil | 0 (0-0.4) | 0 (0-2) | 0 (0-1) | 2.8 (2-5) |
| C-reactive protein[a,d] (mg/L) | 217 (168-285) | 7 (1-20) | 67 (25-128) | n/a |

[a]All values shown as median (IQR);
[b]percentage of those with known ethnicity,
[c]until research blood sampling,
[d]maximum value of CRP in illness is reported.

TABLE 6

Viral and Bacterial causative pathogens in patients in the Definite Bacterial and Viral groups

| | Definite Viral | | Definite Bacterial | |
|---|---|---|---|---|
| | Discovery | Validation | Discovery | Validation |
| Viral causative pathogen | | | | |
| Adenovirus | 23 | 2 | | |
| Influenza A or B | 23 | 13 | | |
| RSV | 27 | 10 | | |
| Other | 21 | 3 | | |
| Bacterial causative pathogen | | | | |
| S. pneumoniae | | | 10 | 15 |
| S. aureus | | | 2 | 2 |
| S. pyogenes | | | 10 | 10 |
| Group B streptococcus | | | 4 | |
| E. coli | | | 2 | |
| N. meningitidis | | | 17 | |
| Enterococcus | | | 1 | |
| Kingella | | | 1 | |
| H. influenzae | | | 1 | |
| Pseudomonas spp | | | 3 | |
| Stenotrophomonas | | | 1 | |
| Klebsiella | | | | 1 |
| Total | 94 | 28 | 52 | 23 |

TABLE 7

Summary of performance of models

| | Discovery cohort | | Validation cohort | | | |
|---|---|---|---|---|---|---|
| | Training set | Test set | All | Definite KD | Highly probable KD | Possible KD |
| AUC | 0.99 | 0.962 | 0.946 | 0.981 | 0.963 | 0.7 |
| (95% CI) | (0.982, 0.998) | (0.925, 0.999) | (0.913, 0.980) | (0.945, 1.000) | (0.933, 0.994) | (0.534, 0.866) |
| Sensitivity | 0.98 | 0.817 | 0.859 | | | |
| (95% CI) | (0.925, 0.998) | (0.600, 0.948) | (0.768, 0.926) | | | |

TABLE 7-continued

Summary of performance of models

| | Discovery cohort | | Validation cohort | | | |
|---|---|---|---|---|---|---|
| | Training set | Test set | All | Definite KD | Highly probable KD | Possible KD |
| Specificity (95% CI) | 0.93 (0.898, 0.955) | 0.921 (0.840, 0.970) | 0.891 (0.830, 0.937) | | | |
| KD positive, test positive | 59 | 14 | 62 | | | |
| KD positive, test negative | 1 | 3 | 10 | | | |
| Not KD, test positive | 20 | 4 | 13 | | | |
| Not KD, test negative | 284 | 61 | 117 | | | |

EXAMPLE 2—IDENTIFICATION OF GENE SIGNATURES WITH FEWER TRANSCRIPTS

The PReMS software (Hoggart, 2018) was used to generate alternate smaller signatures (fewer transcripts) based on subsets of the original 13 transcripts.

PReMS searches over many logistic regression models constructed from optimal subsets of the biomarkers, iteratively increasing the model size. Zero centred Gaussian prior distributions are assigned to all regression coefficients to induce shrinkage. The method estimates the optimal shrinkage parameter, optimal model for each model size and the optimal model size.

The Table 8 below shows examples of smaller 5, 6, 7, 8, 9, 10, 11 and 12 transcript signatures based on combinations of transcripts from the original 13 transcripts. The AUC values for the test and validation data sets (see Example 1) is shown for each signature. Note that the sample list of gene signatures shown here is not exhaustive for the sake of brevity and is purely illustrative.

TABLE 8

Examples of smaller signatures based on subsets of the original 13 transcripts

| Number of transcripts in signature | Gene symbol | Illumina probe ID | AUC for test data set | AUC for validation data set |
|---|---|---|---|---|
| 5 | PYROXD2 | ILMN_1684497 | 0.9656 | 0.9229 |
|   | CACNA1E | ILMN_1664047 | | |
|   | CD163 | ILMN_2379599 | | |
|   | KLHL2 | ILMN_1701837 | | |
|   | SMOX | ILMN_1775380 | | |
| 5 | PYROXD2 | ILMN_1684497 | 0.9385 | 0.9206 |
|   | CACNA1E | ILMN_1664047 | | |
|   | IFI27 | ILMN_2058782 | | |
|   | KLHL2 | ILMN_1701837 | | |
|   | SMOX | ILMN_1775380 | | |
| 5 | PYROXD2 | ILMN_1684497 | 0.9348 | 0.9291 |
|   | CACNA1E | ILMN_1664047 | | |
|   | HS.553068 | ILMN_1898691 | | |
|   | IFI27 | ILMN_2058782 | | |
|   | SMOX | ILMN_1775380 | | |
| 5 | PYROXD2 | ILMN_1684497 | 0.9222 | 0.9256 |
|   | DDIAS | ILMN_1790100 | | |
|   | CACNA1E | ILMN_1664047 | | |
|   | IFI27 | ILMN_2058782 | | |
|   | SMOX | ILMN_1775380 | | |
| 5 | PYROXD2 | ILMN_1684497 | 0.9548 | 0.9409 |
|   | CACNA1E | ILMN_1664047 | | |
|   | CD163 | ILMN_2379599 | | |
|   | KLHL2 | ILMN_1701837 | | |
|   | ZNF185 | ILMN_1802888 | | |
| 5 | PYROXD2 | ILMN_1684497 | 0.9403 | 0.895 |
|   | DDIAS | ILMN_1790100 | | |
|   | CD163 | ILMN_2379599 | | |
|   | KLHL2 | ILMN_1701837 | | |
|   | SMOX | ILMN_1775380 | | |
| 6 | PYROXD2 | ILMN_1684497 | 0.9692 | 0.9371 |
|   | CACNA1E | ILMN_1664047 | | |
|   | CD163 | ILMN_2379599 | | |
|   | IFI27 | ILMN_2058782 | | |
|   | KLHL2 | ILMN_1701837 | | |
|   | SMOX | ILMN_1775380 | | |
| 6 | PYROXD2 | ILMN_1684497 | 0.971 | 0.9322 |
|   | CACNA1E | ILMN_1664047 | | |
|   | CD163 | ILMN_2379599 | | |
|   | KLHL2 | ILMN_1701837 | | |
|   | LINC02035 | ILMN_3236239 | | |
|   | SMOX | ILMN_1775380 | | |
| 6 | PYROXD2 | ILMN_1684497 | 0.9484 | 0.9413 |
|   | DDIAS | ILMN_1790100 | | |
|   | CACNA1E | ILMN_1664047 | | |
|   | CD163 | ILMN_2379599 | | |
|   | IFI27 | ILMN_2058782 | | |
|   | SMOX | ILMN_1775380 | | |
| 6 | PYROXD2 | ILMN_1684497 | 0.9557 | 0.9476 |
|   | CACNA1E | ILMN_1664047 | | |
|   | CD163 | ILMN_2379599 | | |
|   | HS.553068 | ILMN_1898691 | | |
|   | IFI27 | ILMN_2058782 | | |
|   | SMOX | ILMN_1775380 | | |
| 6 | PYROXD2 | ILMN_1684497 | 0.9538 | 0.9265 |
|   | CACNA1E | ILMN_1664047 | | |
|   | CD163 | ILMN_2379599 | | |
|   | KLHL2 | ILMN_1701837 | | |
|   | SMOX | ILMN_1775380 | | |
|   | ZNF185 | ILMN_1802888 | | |
| 6 | PYROXD2 | ILMN_1684497 | 0.9493 | 0.9274 |
|   | CACNA1E | ILMN_1664047 | | |
|   | IFI27 | ILMN_2058782 | | |
|   | KLHL2 | ILMN_1701837 | | |
|   | RTN1 | ILMN_1756928 | | |
|   | SMOX | ILMN_1775380 | | |
| 6 | PYROXD2 | ILMN_1684497 | 0.9828 | 0.9288 |
|   | CACNA1E | ILMN_1664047 | | |
|   | CD163 | ILMN_2379599 | | |
|   | CLIC3 | ILMN_1796423 | | |

TABLE 8-continued

Examples of smaller signatures based on subsets of the original 13 transcripts

| Number of transcripts in signature | Gene symbol | Illumina probe ID | AUC for test data set | AUC for validation data set |
|---|---|---|---|---|
| | KLHL2 | ILMN_1701837 | | |
| | SMOX | ILMN_1775380 | | |
| 6 | PYROXD2 | ILMN_1684497 | 0.9557 | 0.9287 |
| | CACNA1E | ILMN_1664047 | | |
| | CLIC3 | ILMN_1796423 | | |
| | IFI27 | ILMN_2058782 | | |
| | KLHL2 | ILMN_1701837 | | |
| | SMOX | ILMN_1775380 | | |
| 6 | PYROXD2 | ILMN_1684497 | 0.9448 | 0.9304 |
| | DDIAS | ILMN_1790100 | | |
| | CACNA1E | ILMN_1664047 | | |
| | IFI27 | ILMN_2058782 | | |
| | RTN1 | ILMN_1756928 | | |
| | SMOX | ILMN_1775380 | | |
| 6 | PYROXD2 | ILMN_1684497 | 0.9475 | 0.9141 |
| | DDIAS | ILMN_1790100 | | |
| | CD163 | ILMN_2379599 | | |
| | IFI27 | ILMN_2058782 | | |
| | KLHL2 | ILMN_1701837 | | |
| | SMOX | ILMN_1775380 | | |
| 7 | PYROXD2 | ILMN_1684497 | 0.971 | 0.9449 |
| | CACNA1E | ILMN_1664047 | | |
| | CD163 | ILMN_2379599 | | |
| | HS.553068 | ILMN_1898691 | | |
| | IFI27 | ILMN_2058782 | | |
| | KLHL2 | ILMN_1701837 | | |
| | SMOX | ILMN_1775380 | | |
| 7 | PYROXD2 | ILMN_1684497 | 0.9828 | 0.9429 |
| | CACNA1E | ILMN_1664047 | | |
| | CD163 | ILMN_2379599 | | |
| | CLIC3 | ILMN_1796423 | | |
| | IFI27 | ILMN_2058782 | | |
| | KLHL2 | ILMN_1701837 | | |
| | SMOX | ILMN_1775380 | | |
| 7 | PYROXD2 | ILMN_1684497 | 0.9629 | 0.9389 |
| | DDIAS | ILMN_1790100 | | |
| | CACNA1E | ILMN_1664047 | | |
| | CD163 | ILMN_2379599 | | |
| | IFI27 | ILMN_2058782 | | |
| | KLHL2 | ILMN_1701837 | | |
| | SMOX | ILMN_1775380 | | |
| 7 | PYROXD2 | ILMN_1684497 | 0.9729 | 0.94 |
| | CACNA1E | ILMN_1664047 | | |
| | CD163 | ILMN_2379599 | | |
| | IFI27 | ILMN_2058782 | | |
| | KLHL2 | ILMN_1701837 | | |
| | RTN1 | ILMN_1756928 | | |
| | SMOX | ILMN_1775380 | | |
| 7 | PYROXD2 | ILMN_1684497 | 0.9529 | 0.9485 |
| | DDIAS | ILMN_1790100 | | |
| | CACNA1E | ILMN_1664047 | | |
| | CD163 | ILMN_2379599 | | |
| | HS.553068 | ILMN_1898691 | | |
| | IFI27 | ILMN_2058782 | | |
| | SMOX | ILMN_1775380 | | |
| 8 | PYROXD2 | ILMN_1684497 | 0.9729 | 0.9456 |
| | DDIAS | ILMN_1790100 | | |
| | CACNA1E | ILMN_1664047 | | |
| | CD163 | ILMN_2379599 | | |
| | CLIC3 | ILMN_1796423 | | |
| | IFI27 | ILMN_2058782 | | |
| | KLHL2 | ILMN_1701837 | | |
| | SMOX | ILMN_1775380 | | |
| 8 | PYROXD2 | ILMN_1684497 | 0.9828 | 0.9488 |
| | CACNA1E | ILMN_1664047 | | |
| | CD163 | ILMN_2379599 | | |
| | CLIC3 | ILMN_1796423 | | |
| | HS.553068 | ILMN_1898691 | | |
| | IFI27 | ILMN_2058782 | | |
| | KLHL2 | ILMN_1701837 | | |
| | SMOX | ILMN_1775380 | | |
| 8 | PYROXD2 | ILMN_1684497 | 0.9828 | 0.9458 |
| | CACNA1E | ILMN_1664047 | | |
| | CD163 | ILMN_2379599 | | |
| | CLIC3 | ILMN_1796423 | | |
| | IFI27 | ILMN_2058782 | | |
| | KLHL2 | ILMN_1701837 | | |
| | RTN1 | ILMN_1756928 | | |
| | SMOX | ILMN_1775380 | | |
| 8 | PYROXD2 | ILMN_1684497 | 0.9701 | 0.9415 |
| | CACNA1E | ILMN_1664047 | | |
| | CD163 | ILMN_2379599 | | |
| | HS.553068 | ILMN_1898691 | | |
| | IFI27 | ILMN_2058782 | | |
| | KLHL2 | ILMN_1701837 | | |
| | S100P | ILMN_1801216 | | |
| | SMOX | ILMN_1775380 | | |
| 9 | PYROXD2 | ILMN_1684497 | 0.9783 | 0.9515 |
| | DDIAS | ILMN_1790100 | | |
| | CACNA1E | ILMN_1664047 | | |
| | CD163 | ILMN_2379599 | | |
| | CLIC3 | ILMN_1796423 | | |
| | HS.553068 | ILMN_1898691 | | |
| | IFI27 | ILMN_2058782 | | |
| | KLHL2 | ILMN_1701837 | | |
| | SMOX | ILMN_1775380 | | |
| 9 | PYROXD2 | ILMN_1684497 | 0.9792 | 0.9493 |
| | DDIAS | ILMN_1790100 | | |
| | CACNA1E | ILMN_1664047 | | |
| | CD163 | ILMN_2379599 | | |
| | CLIC3 | ILMN_1796423 | | |
| | IFI27 | ILMN_2058782 | | |
| | KLHL2 | ILMN_1701837 | | |
| | RTN1 | ILMN_1756928 | | |
| | SMOX | ILMN_1775380 | | |
| 9 | PYROXD2 | ILMN_1684497 | 0.9846 | 0.9517 |
| | CACNA1E | ILMN_1664047 | | |
| | CD163 | ILMN_2379599 | | |
| | CLIC3 | ILMN_1796423 | | |
| | HS.553068 | ILMN_1898691 | | |
| | IFI27 | ILMN_2058782 | | |
| | KLHL2 | ILMN_1701837 | | |
| | RTN1 | ILMN_1756928 | | |
| | SMOX | ILMN_1775380 | | |
| 10 | PYROXD2 | ILMN_1684497 | 0.9783 | 0.9451 |
| | DDIAS | ILMN_1790100 | | |
| | CACNA1E | ILMN_1664047 | | |
| | CD163 | ILMN_2379599 | | |
| | CLIC3 | ILMN_1796423 | | |
| | IFI27 | ILMN_2058782 | | |
| | KLHL2 | ILMN_1701837 | | |
| | RTN1 | ILMN_1756928 | | |
| | S100P | ILMN_1801216 | | |
| | SMOX | ILMN_1775380 | | |
| 10 | PYROXD2 | ILMN_1684497 | 0.9774 | 0.9543 |
| | DDIAS | ILMN_1790100 | | |
| | CACNA1E | ILMN_1664047 | | |
| | CD163 | ILMN_2379599 | | |
| | CLIC3 | ILMN_1796423 | | |
| | HS.553068 | ILMN_1898691 | | |
| | IFI27 | ILMN_2058782 | | |
| | KLHL2 | ILMN_1701837 | | |
| | RTN1 | ILMN_1756928 | | |
| | SMOX | ILMN_1775380 | | |
| 11 | PYROXD2 | ILMN_1684497 | 0.9729 | 0.9506 |
| | DDIAS | ILMN_1790100 | | |
| | CACNA1E | ILMN_1664047 | | |
| | CD163 | ILMN_2379599 | | |
| | CLIC3 | ILMN_1796423 | | |
| | HS.553068 | ILMN_1898691 | | |
| | IFI27 | ILMN_2058782 | | |
| | KLHL2 | ILMN_1701837 | | |
| | RTN1 | ILMN_1756928 | | |
| | S100P | ILMN_1801216 | | |
| | SMOX | ILMN_1775380 | | |

TABLE 8-continued

Examples of smaller signatures based on subsets of the original 13 transcripts

| Number of transcripts in signature | Gene symbol | Illumina probe ID | AUC for test data set | AUC for validation data set |
|---|---|---|---|---|
| 11 | PYROXD2 | ILMN_1684497 | 0.9828 | 0.9499 |
| | DDIAS | ILMN_1790100 | | |
| | CACNA1E | ILMN_1664047 | | |
| | CD163 | ILMN_2379599 | | |
| | CLIC3 | ILMN_1796423 | | |
| | IFI27 | ILMN_2058782 | | |
| | KLHL2 | ILMN_1701837 | | |
| | LINC02035 | ILMN_3236239 | | |
| | RTN1 | ILMN_1756928 | | |
| | S100P | ILMN_1801216 | | |
| | SMOX | ILMN_1775380 | | |
| 11 | PYROXD2 | ILMN_1684497 | 0.971 | 0.9459 |
| | DDIAS | ILMN_1790100 | | |
| | CACNA1E | ILMN_1664047 | | |
| | CD163 | ILMN_2379599 | | |
| | CLIC3 | ILMN_1796423 | | |
| | IFI27 | ILMN_2058782 | | |
| | KLHL2 | ILMN_1701837 | | |
| | RTN1 | ILMN_1756928 | | |
| | S100P | ILMN_1801216 | | |
| | SMOX | ILMN_1775380 | | |
| | ZNF185 | ILMN_1802888 | | |
| 12 | PYROXD2 | ILMN_1684497 | 0.9747 | 0.9513 |
| | DDIAS | ILMN_1790100 | | |
| | CACNA1E | ILMN_1664047 | | |
| | CD163 | ILMN_2379599 | | |
| | CLIC3 | ILMN_1796423 | | |
| | HS.553068 | ILMN_1898691 | | |
| | IFI27 | ILMN_2058782 | | |
| | KLHL2 | ILMN_1701837 | | |
| | RTN1 | ILMN_1756928 | | |
| | S100P | ILMN_1801216 | | |
| | SMOX | ILMN_1775380 | | |
| | ZNF185 | ILMN_1802888 | | |
| 12 | PYROXD2 | ILMN_1684497 | 0.9855 | 0.9553 |
| | DDIAS | ILMN_1790100 | | |
| | CACNA1E | ILMN_1664047 | | |
| | CD163 | ILMN_2379599 | | |
| | CLIC3 | ILMN_1796423 | | |
| | HS.553068 | ILMN_1898691 | | |
| | IFI27 | ILMN_2058782 | | |
| | KLHL2 | ILMN_1701837 | | |
| | LINC02035 | ILMN_3236239 | | |
| | RTN1 | ILMN_1756928 | | |
| | S100P | ILMN_1801216 | | |
| | SMOX | ILMN_1775380 | | |
| 12 | PYROXD2 | ILMN_1684497 | 0.9774 | 0.9509 |
| | DDIAS | ILMN_1790100 | | |
| | CACNA1E | ILMN_1664047 | | |
| | CD163 | ILMN_2379599 | | |
| | CLIC3 | ILMN_1796423 | | |
| | IFI27 | ILMN_2058782 | | |
| | KLHL2 | ILMN_1701837 | | |
| | LINC02035 | ILMN_3236239 | | |
| | RTN1 | ILMN_1756928 | | |
| | S100P | ILMN_1801216 | | |
| | SMOX | ILMN_1775380 | | |
| | ZNF185 | ILMN_1802888 | | |

Thus, this example demonstrates that smaller gene signatures based on subsets of 5, 6, 7, 8, 9, 10, 11 or 12 of the original 13 transcripts have good discriminatory power and are able to reliably identify individuals with KD vs individuals who do not have KD.

REFERENCES

1. Kawasaki T, Kosaki F, Okawa S, Shigematsu I, Yanagawa H. A new infantile acute febrile mucocutaneous lymph node syndrome (MLNS) prevailing in Japan. Pediatrics. 1974; 54(3): 271-6. Epub 1974 Sep. 1. PubMed PMID: 4153258.
2. Makino N, Nakamura Y, Yashiro M, Ae R, Tsuboi S, Aoyama Y, et al. Descriptive epidemiology of Kawasaki disease in Japan, 2011-2012: from the results of the 22nd nationwide survey. Journal of epidemiology/Japan Epidemiological Association. 2015; 25(3): 239-45. doi: 10.2188/jea.JE20140089. PubMed PMID: 25716368; PubMed Central PMCID: PMCPMC4341001.
3. Du Z D, Zhao D, Du J, Zhang Y L, Lin Y, Liu C, et al. Epidemiologic study on Kawasaki disease in Beijing from 2000 through 2004. The Pediatric infectious disease journal. 2007; 26(5): 449-51. doi: 10.1097/01.inf.0000261196.79223.18. PubMed PMID: 17468660.
4. Kim G B, Park S, Eun L Y, Han J W, Lee S Y, Yoon K L, et al. Epidemiology and Clinical Features of Kawasaki Disease in South Korea, 2012-2014. The Pediatric infectious disease journal. 2017; 36(5): 482-5. Epub 2016 Dec. 21. doi: 10.1097/INF.0000000000001474. PubMed PMID: 27997519.
5. Lue H C, Chen L R, Lin M T, Chang L Y, Wang J K, Lee C Y, et al. Estimation of the incidence of Kawasaki disease in Taiwan. A comparison of two data sources: nationwide hospital survey and national health insurance claims. Pediatr Neonatol. 2014; 55(2): 97-100. doi: 10.1016/j.pedneo.2013.05.011. PubMed PMID: 23890670.
6. Harnden A, Mayon-White R, Perera R, Yeates D, Goldacre M, Burgner D. Kawasaki disease in England: ethnicity, deprivation, and respiratory pathogens. The Pediatric infectious disease journal. 2009; 28(1): 21-4. PubMed PMID: 19145710.
7. Holman R C, Belay E D, Christensen K Y, Folkema A M, Steiner C A, Schonberger L B. Hospitalizations for Kawasaki syndrome among children in the United States, 1997-2007. The Pediatric infectious disease journal. 2010; 29(6): 483-8. doi: 10.1097/INF.0b013e3181cf8705. PubMed PMID: 20104198.
8. Kato H, Sugimura T, Akagi T, Sato N, Hashino K, Maeno Y, et al. Long-term consequences of Kawasaki disease. A 10- to 21-year follow-up study of 594 patients. Circulation. 1996; 94(6): 1379-85. Epub 1996 Sep. 15. PubMed PMID: 8822996.
9. Suda K, Iemura M, Nishiono H, Teramachi Y, Koteda Y, Kishimoto S, et al. Long-term prognosis of patients with Kawasaki disease complicated by giant coronary aneurysms: a single-institution experience. Circulation. 2011; 123(17): 1836-42. doi: 10.1161/CIRCULATIONAHA.110.978213. PubMed PMID: 21502578.
10. Daniels L B, Gordon J B, Burns J C. Kawasaki disease: late cardiovascular sequelae. Current opinion in cardiology. 2012; 27(6): 572-7. doi: 10.1097/HCO.0b013e3283588f06. PubMed PMID: 23075819.
11. Yu J J. Use of corticosteroids during acute phase of Kawasaki disease. World J Clin Pediatr. 2015; 4(4): 135-42. doi: 10.5409/wjcp.v4.i4.135. PubMed PMID: 26566486; PubMed Central PMCID: PMCPMC4637804.
12. Tremoulet A H, Jain S, Jaggi P, Jimenez-Fernandez S, Pancheri J M, Sun X, et al. Infliximab for intensification of primary therapy for Kawasaki disease: a phase 3 randomised, double-blind, placebo-controlled trial. Lancet. 2014; 383(9930): 1731-8. doi: 10.1016/S0140-6736 (13) 62298-9. PubMed PMID: 24572997.
13. Dominguez S R, Anderson M S, El-Adawy M, Glode M P. Preventing coronary artery abnormalities: a need for earlier diagnosis and treatment of Kawasaki disease.

Pediatr Infect Dis J. 2012; 31(12): 1217-20. Epub 2012 Jul. 5. doi: 10.1097/INF.0b013e318266bcf9. PubMed PMID: 22760536.
14. McCrindle B W, Rowley A H, Newburger J W, Burns J C, Bolger A F, Gewitz M, et al. Diagnosis, Treatment, and Long-Term Management of Kawasaki Disease: A Scientific Statement for Health Professionals From the American Heart Association. Circulation. 2017; 135(17): e927-e99. Epub 2017 Mar. 31. doi: 10.1161/CIR.0000000000000484. PubMed PMID: 28356445.
15. Anderson S T, Kaforou M, Brent A J, Wright V J, Banwell C M, Chagaluka G, et al. Diagnosis of childhood tuberculosis and host RNA expression in Africa. The New England journal of medicine. 2014; 370(18): 1712-23. doi: 10.1056/NEJMoa1303657. PubMed PMID: 24785206; PubMed Central PMCID: PMC4069985.
16. Ramilo O, Allman W, Chung W, Mejias A, Ardura M, Glaser C, et al. Gene expression patterns in blood leukocytes discriminate patients with acute infections. Blood. 2007; 109(5): 2066-77. doi: 10.1182/blood-2006-02-002477. PubMed PMID: 17105821; PubMed Central PMCID: PMCPMC1801073.
17. Frangou E A, Bertsias G K, Boumpas D T. Gene expression and regulation in systemic lupus erythematosus. Eur J Clin Invest. 2013; 43(10): 1084-96. doi: 10.1111/eci.12130. PubMed PMID: 23902282.
18. Jia H L, Liu C W, Zhang L, Xu W J, Gao X J, Bai J, et al. Sets of serum exosomal microRNAs as candidate diagnostic biomarkers for Kawasaki disease. Scientific reports. 2017; 7:44706. Epub 2017 Mar. 21. doi: 10.1038/srep44706. PubMed PMID: 28317854; PubMed Central PMCID: PMCPMC5357789.
19. Kuo H C, Hsieh K S, Ming-Huey Guo M, Weng K P, Ger L P, Chan W C, et al. Next-generation sequencing identifies micro-RNA-based biomarker panel for Kawasaki disease. The Journal of allergy and clinical immunology. 2016; 138(4): 1227-30. Epub 2016 Jul. 28. doi: 10.1016/j.jaci.2016.04.050. PubMed PMID: 27450727.
20. Herberg J A, Kaforou M, Wright V J, Shailes H, Eleftherohorinou H, Hoggart C J, et al. Diagnostic Test Accuracy of a 2-Transcript Host RNA Signature for Discriminating Bacterial vs Viral Infection in Febrile Children. JAMA. 2016; 316(8): 835-45. Epub 2016 Aug. 24. doi: 10.1001/jama.2016.11236. PubMed PMID: 27552617.
21. Hoang L T, Shimizu C, Ling L, Naim A N, Khor C C, Tremoulet A H, et al. Global gene expression profiling identifies new therapeutic targets in acute Kawasaki disease. Genome Med. 2014; 6(11): 541. doi: 10.1186/s13073-014-0102-6. PubMed PMID: 25614765; PubMed Central PMCID: PMCPMC4279699.
22. Herberg J A, Kaforou M, Gormley S, Sumner E R, Patel S, Jones K D, et al. Transcriptomic profiling in childhood H1N1/09 influenza reveals reduced expression of protein synthesis genes. J Infect Dis. 2013; 208(10): 1664-8. Epub 2013 Aug. 1. doi: 10.1093/infdis/jit348. PubMed PMID: 23901082; PubMed Central PMCID: PMCPmc3805235.
23. Watanabe S. Asymptotic Equivalence of Bayes Cross Validation and Widely Applicable Information Criterion in Singular Learning Theory. Journal of Machine Learning Research. 2010; 11:3571-94.
24. Johnson W E, Li C, Rabinovic A. Adjusting batch effects in microarray expression data using empirical Bayes methods. Biostatistics (Oxford, England). 2007; 8(1): 118-27. Epub 2006 Apr. 25. doi: 10.1093/biostatistics/kxj037. PubMed PMID: 16632515.
25. Abe J, Ebata R, Jibiki T, Yasukawa K, Saito H, Terai M. Elevated granulocyte colony-stimulating factor levels predict treatment failure in patients with Kawasaki disease. The Journal of allergy and clinical immunology. 2008; 122(5): 1008-13.e8. Epub 2008 Oct. 22. doi: 10.1016/j.jaci.2008.09.011. PubMed PMID: 18930517.
26. Abe J, Jibiki T, Noma S, Nakajima T, Saito H, Terai M. Gene expression profiling of the effect of high-dose intravenous Ig in patients with Kawasaki disease. Journal of immunology. 2005; 174(9): 5837-45. PubMed PMID: 15843588.
27. Fury W, Tremoulet A H, Watson V E, Best B M, Shimizu C, Hamilton J, et al. Transcript abundance patterns in Kawasaki disease patients with intravenous immunoglobulin resistance. Hum Immunol. 2010; 71(9): 865-73. doi: 10.1016/j.humimm.2010.06.008. PubMed PMID: 20600450; PubMed Central PMCID: PMCPMC2929310.
28. Popper S J, Shimizu C, Shike H, Kanegaye J T, Newburger J W, Sundel R P, et al. Gene-expression patterns reveal underlying biological processes in Kawasaki disease. Genome Biol. 2007; 8(12): R261. doi: 10.1186/gb-2007-8-12-r261. PubMed PMID: 18067656; PubMed Central PMCID: PMCPMC2246263.
29. Popper S J, Watson V E, Shimizu C, Kanegaye J T, Burns J C, Relman D A. Gene transcript abundance profiles distinguish Kawasaki disease from adenovirus infection. J Infect Dis. 2009; 200(4): 657-66. Epub 2009 Jul. 9. doi: 10.1086/603538. PubMed PMID: 19583510; PubMed Central PMCID: PMC2878183.
30. Ebihara T, Endo R, Kikuta H, Ishiguro N, Ma X, Shimazu M, et al. Differential gene expression of S100 protein family in leukocytes from patients with Kawasaki disease. European journal of pediatrics. 2005; 164(7): 427-31. doi: 10.1007/s00431-005-1664-5. PubMed PMID: 15838637.
31. Hu X R, Yu J S, Crosby S D, Storch G A. Gene expression profiles in febrile children with defined viral and bacterial infection. P Natl Acad Sci USA. 2013; 110(31): 12792-7. doi: 10.1073/pnas.1302968110. PubMed PMID: WOS: 000322441500067.
32. O'Hanlon T P, Rider L G, Gan L, Fannin R, Paules R S, Umbach D M, et al. Gene expression profiles from discordant monozygotic twins suggest that molecular pathways are shared among multiple systemic autoimmune diseases. Arthritis Res Ther. 2011; 13(2): R69. doi: 10.1186/ar3330. PubMed PMID: 21521520; PubMed Central PMCID: PMCPMC3132064.
33. Ishii T, Onda H, Tanigawa A, Ohshima S, Fujiwara H, *Mima* T, et al. Isolation and expression profiling of genes upregulated in the peripheral blood cells of systemic lupus erythematosus patients. DNA Res. 2005; 12(6): 429-39. doi: 10.1093/dnares/dsi020. PubMed PMID: WOS: 000242119900004.
34. Fabriek B O, van Bruggen R, Deng D M, Ligtenberg A J, Nazmi K, Schornagel K, et al. The macrophage scavenger receptor CD163 functions as an innate immune sensor for bacteria. Blood. 2009; 113(4): 887-92. doi: 10.1182/blood-2008-07-167064. PubMed PMID: 18849484.
35. Minich L L, Sleeper L A, Atz A M, McCrindle B W, Lu M, Colan S D, et al. Delayed diagnosis of Kawasaki disease: what are the risk factors? Pediatrics. 2007; 120 (6): e1434-40. doi: 10.1542/peds.2007-0815. PubMed PMID: 18025079.
36. Newburger J W, Takahashi M, Gerber M A, Gewitz M H, Tani L Y, Burns J C, et al. Diagnosis, treatment, and long-term management of Kawasaki disease: a statement for health professionals from the Committee on Rheumatic Fever, Endocarditis and Kawasaki Disease, Council on Cardiovascular Disease in the Young, American Heart Association. Circulation. 2004; 110(17): 2747-71. doi: 10.1161/01.CIR.0000145143.19711.78. PubMed PMID: 15505111.
37. Petty R E, Southwood T R, Manners P, Baum J, Glass D N, Goldenberg J, et al. International League of Associations for Rheumatology classification of juvenile idiopathic arthritis: second revision, Edmonton, 2001. J Rheumatol. 2004; 31(2): 390-2. PubMed PMID: 14760812.
38. Du P, Kibbe W A, Lin S M. lumi: a pipeline for processing Illumina microarray. Bioinformatics. 2008; 24(13): 1547-8. doi: 10.1093/bioinformatics/btn224. PubMed PMID: 18467348.
39. Hoang L T, Shimizu C, Ling L, Naim A N, Khor C C, Tremoulet A H, et al. Global gene expression profiling identifies new therapeutic targets in acute Kawasaki disease. Genome Med. 2014; 6(11): 541. doi: 10.1186/s13073-014-0102-6. PubMed PMID: 25614765; PubMed Central PMCID: PMCPMC4279699.
40. Herberg J A, Kaforou M, Gormley S, Sumner E R, Patel S, Jones K D, et al. Transcriptomic profiling in childhood H1N1/09 influenza reveals reduced expression of protein synthesis genes. J Infect Dis. 2013; 208(10): 1664-8. Epub 2013 Aug. 1. doi: 10.1093/infdis/jit348. PubMed PMID: 23901082; PubMed Central PMCID: PMCPmc3805235.
41. Johnson W E, Li C, Rabinovic A. Adjusting batch effects in microarray expression data using empirical Bayes methods. Biostatistics (Oxford, England). 2007; 8(1): 118-27. Epub 2006 Apr. 25. doi: 10.1093/biostatistics/kxj037. PubMed PMID: 16632515.
42. Ritchie M E, Phipson B, Wu D, Hu Y, Law C W, Shi W, et al. limma powers differential expression analyses for RNA-sequencing and microarray studies. Nucleic Acids Res. 2015; 43(7): e47. doi: 10.1093/nar/gkv007. PubMed PMID: 25605792; PubMed Central PMCID: PMCPMC4402510.
43. Watanabe S. Asymptotic Equivalence of Bayes Cross Validation and Widely Applicable Information Criterion in Singular Learning Theory. Journal of Machine Learning Research. 2010; 11:3571-94.
44. Gelman A, Hwang J, Vehtari A. Understanding predictive information criteria for Bayesian models. Statistics and Computing. 2014; 24(6): 997-1016.
45. Robin X, Turck N, Hainard A, Tiberti N, Lisacek F, Sanchez J C, et al. pROC: an open-source package for R and S+ to analyze and compare ROC curves. BMC bioinformatics. 2011; 12:77. doi: 10.1186/1471-2105-12-77. PubMed PMID: 21414208; PubMed Central PMCID: PMC3068975.
46. Youden W J. Index for rating diagnostic tests. Cancer. 1950; 3(1): 32-5. Epub 1950 Jan. 1. PubMed PMID: 15405679.
47. Bernardo J M, Smith A F M. Bayesian theory. Chichester, Eng.; New York: Wiley; 1994. xiv, 586 p. p.
48. Hoggart C. J. (2018). PReMS: Parallel Regularised Regression Model Search for sparse bio-signature discovery. bioRxiv 355479; doi: https://doi.org/10.1101/355479.

The invention claimed is:
1. A method of treating a subject having Kawasaki disease (KD), comprising administering a treatment for KD to the subject, wherein the subject is a child that has been previously identified as having Kawasaki disease by detecting in a subject derived blood RNA sample a modulation in gene expression levels of a gene signature comprising PYROXD2 and at least 4 of the following genes: CACNA1E, DDIAS, KLHL2, SMOX, ZNF185, LINC02035, CLIC3, S100P, IFI27, HS.553068, CD163, and RTN1, wherein the treatment is gamma globulin (IVIg), aspirin, or other anti-inflammatory agents.

2. The method according to claim 1, wherein the gene signature comprises PYROXD2 and 5, 6, 7, 8, 9, 10, 11, or 12 of the following genes-: CACNA1E, DDIAS, KLHL2, SMOX, ZNF185, LINC02035, CLIC3, S100P, IFI27, HS.553068, CD163, and RTN1.

3. The method according to claim 1, wherein the gene signature comprises CACNA1E.

4. The method according to claim 1, wherein the gene signature comprises SMOX.

5. The method according to claim 1, wherein the gene signature comprises CD163.

6. The method according to claim 1, wherein the gene signature comprises:
   (i) PYROXD2 and CACNA1E;
   (ii) PYROXD2 and SMOX; or
   (iii) PYROXD2, CACNA1E and SMOX.

7. The method according to claim 1, wherein the gene signature comprises or consists of any one of the following combinations of genes:
   (i) PYROXD2, CACNA1E, CD163, KLHL2 and SMOX;
   (ii) PYROXD2, CACNA1E, IFI27, KLHL2 and SMOX;
   (iii) PYROXD2, CACNA1E, HS.553068, IFI27 and SMOX;
   (iv) PYROXD2, DDIAS, CACNA1E, IFI27 and SMOX;
   (v) PYROXD2, CACNA1E, CD163, KLHL2 and ZNF185;
   (vi) PYROXD2, DDIAS, CD163, KLHL2 and SMOX;
   (vii) PYROXD2, CACNA1E, CD163, IFI27, KLHL2 and SMOX;
   (viii) PYROXD2, CACNA1E, CD163, KLHL2, LINC02035 and SMOX;
   (ix) PYROXD2, DDIAS, CACNA1E, CD163, IFI27 and SMOX;
   (x) PYROXD2, CACNA1E, CD163, HS.553068, IFI27 and SMOX;
   (xi) PYROXD2, CACNA1E, CD163, KLHL2, SMOX and ZNF185;
   (xii) PYROXD2, CACNA1E, IFI27, KLHL2, RTN1 and SMOX;
   (xiii) PYROXD2, CACNA1E, CD163, CLIC3, KLHL2 and SMOX;
   (xiv) PYROXD2, CACNA1E, CLIC3, IFI27, KLHL2 and SMOX;
   (xv) PYROXD2, DDIAS, CACNA1E, IFI27, RTN1 and SMOX;
   (xvi) PYROXD2, DDIAS, CD163, IFI27, KLHL2 and SMOX;
   (xvii) PYROXD2, CACNA1E, CD163, HS.553068, IFI27, KLHL2 and SMOX;
   (xviii) PYROXD2, CACNA1E, CD163, CLIC3, IFI27, KLHL2 and SMOX;
   (xix) PYROXD2, DDIAS, CACNA1E, CD163, IFI27, KLHL2 and SMOX;
   (xx) PYROXD2, CACNA1E, CD163, IFI27, KLHL2, RTN1 and SMOX;
   (xxi) PYROXD2, DDIAS, CACNA1E, CD163, HS.553068, IFI27 and SMOX; (xxii) PYROXD2, DDIAS, CACNA1E, CD163, CLIC3, IFI27, KLHL2 and SMOX;
   (xxiii) PYROXD2, CACNA1E, CD163, CLIC3, HS.553068, IFI27, KLHL2 and SMOX;

(xxiv) PYROXD2, CACNA1E, CD163, CLIC3, IFI27, KLHL2, RTN1 and SMOX;
(xxv) PYROXD2, CACNA1E, CD163, HS.553068, IFI27, KLHL2, S100P and SMOX;
(xxvi) PYROXD2, DDIAS, CACNA1E, CD163, CLIC3, HS.553068, IFI27, KLHL2 and SMOX;
(xxvii) PYROXD2, DDIAS, CACNA1E, CD163, CLIC3, IFI27, KLHL2, RTN1 and SMOX;
(xxviii) PYROXD2, CACNA1E, CD163, CLIC3, HS.553068, IFI27, KLHL2, RTN1 and SMOX;
(xxix) PYROXD2, DDIAS, CACNA1E, CD163, CLIC3, IFI27, KLHL2, RTN1, S100P and SMOX;
(xxx) PYROXD2, DDIAS, CACNA1E, CD163, CLIC3, HS.553068, IFI27, KLHL2, RTN1 and SMOX;
(xxxi) PYROXD2, DDIAS, CACNA1E, CD163, CLIC3, HS.553068, IFI27, KLHL2, RTN1, S100P and SMOX;
(xxxii) PYROXD2, DDIAS, CACNA1E, CD163, CLIC3, IFI27, KLHL2, LINC02035, RTN1, S100P and SMOX;
(xxxiii) PYROXD2, DDIAS, CACNA1E, CD163, CLIC3, IFI27, KLHL2, RTN1, S100P, SMOX and ZNF185;
(xxxiv) PYROXD2, DDIAS, CACNA1E, CD163, CLIC3, HS.553068, IFI27, KLHL2, RTN1, S100P, SMOX and ZNF185;
(xxxv) PYROXD2, DDIAS, CACNA1E, CD163, CLIC3, HS.553068, IFI27, KLHL2, LINC02035, RTN1, S100P and SMOX; or
(xxxvi) PYROXD2, DDIAS, CACNA1E, CD163, CLIC3, IFI27, KLHL2, LINC02035, RTN1, S100P, SMOX and ZNF185.

8. The method according to claim 1, wherein the gene signature comprises or consists of CACNA1E, DDIAS, KLHL2, PYROXD2, SMOX, ZNF185, LINC02035, CLIC3, S100P, IFI27, HS.553068, CD163, and RTN1.

9. The method according to claim 1, wherein the method further incorporates detecting the expression levels of one or more housekeeping genes.

10. The method according to claim 1, wherein the subject with KD was identified in the presence of or discriminated from a patient with one or more of the following: a bacterial infection, a viral infection and an inflammatory condition.

11. The method according to claim 1, wherein the subject has a fever.

12. The method according to claim 1, wherein the analysis of gene expression modulation employs a microarray, a gene chip or PCR.

* * * * *